(12) United States Patent
Pan et al.

(10) Patent No.: US 6,972,319 B1
(45) Date of Patent: Dec. 6, 2005

(54) PITUITARY ADENYLATE CYCLASE ACTIVATING PEPTIDE (PACAP)RECEPTOR 3 (R3) AGONISTS AND THEIR PHARMACOLOGICAL METHODS OF USE

(75) Inventors: Clark Pan, Castro Valley, CA (US); Manami Tsutsumi, Stratford, CT (US); Armen B. Shanafelt, Carmel, IN (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 251 days.

(21) Appl. No.: 09/671,773

(22) Filed: Sep. 27, 2000

Related U.S. Application Data
(60) Provisional application No. 60/327,556, filed on Jun. 15, 2000, and provisional application No. 60/240,954, filed on Sep. 28, 1999.

(51) Int. Cl.[7] .......................... C07K 14/00; A61K 38/16
(52) U.S. Cl. ......................................... 530/324; 514/12
(58) Field of Search ............................... 530/324, 326; 514/12, 866; 930/170

(56) References Cited

U.S. PATENT DOCUMENTS

| | | | | |
|---|---|---|---|---|
| 5,234,907 A | * | 8/1993 | Bolin | ........................... 514/12 |
| 5,376,637 A | * | 12/1994 | Sawai et al. | ................... 514/12 |
| 5,677,419 A | | 10/1997 | Bolin | |

FOREIGN PATENT DOCUMENTS

| | | |
|---|---|---|
| EP | 0 796 867 A1 | 9/1997 |
| WO | WO 91/14786 | 10/1991 |
| WO | WO 98/02453 | 1/1998 |
| WO | WO 99/47159 | 9/1999 |
| WO | WO 00/05260 | 2/2000 |

OTHER PUBLICATIONS

Gourlet et al., Vasoactive intestinal peptide modification at position 22 allows discrimination between receptor subtypes. European Journal of Phamacology, vol. 348, No. 1, May 1, 1998, pp. 95–99.

Inagaki et al., Cloning and functional characterization of a third pituitary adenylate cyclase–activating polypeptide receptor subtype expressed in insulin–secreting cells. Proceedings of the National Academy of Sciences of the United States, vol. 91, No. 7, 1994, pp. 2679–2683.

Gourlet, et al., C–Terminally Shortened Pituitary Adenylate Cyclase–Activating Peptides (PACAP) Descriminate PACAP I PACAP II–VIP1 and PACAP II–VIP2 Recombinant Receptors. Regulatory Peptides, NL, Elsevier Science BV, vol. 62, No. 2/03, 1996, pp. 125–130.

Gourlet, et al, Analogues of VIP, helodermin and PACAP discriminate between rat and human VIP1 and VIP2 receptors. Annals of the New York Academy of Sciences, vol. 865, Dec. 11, 1998, pp. 247–252.

Dickinson et al., VIP and PACAP: very important in pain?, Trends in Pharmacological Sciences, GB, Elsevier Trends Journal, Cambridge, vol. 20, No. 8, Aug. 1, 1999, pp. 324–329.

Harmar, et al., International union of pharmacology, XVIII, Nomenclature of receptors for vasoactive intestinal peptide and pituitary adenylte cyclase–activating polypeptide, Pharmacological Reviews, vol. 50, No. 2, Jun. 1998 pp. 265–270.

Gourlet et al., The long acting vasoactive intestinal polypeptide agonist R025–1553IS highly selective of the VIP2 Receptor Subclass, Peptides, US, Elmsford, vol. 18, No. 3, 1997, pp. 403–408.

Robberecht et al., Interet Des Recepteurs Recombinants Dans L'Elaboration D'Agonistes et D'Antagonistes Des Recepteurs Du VIP Et Du PACAP. Journal de pharmacie de Belgique, pp. 165–169.

Nokihara et al., Receptor recognition of PACAP and VIP examined by binding studies production and biological actions both in vivo and in vitro by means of selective residue substitution, Edinburgh, Sep. 8–13, 1996, West Midlands: Mayflower Scientific, GB, vol. Symp. 24, 1996, pp. 63–66.

Gourlet et al., Addition of the (28–38) peptide sequence of PACAP to the VIP sequence modifies peptide selectively and efficacy, International Journal of peptide and protein research, DK, Munksgaard, Copenhagen, vol. 48, No. ,4 Oct. 1, 1996, pp. 391–396.

Pohl, Molecular cloning of the helodermin and exedin–4 cDNAs in the lizard: relationship to vasoactive intestinal polypeptide/pituitary adenylate cyclase activating polypeptide and glucagon–like peptide 1 and evidence against the existence of mammalian homologues, Journal of Biogical Chemistry, vol. 273, No. 16, Apr. 17, 1998, pp. 9778–9784.

Bolin, et al, Design and development of a vasoactive intestinal peptide analog as a novel therapeutic for design and development of a vasoactive intestinal peptide analog as a novel therapeutic for bronchial asthma, Biopolymers 1995;37(2):57–66.

(Continued)

*Primary Examiner*—Majorie Moran
(74) *Attorney, Agent, or Firm*—Susan M. Pellegrino

(57) ABSTRACT

This invention provides novel peptides that function in vivo to stimulate insulin release from pancreatic beta cells in a glucose-dependent fashion. These insulin secretagogue peptides are shown to stimulate insulin release in rat islet cells in vitro, and in vivo. The peptides of the present invention provide a new therapy for patients with decreased endogenous insulin secretion, in particular type 2 diabetics. In particular, the invention is a polypeptide selected from a specific group of VIP/PACAP-related polypeptides, or functional equivalents thereof. The invention is also directed to a method of treating a metabolic disease in a mammal comprising administering a therapeutically effective amount of the insulin secretagogue peptides to said mammal. Also disclosed are methods of making the peptides, both recombinant and synthetic.

5 Claims, 23 Drawing Sheets

OTHER PUBLICATIONS

Yokota, et al, PACAP stimulates glucose output from the perfursed rat liver. Peptides 16:55–60, 1995.

Straub et al., A wortmannin–sensitive signal transduction pathway is involved in the stimulation of insulin release by vasoactive intetinal polypeptide and pituitary adenylate cyclase–activating polypeptide, J Biol Chem 271: 1660–1668, 1996.

Sekiguchi, et al., Glycogenolytic activity of pituitary adenylate cyclase activating polypeptide (PACAP) in vivo and in vitro Life Sci vol. 55, No. 15, pp. 1219–1228, 1994.

Filipsson, et al, PACAP and PACAP receptors in insulin producing tissues: localization and effects. Regul Pept 74: 167–175, 1998.

Nicole et al., Identification of key resideus for interaction of vasoactive intestinal peptide with human VPACI, and VPAC2 Receptors and Development of a highly selective of a highly selective VPAC1 receptor agonist. The Journal of Biological Chemistry vol. 275, No. 31, pp 24003–24012, (2000).

Xia et al., Novel cyclic peptide agonist of high potency and selectivity for the type II vasoactive intestinal peptide receptor, J Pharmacol Exp Ther. May 1997; 281(2): 629–33.

Yada et al., Pituitary adenylate cyclase activating polypeptide is an extraordinarily potent intra–pancreatic regulator of insulin secretion from islet beta–cells. J Biol Chem vol. 269, No. 2, Issue of Jan. 14, pp 1290–1293, 1994.

Vandermeers et al., Antagonistic properties are shifted back to agonist properties by further N–terminal shortening of pituitary adenylate–cyclase–activating peptides in human neuroblastoma NB–OK–1 Cell membranes. (Eur. J. Biochem. 208, 815–819 (1992).

Komatsu et al., Augmentation of insulin release by glucose in the absence of extracellular ca2+ (Diabetes, vol. 46, Dec. 1997), pp. 1928–1938.

* cited by examiner

|       |   |                                               |    | SEQ. ID NO. |
|-------|---|-----------------------------------------------|----|------|
| R3P8  | 1 | HSDAVFTDNYTRLRKQMAVKKYLNSIKK-NH2              | 28 | 11   |
| R3P9* | 1 | HSDAVFTDNYTRLRKQMAVKKYLNSIKKGGT               | 31 | 12   |
| R3P10 | 1 | HSDAVFTENYTKLRKQLAAKKYLNDLLNGGT               | 31 | 13   |
| R3P11 | 1 | HSDAVFTDNYTKLRKQLAAKKYLNDILNGGT               | 31 | 14   |
| R3P19 | 1 | HSDAVFTENYTKLRKQLAAKKYLNDLKKGGTSWCEPGWCR      | 39 | 18   |
| R3P22 | 1 | HSDAVFTDNYTRLRKQLAAKKYLNSIKKGGT               | 31 | 21   |
| R3P24 | 1 | HSDAVFTDNYTRLRKQLAAKKYLNDIKNGGT               | 31 | 22   |
| R3P25 | 1 | HSDAVFTDNYTRLRKQLAVKKYLNSIKKGGT               | 31 | 23   |
| R3P26 | 1 | HSDAVFTDNYTRLRKQMAAKKYLNSIKKGGT               | 31 | 24   |
| R3P29 | 1 | HSDAVFTDNYTRLRKQLAVKKYLNDIKNGGT               | 31 | 25   |
| R3P30 | 1 | HSDAVFTDNYTRLRKQLAAKKYLNSIKNGGT               | 31 | 26   |
| R3P36 | 1 | HSDAVFTDNYTRLRKQLAAKKYLNDIKKKRY               | 31 | 32   |
| rR3P41 | 1 | HSDAVFTDNYTRLRKQMAVKKYLNSIKK                 | 28 | 33   |
| rR3P42 | 1 | HSDAVFTDNYTRLRKQMAVKKYLNSIKN                 | 28 | 34   |
| rR3P43 | 1 | HSDAVFTDNYTRLRKQMAVKKYLNSILK                 | 28 | 35   |
| rR3P44 | 1 | HSDAVFTDNYTELRKQMAVKKYLNSILN                 | 28 | 36   |
| rR3P48 | 1 | HSDAVFTDNYTRLRKQMAVKKYLNDILN                 | 28 | 40   |
| rR3P49 | 1 | HSDAVFTDNYTRLRKQMAAKKYLNSIKN                 | 28 | 41   |
| rR3P50 | 1 | HSDAVFTDNYTRLRKQMAAKKYLNSILK                 | 28 | 42   |
| rR3P51* | 1 | HSDAVFTDNYTRLRKQMAAKKYLNSIKK                | 28 | 43   |
| rR3P52 | 1 | HSDAVFTDNYTRLRKQMAAKKYLNSIKKKRY              | 31 | 44   |
| rR3P53* | 1 | HSDAVFTDNYTRLRKQMAAKKYLNSIKKKR              | 30 | 45   |
| rR3P54 | 1 | HSDAVFTDNYTRLRKQMAAKKYLNSIKKK                | 29 | 46   |
| rR3P55* | 1 | HSDAVFTDNYTRLRKQMAAKKYLNSIKNKRY             | 31 | 47   |
| rR3P56 | 1 | HSDAVFTDNYTRLRKQMAVKKYLNSIKKKRY              | 31 | 48   |
| rR3P57 | 1 | HSDAVFTDNYTRLRKQMAVKKYLNSIKKKR               | 30 | 49   |
| rR3P58 | 1 | HSDAVFTDNYTRLRKQMAVKKYLNSIKKK                | 29 | 50   |
| rR3P59 | 1 | HSDAVFTDNYTRLRKQMAVKKYLNSIKNKRY              | 31 | 51   |
| rR3P60 | 1 | HSDAVFTDNYTRLRKQVAAKKYLQSIKK                 | 28 | 52   |
| rR3P61 | 1 | HSDAVFTDNYTRLRKQIAAKKYLQTIKK                 | 28 | 53   |
| R3P6  | 1 | HSDGIFTESYSRYRKQMAVKKYLAALKKKRYKQRVKNK        | 38 | 57   |
| R3P7  | 1 | HSDAVFTENYTRLRKQMAVKKYLNSLKK-NH2              | 28 | 58   |
| R3P15 | 1 | HSDGIFTDSYSRYRKQMAVKKYLSAVRHGQT-NH2           | 31 | 59   |
| R3P16 | 1 | HSDGIFTDSYSRYRKQMAVKKYLAAVKKQGGT-NH2          | 31 | 60   |
| R3P17 | 1 | HSDGIFTDSYSRYRKQMAVKKYLAAVKKYLAAVRHG-NH2      | 36 | 61   |
| R3P23 | 1 | HSDAVFTDNYTRLRKQLAAKKYLNDILKGGT               | 31 | 63   |
| R3P27 | 1 | HSDAVFTDNYTRLRKQLAAKKYLNDILNGGT               | 31 | 64   |
| R3P28 | 1 | HSDAVFTDNYTRLRKQLAVKKYLNDILKGGT               | 31 | 65   |
| R3P37 | 1 | HSDGIFTDSYSRYRKQLAAKKYLADVKKGGT               | 31 | 66   |
| R3P38 | 1 | HSDGIFTDSYSRYRKQLAAKKYLADVKK                  | 28 | 67   |
| R3P39 | 1 | HSDGIFTDSYSRYRKQLAVKKYLAAVKK                  | 28 | 68   |
| R3P40 | 1 | HSDGIFTDSYSRYRKQMAVKKYLAAVKK                  | 28 | 69   |
| R3P62 | 1 | HSDAVFTDNYTRLRKQVAAKKYLNSIKK                  | 28 | 70   |
| R3P65 | 1 | HSDAVFTDNYTRLRKQMAAKKYLNSIKNKR                | 30 | 71   |
| R3P66 | 1 | HSDAVFTDNYTRLRKQVAAKKYLQSIKNKRY               | 31 | 72   |
| R3P67 | 1 | HSDAVFTDNYTRLRKQLAAKKYLNTIKNKRY               | 31 | 73   |
| R3P68 | 1 | HSDAVFTDNYTRLRKQVAAKKYLNSIKNKRY               | 31 | 74   |
| R3P69 | 1 | HSDAVFTDNYTRLRKQMAAKKYLQSIKNKRY               | 31 | 75   |
| R3P70 | 1 | HSDAVFTDNYTRLRKQMAAKKYLNTIKNKRY               | 31 | 76   |
| R3P71 | 1 | HSDAVFTDQYTRLRKQMAAKKYLNSIKNKRY               | 31 | 77   |
| R3P72 | 1 | HSDAVFTDQYTRLRKQLAAKKYLNTIKNKRY               | 31 | 78   |
| R3P73 | 1 | HSDAVFTDNYTRLRKQMAAHKYLNSIKNKRY               | 31 | 79   |
| R3P74 | 1 | HSDAVFTDNYTRLRKQMAAKHYLNSIKNKRY               | 31 | 80   |
| R3P75 | 1 | HSDAVFTDQYTRLRKQLAAHKYLNTIKNKRY               | 31 | 81   |
| R3P76 | 1 | HSDAVFTDQYTRLRKQLAAKHYLNTIKNKRY               | 31 | 82   |
| R3P77 | 1 | HSDAVFTDNYTRLRKQVAAKKYLQSIKKKR                | 30 | 83   |

| Name | | Sequence | | |
|---|---|---|---|---|
| R3P78 | 1 | HSDAVFTDNYTRLRKQVAAKKYLNSIKKKR | 30 | 84 |
| R3P79 | 1 | HSDAVFTDNYTRLRKQVAAKKYLNSIKNKRY | 31 | 85 |
| R3P80 | 1 | HSDAVFTDNYTRLRKQVAVKKYLQSIKKKR | 30 | 86 |
| R3P81 | 1 | HSDAVFTDNYTRLRKQVAVKKYLQSIKKK | 29 | 87 |
| R3P82 | 1 | HSDAVFTDNYTRLRKQVAVKKYLQSIKNKRY | 31 | 88 |
| R3P83 | 1 | HSDAVFTDNYTRLRKQVAAKKYLQSILKKRY | 31 | 89 |
| R3P84 | 1 | HSDAVFTDNYTRLRKQVAAKKYLQSILKKR | 30 | 90 |
| R3P85 | 1 | HSDAVFTDNYTRLRKQVAAKKYLQSILKK | 29 | 91 |
| R3P86 | 1 | HSDAVFTDNYTRLRKQVAAKKYLQSIKNK | 29 | 92 |
| R3P87 | 1 | HSDAVFTDNYTRLRKQVAVKKYLQSILKKRY | 31 | 93 |
| R3P88 | 1 | HSDAVFTDNYTRLRKQVAVKKYLQSILKKR | 30 | 94 |
| R3P89 | 1 | HSDAVFTDNYTRLRKQVAVKKYLQSILKK | 29 | 95 |
| R3P91 | 1 | HSDAVFTDNYTRLRKQVAVKKYLQSIKNK | 29 | 96 |
| R3P92 | 1 | HSDAVFTDNYTRLRKQVAAKKYLQSILNKRY | 31 | 97 |
| R3P93 | 1 | HSDAVFTDNYTRLRKQVAAKKYLQSILNKR | 30 | 98 |
| R3P94 | 1 | HSDAVFTDNYTRLRKQVAAKKYLQSILNK | 29 | 99 |
| rR3P99 | 1 | HSDAVFTDNYTRLRKQMAEKKYLNSIKNKR | 30 | 102 |
| rR3P100 | 1 | HSDAVFTDNYTRLRKQMAFKKYLNSIKNKR | 30 | 103 |
| rR3P101 | 1 | HSDAVFTDNYTRLRKQMAGKKYLNSIKNKR | 30 | 104 |
| rR3P102 | 1 | HSDAVFTDNYTRLRKQMAHKKYLNSIKNKR | 30 | 105 |
| rR3P103 | 1 | HSDAVFTDNYTRLRKQMAIKKYLNSIKNKR | 30 | 106 |
| rR3P104 | 1 | HSDAVFTDNYTRLRKQMAKKKYLNSIKNKR | 30 | 107 |
| rR3P105 | 1 | HSDAVFTDNYTRLRKQMALKKYLNSIKNKR | 30 | 108 |
| rR3P106 | 1 | HSDAVFTDNYTRLRKQMAMKKYLNSIKNKR | 30 | 109 |
| rR3P107 | 1 | HSDAVFTDNYTRLRKQMANKKYLNSIKNKR | 30 | 110 |
| rR3P108 | 1 | HSDAVFTDNYTRLRKQMAPKKYLNSIKNKR | 30 | 111 |
| rR3P109 | 1 | HSDAVFTDNYTRLRKQMAQKKYLNSIKNKR | 30 | 112 |
| rR3P110 | 1 | HSDAVFTDNYTRLRKQMARKKYLNSIKNKR | 30 | 113 |
| rR3P111 | 1 | HSDAVFTDNYTRLRKQMASKKYLNSIKNKR | 30 | 114 |
| rR3P112 | 1 | HSDAVFTDNYTRLRKQMATKKYLNSIKNKR | 30 | 115 |
| rR3P113 | 1 | HSDAVFTDNYTRLRKQMAVKKYLNSIKNKR | 30 | 116 |
| rR3P114 | 1 | HSDAVFTDNYTRLRKQMAWKKYLNSIKNKR | 30 | 117 |
| rR3P115 | 1 | HSDAVFTDNYTRLRKQMAYKKYLNSIKNKR | 30 | 118 |
| rR3P116 | 1 | HSDAVFTDNYTRLRKQMAAKKYLNSIANKR | 30 | 119 |
| rR3P118 | 1 | HSDAVFTDNYTRLRKQMAAKKYLNSIDNKR | 30 | 121 |
| rR3P119 | 1 | HSDAVFTDNYTRLRKQMAAKKYLNSIENKR | 30 | 122 |
| rR3P120 | 1 | HSDAVFTDNYTRLRKQMAAKKYLNSIFNKR | 30 | 123 |
| rR3P121 | 1 | HSDAVFTDNYTRLRKQMAAKKYLNSIGNKR | 30 | 124 |
| rR3P122 | 1 | HSDAVFTDNYTRLRKQMAAKKYLNSIHNKR | 30 | 125 |
| rR3P123 | 1 | HSDAVFTDNYTRLRKQMAAKKYLNSIINKR | 30 | 126 |
| rR3P124 | 1 | HSDAVFTDNYTRLRKQMAAKKYLNSIMNKR | 30 | 127 |
| rR3P125 | 1 | HSDAVFTDNYTRLRKQMAAKKYLNSINNKR | 30 | 128 |
| rR3P126 | 1 | HSDAVFTDNYTRLRKQMAAKKYLNSIPNKR | 30 | 129 |
| rR3P127 | 1 | HSDAVFTDNYTRLRKQMAAKKYLNSIQNKR | 30 | 130 |
| rR3P128 | 1 | HSDAVFTDNYTRLRKQMAAKKYLNSIRNKR | 30 | 131 |
| rR3P129 | 1 | HSDAVFTDNYTRLRKQMAAKKYLNSISNKR | 30 | 132 |
| rR3P130 | 1 | HSDAVFTDNYTRLRKQMAAKKYLNSITNKR | 30 | 133 |
| rR3P131 | 1 | HSDAVFTDNYTRLRKQMAAKKYLNSIVNKR | 30 | 134 |
| rR3P132 | 1 | HSDAVFTDNYTRLRKQMAAKKYLNSIWNKR | 30 | 135 |
| rR3P133 | 1 | HSDAVFTDNYTRLRKQMAAKKYLNSIYNKR | 30 | 136 |
| rR3P134 | 1 | HSDAVFTDNYTRLRKQMAAKKYLNSIKNAR | 30 | 137 |
| rR3P136 | 1 | HSDAVFTDNYTRLRKQMAAKKYLNSIKNDR | 30 | 139 |
| rR3P137 | 1 | HSDAVFTDNYTRLRKQMAAKKYLNSIKNER | 30 | 140 |
| rR3P138 | 1 | HSDAVFTDNYTRLRKQMAAKKYLNSIKNFR | 30 | 141 |
| rR3P139 | 1 | HSDAVFTDNYTRLRKQMAAKKYLNSIKNGR | 30 | 142 |
| rR3P140 | 1 | HSDAVFTDNYTRLRKQMAAKKYLNSIKNHR | 30 | 143 |
| rR3P141 | 1 | HSDAVFTDNYTRLRKQMAAKKYLNSIKNIR | 30 | 144 |
| rR3P142 | 1 | HSDAVFTDNYTRLRKQMAAKKYLNSIKNLR | 30 | 145 |
| rR3P143 | 1 | HSDAVFTDNYTRLRKQMAAKKYLNSIKNMR | 30 | 146 |

| | | | | |
|---|---|---|---|---|
| rR3P144 | 1 | HSDAVFTDNYTRLRKQMAAKKYLNSIKNNR | 30 | 147 |
| rR3P145 | 1 | HSDAVFTDNYTRLRKQMAAKKYLNSIKNPR | 30 | 148 |
| rR3P146 | 1 | HSDAVFTDNYTRLRKQMAAKKYLNSIKNQR | 30 | 149 |
| rR3P147 | 1 | HSDAVFTDNYTRLRKQMAAKKYLNSIKNRR | 30 | 150 |
| rR3P148 | 1 | HSDAVFTDNYTRLRKQMAAKKYLNSIKNSR | 30 | 151 |
| rR3P149 | 1 | HSDAVFTDNYTRLRKQMAAKKYLNSIKNTR | 30 | 152 |
| rR3P150 | 1 | HSDAVFTDNYTRLRKQMAAKKYLNSIKNVR | 30 | 153 |
| rR3P151 | 1 | HSDAVFTDNYTRLRKQMAAKKYLNSIKNWR | 30 | 154 |
| rR3P152 | 1 | HSDAVFTDNYTRLRKQMAAKKYLNSIKNYR | 30 | 155 |
| rR3P153 | 1 | HSDAVFTDNYTRLRKQMAAKKYLNSIKNKA | 30 | 156 |
| rR3P155 | 1 | HSDAVFTDNYTRLRKQMAAKKYLNSIKNKD | 30 | 157 |
| rR3P156 | 1 | HSDAVFTDNYTRLRKQMAAKKYLNSIKNKE | 30 | 158 |
| rR3P157 | 1 | HSDAVFTDNYTRLRKQMAAKKYLNSIKNKF | 30 | 159 |
| rR3P158 | 1 | HSDAVFTDNYTRLRKQMAAKKYLNSIKNKG | 30 | 160 |
| rR3P159 | 1 | HSDAVFTDNYTRLRKQMAAKKYLNSIKNKH | 30 | 161 |
| rR3P160 | 1 | HSDAVFTDNYTRLRKQMAAKKYLNSIKNKI | 30 | 162 |
| rR3P161 | 1 | HSDAVFTDNYTRLRKQMAAKKYLNSIKNKK | 30 | 163 |
| rR3P162 | 1 | HSDAVFTDNYTRLRKQMAAKKYLNSIKNKL | 30 | 164 |
| rR3P163 | 1 | HSDAVFTDNYTRLRKQMAAKKYLNSIKNKM | 30 | 165 |
| rR3P164 | 1 | HSDAVFTDNYTRLRKQMAAKKYLNSIKNKN | 30 | 166 |
| rR3P165 | 1 | HSDAVFTDNYTRLRKQMAAKKYLNSIKNKP | 30 | 167 |
| rR3P166 | 1 | HSDAVFTDNYTRLRKQMAAKKYLNSIKNKQ | 30 | 168 |
| rR3P167 | 1 | HSDAVFTDNYTRLRKQMAAKKYLNSIKNKS | 30 | 169 |
| rR3P168 | 1 | HSDAVFTDNYTRLRKQMAAKKYLNSIKNKT | 30 | 170 |
| rR3P169 | 1 | HSDAVFTDNYTRLRKQMAAKKYLNSIKNKV | 30 | 171 |
| rR3P170 | 1 | HSDAVFTDNYTRLRKQMAAKKYLNSIKNKW | 30 | 172 |
| rR3P171 | 1 | HSDAVFTDNYTRLRKQMAAKKYLNSIKNKY | 30 | 173 |
| R3P172 | 1 | HSDAVFTDNYTRLRKQVAAKKYLQSIKNKRYSWCEPGWCR | 39 | 174 |
| R3P173 | 1 | HSDAVFTDDYTRLRKEVAAKKYLESIKDKRY | 31 | 175 |
| rR3P174 | 1 | HSDAVFTDNYTRLRKQMAAKKYLNSIKNRI | 30 | 322 |
| rR3P175 | 1 | HSDAVFTDNYTRLRKQMAGKKYLNSIKNRI | 30 | 323 |
| rR3P176 | 1 | HSDAVFTDNYTRLRKQMAKKKYLNSIKNRI | 30 | 324 |
| rR3P177 | 1 | HSDAVFTDNYTRLRKQMARKKYLNSIKNRI | 30 | 325 |
| rR3P178 | 1 | HSDAVFTDNYTRLRKQMASKKYLNSIKNRI | 30 | 326 |
| rR3P179 | 1 | HSDAVFTDNYTRLRKQMAAKKYLNSIPNRI | 30 | 327 |
| rR3P180 | 1 | HSDAVFTDNYTRLRKQMAGKKYLNSIPNRI | 30 | 328 |
| rR3P181 | 1 | HSDAVFTDNYTRLRKQMAKKKYLNSIPNRI | 30 | 329 |
| rR3P182 | 1 | HSDAVFTDNYTRLRKQMARKKYLNSIPNRI | 30 | 330 |
| rR3P183 | 1 | HSDAVFTDNYTRLRKQMASKKYLNSIPNRI | 30 | 331 |
| rR3P184 | 1 | HSDAVFTDNYTRLRKQMAAKKYLNSIQNRI | 30 | 332 |
| rR3P185 | 1 | HSDAVFTDNYTRLRKQMAGKKYLNSIQNRI | 30 | 333 |
| rR3P186 | 1 | HSDAVFTDNYTRLRKQMAKKKYLNSIQNRI | 30 | 334 |
| rR3P187 | 1 | HSDAVFTDNYTRLRKQMARKKYLNSIQNRI | 30 | 335 |
| rR3P188 | 1 | HSDAVFTDNYTRLRKQMASKKYLNSIQNRI | 30 | 336 |
| rR3P189 | 1 | HSDAVFTDNYTRLRKQMAAKKYLNSIRNRI | 30 | 337 |
| rR3P190 | 1 | HSDAVFTDNYTRLRKQMAGKKYLNSIRNRI | 30 | 338 |
| rR3P191 | 1 | HSDAVFTDNYTRLRKQMAKKKYLNSIRNRI | 30 | 339 |
| rR3P192 | 1 | HSDAVFTDNYTRLRKQMARKKYLNSIRNRI | 30 | 340 |
| rR3P193 | 1 | HSDAVFTDNYTRLRKQMASKKYLNSIRNRI | 30 | 341 |
| PAC1 | 1 | ESDGIFTDSYSRYRKQMAVKKYLAAVL-NH$_2$ | 27 | 176 |
| PAC2 | 1 | HKDGIFTDSYSRYRKQMAVKKYLAAVL-NH$_2$ | 27 | 177 |
| PAC4 | 1 | HSDKIFTDSYSRYRKQMAVKKYLAAVL-NH$_2$ | 27 | 179 |
| PAC5 | 1 | HSDGKFTDSYSRYRKQMAVKKYLAAVL-NH$_2$ | 27 | 180 |
| PAC8 | 1 | HSDGIFTKSYSRYRKQMAVKKYLAAVL-NH$_2$ | 27 | 183 |
| PAC9 | 1 | HSDGIFTDKYSRYRKQMAVKKYLAAVL-NH$_2$ | 27 | 184 |
| PAC10 | 1 | HSDGIFTDSKSRYRKQMAVKKYLAAVL-NH$_2$ | 27 | 185 |
| PAC11 | 1 | HSDGIFTDSYKRYRKQMAVKKYLAAVL-NH$_2$ | 27 | 186 |
| PAC12 | 1 | HSDGIFTDSYSEYRKQMAVKKYLAAVL-NH$_2$ | 27 | 187 |
| PAC13 | 1 | HSDGIFTDSYSRKRKQMAVKKYLAAVL-NH$_2$ | 27 | 188 |

| | | | | |
|---|---|---|---|---|
| PAC14 | 1 | HSDGIFTDSYSRYEKQMAVKKYLAAVL-NH$_2$ | 27 | 189 |
| PAC15 | 1 | HSDGIFTDSYSRYREQMAVKKYLAAVL-NH$_2$ | 27 | 190 |
| PAC16 | 1 | HSDGIFTDSYSRYRKKMAVKKYLAAVL-NH$_2$ | 27 | 191 |
| PAC17 | 1 | HSDGIFTDSYSRYRKQKAVKKYLAAVL-NH$_2$ | 27 | 192 |
| PAC18 | 1 | HSDGIFTDSYSRYRKQMKVKKYLAAVL-NH$_2$ | 27 | 193 |
| PAC19 | 1 | HSDGIFTDSYSRYRKQMAKKKYLAAVL-NH$_2$ | 27 | 194 |
| PAC20 | 1 | HSDGIFTDSYSRYRKQMAVEKYLAAVL-NH$_2$ | 27 | 195 |
| PAC21 | 1 | HSDGIFTDSYSRYRKQMAVKEYLAAVL-NH$_2$ | 27 | 196 |
| PAC22 | 1 | HSDGIFTDSYSRYRKQMAVKKKLAAVL-NH$_2$ | 27 | 197 |
| PAC23 | 1 | HSDGIFTDSYSRYRKQMAVKKYKAAVL-NH$_2$ | 27 | 198 |
| PAC24 | 1 | HSDGIFTDSYSRYRKQMAVKKYLKAVL-NH$_2$ | 27 | 199 |
| PAC25 | 1 | HSDGIFTDSYSRYRKQMAVKKYLAKVL-NH$_2$ | 27 | 200 |
| PAC26 | 1 | HSDGIFTDSYSRYRKQMAVKKYLAAKL-NH$_2$ | 27 | 201 |
| PAC27 | 1 | HSDGIFTDSYSRYRKQMAVKKYLAAVK-NH$_2$ | 27 | 202 |

Figure 1

```
              10                  20                 30                    40
R3P3      H S D A V F T E N Y T K L R E Q L A A E K Y L N D L K K G G T
R3P12     H S D A V F T D N Y T R T R E Q L A A K K Y L N D I K E G G T
R3P13     H S D A V F T D N V T R L R E Q L A A K E T T N D I K K
VIP       H S D A V F T D N Y T R L R K Q M A V K K Y L N S I L N
PHGHP38   H S D G T F T D S Y S R Y R K Q M A V K K Y L A A V L G K R Y K Q R V K N K
GLP-1     H A E G T F T S D V S S Y L E G Q A A K E F I A W L V K G R
Exendin-4 H G E G T F T S D L S K Q M E E E A V R L F I E W L K N G G P S S G A P P P S
```

Fig. 2 rPACAP 27 (SEQ ID NO: 203)
GGATCCATCGAAGGTCGTCACTCCGATGGTATCTTCACCGACTCCTACTCGAGGTACCGCAA
GCAGATGGCTGTAAAGAAATATCTGGCTGCAGTTCTGTAATGACTCGAG rPACAP 38 (SEQ ID NO: 54)
GGATCCATCGAAGGTCGTCACTCCGATGGTATCTTCACCGACTCCTACTCGGTACCGCAA
GCAGATGGCTGTAAAGAAATATCTGGCTGCAGTCCTAGGCAAACGTTACAAGCAACGCGTTA
AAAACAAGTAATGACTCGAG rVIP (SEQ ID NO: 55)
GGATCCATCGAAGGTCGTCACTCCGACGCTGTTTTCACCGACAACTACACGCGTCTGCGTAA
ACAGATGGCTGTTAAGAAATACCTGAATTCCATCCTGAACTAATGACTCGAG rR3P3 (SEQ ID NO: 56)
GGATCCATCGAAGGTCGTCACTCCGATGCTGTTTTCACCGAAAACTACACCAAGCTTCGTAAA
CAGCTGGCAGCTAAGAAATACCTCAACGACCTGAAAAAGGGCGGTACCTAATGACTCGAG rR3P9 (SEQ ID NO: 204)
GGATCCATCGAAGGTCGTCACTCCGACGCTGTTTTCACCGACAACTACACGCGTCTGCGTAA
ACAGATGGCTGTTAAGAAATACCTGAATTCCATCAAGAAAGGCGGTACCTAATGACTCGAG rR3P12 (SEQ ID NO: 205)
GGATCCATCGAAGGTCGTCACTCCGACGCTGTTTTCACCGACAACTACACGCGTCTGCGTAA
ACAGCTGGCTGCTAAGAAATACCTGAACGACATCAAGAAGGTGGCACCTAATGACTCGAG rR3P33 (SEQ ID NO: 206)
GGATCCATCGAAGGTCGTCACTCCGACGCTGTTTTCACCGACAACTACACGCGTCTGCGTAA
ACAGCTGGCTGCTAAGAAATACCTGAACGACATCAAGAAATAATGAC rR3P41 (SEQ ID NO: 207)
GGATCCATCGAAGGTCGTCACTCCGACGCTGTTTTCACCGACAACTACACGCGTCTGCGTAA
ACAGATGGCTGTTAAGAAATACCTGAATTCCATCAAGAAATAATGACTCGAG rR3P42 (SEQ ID NO: 208)
GGATCCATCGAAGGTCGTCACTCCGACGCTGTTTTCACCGACAACTACACGCGTCTGCGTAA
ACAGATGGCTGTTAAGAAATACCTGAATTCCATCAAGAACTAATGACTCGAG rR3P43 (SEQ ID NO: 209)
GGATCCATCGAAGGTCGTCACTCCGACGCTGTTTTCACCGACAACTACACGCGTCTGCGTAA
ACAGATGGCTGTTAAGAAATACCTGAATTCCATCCTGAAATAATGACTCGAG rR3P44 (SEQ ID NO: 210)
GGATCCATCGAAGGTCGTCACTCCGACGCTGTTTTCACCGACAACTACACGGAACTGCGTAA
ACAGATGGCTGTTAAGAAATACCTGAATTCCATCCTGAACTAATGACTCGAG rR3P45 (SEQ ID NO: 211)
GGATCCATCGAAGGTCGTCACTCCGACGCTGTTTTCACCGACAACTACACGCGTCTGCGTGA
ACAGATGGCTGTTAAGAAATACCTGAATTCCATCCTGAACTAATGACTCGAG rR3P46 (SEQ ID NO: 212)
GGATCCATCGAAGGTCGTCACTCCGACGCTGTTTTCACCGACAACTACACGCGTCTGCGTAA
ACAGCTGGCTGTTAAGAAATACCTGAATTCCATCCTGAACTAATGACTCGAG rR3P47 (SEQ ID NO: 213)
GGATCCATCGAAGGTCGTCACTCCGACGCTGTTTTCACCGACAACTACACGCGTCTGCGTAA
ACAGATGGCTGCAAAGAAATACCTGAATTCCATCCTGAACTAATGACTCGAG rR3P48 (SEQ ID NO: 214)
GGATCCATCGAAGGTCGTCACTCCGACGCTGTTTTCACCGACAACTACACGCGTCTGCGTAA
ACAGATGGCTGTTAAGAAATACCTGAATGACATCCTGAACTAATGACTCGAG rR3P49 (SEQ ID NO: 215)
GGATCCATCGAAGGTCGTCACTCCGACGCTGTTTTCACCGACAACTACACGCGTCTGCGTAA
ACAGATGGCTGCAAAGAAATACCTGAATTCCATCAAGAACTAATGACTCGAG rR3P50 (SEQ ID NO: 216)
GGATCCATCGAAGGTCGTCACTCCGACGCTGTTTTCACCGACAACTACACGCGTCTGCGTAA
ACAGATGGCTGCAAAGAAATACCTGAATTCCATCCTGAAATAATGACTCGAG rR3P51 (SEQ ID NO: 217)
GGATCCATCGAAGGTCGTCACTCCGACGCTGTTTTCACCGACAACTACACGCGTCTGCGTAA
ACAGATGGCTGCAAAGAAATACCTGAATTCCATCAAGAAATAATGACTCGAG rR3P52 (SEQ ID NO: 218)
GGATCCATCGAAGGTCGTCACTCCGACGCTGTTTTCACCGACAACTACACGCGTCTGCGTAA
ACAGATGGCTGCAAAGAAATACCTGAATTCCATCAAGAAAAAGCGTTACTAATGACTCGAG rR3P53 (SEQ ID NO: 219)
GGATCCATCGAAGGTCGTCACTCCGACGCTGTTTTCACCGACAACTACACGCGTCTGCGTAA
ACAGATGGCTGCAAAGAAATACCTGAATTCCATCAAGAAAAAGCGTTAATGACTCGAG rR3P54 (SEQ ID NO: 220)
GGATCCATCGAAGGTCGTCACTCCGACGCTGTTTTCACCGACAACTACACGCGTCTGCGTAA
ACAGATGGCTGCAAAGAAATACCTGAATTCCATCAAGAAAAAGTAATGACTCGAG rR3P55 (SEQ ID NO: 221)
GGATCCATCGAAGGTCGTCACTCCGACGCTGTTTTCACCGACAACTACACGCGTCTGCGTAA
ACAGATGGCTGCAAAGAAATACCTGAATTCCATCAAGAACAAGCGTTACTAATGACTCGAG rR3P56 (SEQ ID NO: 222)
GGATCCATCGAAGGTCGTCACTCCGACGCTGTTTTCACCGACAACTACACGCGTCTGCGTAA
ACAGATGGCTGTTAAGAAATACCTGAATTCCATCAAGAAAAAGCGTTACTAATGACTCGAG rR3P57 (SEQ ID NO: 223)
GGATCCATCGAAGGTCGTCACTCCGACGCTGTTTTCACCGACAACTACACGCGTCTGCGTAA
ACAGATGGCTGTTAAGAAATACCTGAATTCCATCAAGAAAAAGCGTTAATGACTCGAG rR3P58 (SEQ ID NO: 224)
GGATCCATCGAAGGTCGTCACTCCGACGCTGTTTTCACCGACAACTACACGCGTCTGCGTAA
ACAGATGGCTGTTAAGAAATACCTGAATTCCATCAAGAAAAAGTAATGACTCGAG rR3P59 (SEQ ID NO: 225)
GGATCCATCGAAGGTCGTCACTCCGACGCTGTTTTCACCGACAACTACACGCGTCTGCGTAA
ACAGATGGCTGTTAAGAAATACCTGAATTCCATCAAGAACAAGCGTTACTAATGACTCGAG rR3P60 (SEQ ID NO: 226)
GGATCCATCGAAGGTCGTCACTCCGACGCTGTTTTCACCGACAACTACACGCGCTTAAGAAA
ACAGGTTGCTGCAAAGAAATACCTGCAGTCCATCAAGAAATAATGACTCGAG rR3P61 (SEQ ID NO: 227)

GGATCCATCGAAGGTCGTCACTCCGACGCTGTTTTCACCGACAACTACACGCGCTTAAGAAA
ACAGATCGCTGCAAAGAAATACCTGCAGACTATCAAGAAATAATGACTCGAG rR3P62 (SEQ ID NO: 228)
GGATCCATCGAAGGTCGTCACTCCGACGCTGTTTTCACCGACAACTACACGCGCTTAAGAAA
ACAGGTTGCTGCAAAGAAATACCTGAATTCCATCAAGAAATAATGACTCGAG rR3P65 (SEQ ID NO: 229)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGCGTTAATGAGAATTC rR3P71 (SEQ ID NO: 230)
GGATCCATCGAAGGTCGTCACTCCGACGCTGTTTTCACCGACCAGTACACGCGCTTAAGAAA
ACAGATGGCTGCAAAGAAATACCTGAATTCCATCAAGAACAAGCGTTACTAATGACTCGAG rR3P98 (SEQ ID NO: 231)
GGATCCATCGAAGGTCGTCACTCCGACGCTGTTTTCACCGACAACTACACGCGCTTAAGAAA
ACAGATGGCTGACAAGAAATACCTGAACTCCATCAAGAACAAGCGTTAATGAGAATTC rR3P99 (SEQ ID NO: 232)
GGATCCATCGAAGGTCGTCACTCCGACGCTGTTTTCACCGACAACTACACGCGCTTAAGAAA
ACAGATGGCTGAGAAGAAATACCTGAACTCCATCAAGAACAAGCGTTAATGAGAATTC rR3P100 (SEQ ID NO: 233)
GGATCCATCGAAGGTCGTCACTCCGACGCTGTTTTCACCGACAACTACACGCGCTTAAGAAA
ACAGATGGCTTTCAAGAAATACCTGAACTCCATCAAGAACAAGCGTTAATGAGAATTC rR3P101 (SEQ ID NO: 234)
GGATCCATCGAAGGTCGTCACTCCGACGCTGTTTTCACCGACAACTACACGCGCTTAAGAAA
ACAGATGGCTGGCAAGAAATACCTGAACTCCATCAAGAACAAGCGTTAATGAGAATTC rR3P102 (SEQ ID NO: 235)
GGATCCATCGAAGGTCGTCACTCCGACGCTGTTTTCACCGACAACTACACGCGCTTAAGAAA
ACAGATGGCTCACAAGAAATACCTGAACTCCATCAAGAACAAGCGTTAATGAGAATTC rR3P103 (SEQ ID NO: 236)
GGATCCATCGAAGGTCGTCACTCCGACGCTGTTTTCACCGACAACTACACGCGCTTAAGAAA
ACAGATGGCTATCAAGAAATACCTGAACTCCATCAAGAACAAGCGTTAATGAGAATTC rR3P104 (SEQ ID NO: 237)
GGATCCATCGAAGGTCGTCACTCCGACGCTGTTTTCACCGACAACTACACGCGCTTAAGAAA
ACAGATGGCTAAAAAGAAATACCTGAACTCCATCAAGAACAAGCGTTAATGAGAATTC rR3P105 (SEQ ID NO: 238)
GGATCCATCGAAGGTCGTCACTCCGACGCTGTTTTCACCGACAACTACACGCGCTTAAGAAA
ACAGATGGCTCTGAAGAAATACCTGAACTCCATCAAGAACAAGCGTTAATGAGAATTC rR3P106 (SEQ ID NO: 239)
GGATCCATCGAAGGTCGTCACTCCGACGCTGTTTTCACCGACAACTACACGCGCTTAAGAAA
ACAGATGGCTATGAAGAAATACCTGAACTCCATCAAGAACAAGCGTTAATGAGAATTC rR3P107 (SEQ ID NO: 240)
GGATCCATCGAAGGTCGTCACTCCGACGCTGTTTTCACCGACAACTACACGCGCTTAAGAAA
ACAGATGGCTAACAAGAAATACCTGAACTCCATCAAGAACAAGCGTTAATGAGAATTC rR3P108 (SEQ ID NO: 241)
GGATCCATCGAAGGTCGTCACTCCGACGCTGTTTTCACCGACAACTACACGCGCTTAAGAAA
ACAGATGGCTCCGAAGAAATACCTGAACTCCATCAAGAACAAGCGTTAATGAGAATTC rR3P109 (SEQ ID NO: 242)
GGATCCATCGAAGGTCGTCACTCCGACGCTGTTTTCACCGACAACTACACGCGCTTAAGAAA
ACAGATGGCTCAGAAGAAATACCTGAACTCCATCAAGAACAAGCGTTAATGAGAATTC rR3P110 (SEQ ID NO: 243)
GGATCCATCGAAGGTCGTCACTCCGACGCTGTTTTCACCGACAACTACACGCGCTTAAGAAA
ACAGATGGCTCGCAAGAAATACCTGAACTCCATCAAGAACAAGCGTTAATGAGAATTC rR3P111 (SEQ ID NO: 244)
GGATCCATCGAAGGTCGTCACTCCGACGCTGTTTTCACCGACAACTACACGCGCTTAAGAAA
ACAGATGGCTTCCAAGAAATACCTGAACTCCATCAAGAACAAGCGTTAATGAGAATTC rR3P112 (SEQ ID NO: 245)
GGATCCATCGAAGGTCGTCACTCCGACGCTGTTTTCACCGACAACTACACGCGCTTAAGAAA
ACAGATGGCTACCAAGAAATACCTGAACTCCATCAAGAACAAGCGTTAATGAGAATTC rR3P113 (SEQ ID NO: 246)
GGATCCATCGAAGGTCGTCACTCCGACGCTGTTTTCACCGACAACTACACGCGCTTAAGAAA
ACAGATGGCTGTGAAGAAATACCTGAACTCCATCAAGAACAAGCGTTAATGAGAATTC rR3P114 (SEQ ID NO: 247)
GGATCCATCGAAGGTCGTCACTCCGACGCTGTTTTCACCGACAACTACACGCGCTTAAGAAA
ACAGATGGCTTGGAAGAAATACCTGAACTCCATCAAGAACAAGCGTTAATGAGAATTC rR3P115 (SEQ ID NO: 248)
GGATCCATCGAAGGTCGTCACTCCGACGCTGTTTTCACCGACAACTACACGCGCTTAAGAAA
ACAGATGGCTTACAAGAAATACCTGAACTCCATCAAGAACAAGCGTTAATGAGAATTC rR3P116 (SEQ ID NO: 249)
GGATCCATCGAAGGTCGTCACTCCGACGCTGTTTTCACCGACAACTACACGCGTCTGCGTAA
ACAGATGGCTGCAAAGAAATACCTGAACTCCATCGCGAACAAGCGTTAATGAGAATTC rR3P118 (SEQ ID NO: 250)
GGATCCATCGAAGGTCGTCACTCCGACGCTGTTTTCACCGACAACTACACGCGTCTGCGTAA
ACAGATGGCTGCAAAGAAATACCTGAACTCCATCGACAACAAGCGTTAATGAGAATTC rR3P119 (SEQ ID NO: 251)
GGATCCATCGAAGGTCGTCACTCCGACGCTGTTTTCACCGACAACTACACGCGTCTGCGTAA
ACAGATGGCTGCAAAGAAATACCTGAACTCCATCGAGAACAAGCGTTAATGAGAATTC rR3P120 (SEQ ID NO: 252)
GGATCCATCGAAGGTCGTCACTCCGACGCTGTTTTCACCGACAACTACACGCGTCTGCGTAA
ACAGATGGCTGCAAAGAAATACCTGAACTCCATCTTCAACAAGCGTTAATGAGAATTC rR3P121 (SEQ ID NO: 253)
GGATCCATCGAAGGTCGTCACTCCGACGCTGTTTTCACCGACAACTACACGCGTCTGCGTAA
ACAGATGGCTGCAAAGAAATACCTGAACTCCATCGGCAACAAGCGTTAA:GAGAATTC rR3P122 (SEQ ID NO: 254)
GGATCCATCGAAGGTCGTCACTCCGACGCTGTTTTCACCGACAACTACACGCGTCTGCGTAA
ACAGATGGCTGCAAAGAAATACCTGAACTCCATCGGCAACAAGCGTTAATGAGAATTC rR3P123 (SEQ ID NO: 255)
GGATCCATCGAAGGTCGTCACTCCGACGCTGTTTTCACCGACAACTACACGCGTCTGCGTAA
ACAGATGGCTGCAAAGAAATACCTGAACTCCATCATCAACAAGCGTTAATGAGAATTC rR3P124 (SEQ ID NO: 256)
GGATCCATCGAAGGTCGTCACTCCGACGCTGTTTTCACCGACAACTACACGCGTCTGCGTAA
ACAGATGGCTGCAAAGAAATACCTGAACTCCATCATGAACAAGCGTTAATGAGAATTC rR3P125 (SEQ ID NO: 257)
GGATCCATCGAAGGTCGTCACTCCGACGCTGTTTTCACCGACAACTACACGCGTCTGCGTAA
ACAGATGGCTGCAAAGAAATACCTGAACTCCATCAACAACAAGCGTTAATGAGAATTC rR3P126 (SEQ ID NO: 258)
GGATCCATCGAAGGTCGTCACTCCGACGCTGTTTTCACCGACAACTACACGCGTCTGCGTAA
ACAGATGGCTGCAAAGAAATACCTGAACTCCATCCCGAACAAGCGTTAATGAGAATTC rR3P127 (SEQ ID NO: 259)
GGATCCATCGAAGGTCGTCACTCCGACGCTGTTTTCACCGACAACTACACGCGTCTGCGTAA
ACAGATGGCTGCAAAGAAATACCTGAACTCCATCCAGAACAAGCGTTAATGAGAATTC rR3P128 (SEQ ID NO: 260)
GGATCCATCGAAGGTCGTCACTCCGACGCTGTTTTCACCGACAACTACACGCGTCTGCGTAA
ACAGATGGCTGCAAAGAAATACCTGAACTCCATCAGGAACAAGCGTTAATGAGAATTC rR3P129 (SEQ ID NO: 261)
GGATCCATCGAAGGTCGTCACTCCGACGCTGTTTTCACCGACAACTACACGCGTCTGCGTAA
ACAGATGGCTGCAAAGAAATACCTGAACTCCATCAGCAACAAGCGTTAATGAGAATTC rR3P130 (SEQ ID NO: 262)
GGATCCATCGAAGGTCGTCACTCCGACGCTGTTTTCACCGACAACTACACGCGTCTGCGTAA
ACAGATGGCTGCAAAGAAATACCTGAACTCCATCACGAACAAGCGTTAATGAGAATTC rR3P131 (SEQ ID NO: 263)
GGATCCATCGAAGGTCGTCACTCCGACGCTGTTTTCACCGACAACTACACGCGTCTGCGTAA
ACAGATGGCTGCAAAGAAATACCTGAACTCCATCGTGAACAAGCGTTAATGAGAATTC rR3P132 (SEQ ID NO: 264)
GGATCCATCGAAGGTCGTCACTCCGACGCTGTTTTCACCGACAACTACACGCGTCTGCGTAA
ACAGATGGCTGCAAAGAAATACCTGAACTCCATCTGGAACAAGCGTTAATGAGAATTC rR3P133 (SEQ ID NO: 265)
GGATCCATCGAAGGTCGTCACTCCGACGCTGTTTTCACCGACAACTACACGCGTCTGCGTAA
ACAGATGGCTGCAAAGAAATACCTGAACTCCATCTACAACAAGCGTTAATGAGAATTC rR3P134 (SEQ ID NO: 266)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACGCGCGTTAATGAGAATTC rR3P136 (SEQ ID NO: 267)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACGACCGTTAATGAGAATTC rR3P137 (SEQ ID NO: 268)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACGAACGTTAATGAGAATTC rR3P138 (SEQ ID NO: 269)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACTTCCGTTAATGAGAATTC rR3P139 (SEQ ID NO: 270)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACGGCCGTTAATGAGAATTC rR3P140 (SEQ ID NO: 271)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACCACCGTTAATGAGAATTC rR3P141 (SEQ ID NO: 272)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACATCCGTTAATGAGAATTC rR3P142 (SEQ ID NO: 273)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACCTGCGTTAATGAGAATTC rR3P143 (SEQ ID NO: 274)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACATGCGTTAATGAGAATTC rR3P144 (SEQ ID NO: 275)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAACCGTTAATGAGAATTC rR3P145 (SEQ ID NO: 276)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACCCGCGTTAATGAGAATTC rR3P146 (SEQ ID NO: 277)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACCAGCGTTAATGAGAATTC rR3P147 (SEQ ID NO: 278)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACCGCCGTTAATGAGAATTC rR3P148 (SEQ ID NO: 279)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAGCCGTTAATGAGAATTC rR3P149 (SEQ ID NO: 280)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACACCCGTTAATGAGAATTC rR3P150 (SEQ ID NO: 281)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACGTGCGTTAATGAGAATTC rR3P151 (SEQ ID NO: 282)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACTGGCGTTAATGAGAATTC rR3P152 (SEQ ID NO: 283)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACTACCGTTAATGAGAATTC rR3P153 (SEQ ID NO: 284)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGGCGTAATGAGAATTC rR3P155 (SEQ ID NO: 285)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGGACTAATGAGAATTC rR3P156 (SEQ ID NO: 286)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGGAGTAATGAGAATTC rR3P157 (SEQ ID NO: 287)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGTTCTAATGAGAATTC rR3P158 (SEQ ID NO: 288)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGGGCTAATGAGAATTC rR3P159 (SEQ ID NO: 289)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGCACTAATGAGAATTC rR3P160 (SEQ ID NO: 290)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGATCTAATGAGAATTC rR3P161 (SEQ ID NO: 291)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGAAGTAATGAGAATTC rR3P162 (SEQ ID NO: 292)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGCTGTAATGAGAATTC rR3P163 (SEQ ID NO: 293)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGATGTAATGAGAATTC rR3P164 (SEQ ID NO: 294)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGAACTAATGAGAATTC rR3P165 (SEQ ID NO: 295)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGCCGTAATGAGAATTC rR3P166 (SEQ ID NO: 296)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGCAGTAATGAGAATTC rR3P167 (SEQ ID NO: 297)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGAGCTAATGAGAATTC rR3P168 (SEQ ID NO: 298)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGACCTAATGAGAATTC rR3P169 (SEQ ID NO: 299)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGGTGTAATGAGAATTC rR3P170 (SEQ ID NO: 300)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGTGGTAATGAGAATTC rR3P171 (SEQ ID NO: 301)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACAAGTACTAATGAGAATTC rR3P174 (SEQ ID NO: 302)
GGATCCATCGAAGGTCGTCACTCCGACGCTGTTTTCACCGACAACTACACGCGTCTGCGTAA
ACAGATGGCTGCAAAGAAATACCTGAACTCCATCAAGAACCGTATCTAATGAGAATTC rR3P175 (SEQ ID NO: 303)
GGATCCATCGAAGGTCGTCACTCCGACGCTGTTTTCACCGACAACTACACGCGTCTGCGTAA
ACAGATGGCTGGCAAGAAATACCTGAACTCCATCAAGAACCGTATCTAATGAGAATTC rR3P176 (SEQ ID NO: 304)
GGATCCATCGAAGGTCGTCACTCCGACGCTGTTTTCACCGACAACTACACGCGTCTGCGTAA
ACAGATGGCTaaaAAGAAATACCTGAACTCCATCAAGAACCGTATCTAATGAGAATTC rR3P177 (SEQ ID NO: 305)
GGATCCATCGAAGGTCGTCACTCCGACGCTGTTTTCACCGACAACTACACGCGTCTGCGTAA
ACAGATGGCTcgcAAGAAATACCTGAACTCCATCAAGAACCGTATCTAATGAGAATTC rR3P178 (SEQ ID NO: 306)
GGATCCATCGAAGGTCGTCACTCCGACGCTGTTTTCACCGACAACTACACGCGTCTGCGTAA
ACAGATGGCTtccAAGAAATACCTGAACTCCATCAAGAACCGTATCTAATGAGAATTC rR3P179 (SEQ ID NO: 307)
GGATCCATCGAAGGTCGTCACTCCGACGCTGTTTTCACCGACAACTACACGCGTCTGCGTAA
ACAGATGGCTGCAAAGAAATACCTGAACTCCATCccgAACCGTATCTAATGAGAATTC rR3P180 (SEQ ID NO: 308)
GGATCCATCGAAGGTCGTCACTCCGACGCTGTTTTCACCGACAACTACACGCGTCTGCGTAA
ACAGATGGCTggcAAGAAATACCTGAACTCCATCccgAACCGTATCTAATGAGAATTC rR3P181 (SEQ ID NO: 309)
GGATCCATCGAAGGTCGTCACTCCGACGCTGTTTTCACCGACAACTACACGCGTCTGCGTAA
ACAGATGGCTaaaAAGAAATACCTGAACTCCATCccgAACCGTATCTAATGAGAATTC rR3P182 (SEQ ID NO: 310)
GGATCCATCGAAGGTCGTCACTCCGACGCTGTTTTCACCGACAACTACACGCGTCTGCGTAA
ACAGATGGCTcgcAAGAAATACCTGAACTCCATCccgAACCGTATCTAATGAGAATTC rR3P183 (SEQ ID NO: 311)
GGATCCATCGAAGGTCGTCACTCCGACGCTGTTTTCACCGACAACTACACGCGTCTGCGTAA
ACAGATGGCTtccAAGAAATACCTGAACTCCATCccgAACCGTATCTAATGAGAATTC rR3P184 (SEQ ID NO: 312)
GGATCCATCGAAGGTCGTCACTCCGACGCTGTTTTCACCGACAACTACACGCGTCTGCGTAA
ACAGATGGCTGCAAAGAAATACCTGAACTCCATCcagAACCGTATCTAATGAGAATTC rR3P185 (SEQ ID NO: 313)
GGATCCATCGAAGGTCGTCACTCCGACGCTGTTTTCACCGACAACTACACGCGTCTGCGTAA
ACAGATGGCTggcAAGAAATACCTGAACTCCATCcagAACCGTATCTAATGAGAATTC rR3P186 (SEQ ID NO: 314)
GGATCCATCGAAGGTCGTCACTCCGACGCTGTTTTCACCGACAACTACACGCGTCTGCGTAA
ACAGATGGCTaaaAAGAAATACCTGAACTCCATCcagAACCGTATCTAATGAGAATTC rR3P187 (SEQ ID NO: 315)
GGATCCATCGAAGGTCGTCACTCCGACGCTGTTTTCACCGACAACTACACGCGTCTGCGTAA
ACAGATGGCTcgcAAGAAATACCTGAACTCCATCcagAACCGTATCTAATGAGAATTC rR3P188 (SEQ ID NO: 316)
GGATCCATCGAAGGTCGTCACTCCGACGCTGTTTTCACCGACAACTACACGCGTCTGCGTAA
ACAGATGGCTtccAAGAAATACCTGAACTCCATCcagAACCGTATCTAATGAGAATTC rR3P189 (SEQ ID NO: 317)
GGATCCATCGAAGGTCGTCACTCCGACGCTGTTTTCACCGACAACTACACGCGTCTGCGTAA
ACAGATGGCTGCAAAGAAATACCTGAACTCCATCcgtAACCGTATCTAATGAGAATTC rR3P190 (SEQ ID NO: 318)
GGATCCATCGAAGGTCGTCACTCCGACGCTGTTTTCACCGACAACTACACGCGTCTGCGTAA
ACAGATGGCTggcAAGAAATACCTGAACTCCATCcgtAACCGTATCTAATGAGAATTC rR3P191 (SEQ ID NO: 319)
GGATCCATCGAAGGTCGTCACTCCGACGCTGTTTTCACCGACAACTACACGCGTCTGCGTAA
ACAGATGGCTaaaAAGAAATACCTGAACTCCATCcgtAACCGTATCTAATGAGAATTC rR3P192 (SEQ ID NO: 320)
GGATCCATCGAAGGTCGTCACTCCGACGCTGTTTTCACCGACAACTACACGCGTCTGCGTAA
ACAGATGGCTcgcAAGAAATACCTGAACTCCATCcgtAACCGTATCTAATGAGAATTC rR3P193 (SEQ ID NO: 321)
GGATCCATCGAAGGTCGTCACTCCGACGCTGTTTTCACCGACAACTACACGCGTCTGCGTAA
ACAGATGGCTtccAAGAAATACCTGAACTCCATCcgtAACCGTATCTAATGAGAATTC

Figure 8

SEQUENCE LISTING

```
<160> NUMBER OF SEQ ID NOS: 343

<210> SEQ ID NO 1
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (28)..(28)
<223> OTHER INFORMATION: AMIDATION

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 38
<212> TYPE: PRT
```

```
<213> ORGANISM: Artificial
<220> FEATURE:
<223> OTHER INFORMATION: Synthetic Construct
<220> FEATURE:
<221> NAME/KEY: MOD_RES
<222> LOCATION: (38)..(38)
<223> OTHER INFORMATION: AMIDATION

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 3
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (30)..(30)
<223> OTHER INFORMATION: AMIDATION

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 39
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (39)..(39)
<223> OTHER INFORMATION: AMIDATION

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: Nle
<220> FEATURE:
<221> NAME/KEY: MOD_RES
```

```
<222> LOCATION: (31)..(31)
<223> OTHER INFORMATION: AMIDATION

<400> SEQUENCE: 5

His Ser Asp Ala Val Phe Thr Glu Asn Tyr Thr Lys Leu Arg Lys Gln
1               5                   10                  15

Xaa Ala Ala Lys Lys Tyr Leu Asn Asp Leu Lys Lys Gly Gly Thr
            20                  25                  30

<210> SEQ ID NO 6
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (31)..(31)
<223> OTHER INFORMATION: AMIDATION

<400> SEQUENCE: 6

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr
            20                  25                  30

<210> SEQ ID NO 7
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 7

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr
            20                  25                  30

<210> SEQ ID NO 8
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 8

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr
            20                  25                  30

<210> SEQ ID NO 9
<211> LENGTH: 28
<212> TYPE: PRT
<213> ORGANISM: Artificial
```

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: Xaa is methoxy-Tyr
<220> FEATURE:
<221> NAME/KEY: MISC_FEATURE
<222> LOCATION: (17)..(17)
<223> OTHER INFORMATION: Nle
<220> FEATURE:
<221> NAME/KEY: MOD_RES
<222> LOCATION: (28)..(28)
<223> OTHER INFORMATION: AMIDATION

<400> SEQUENCE: 9

His Ser Asp Ala Val Phe Thr Glu Asn Xaa Thr Lys Leu Arg Lys Gln
1               5                   10                  15

Xaa Ala Ala Lys Lys Tyr Leu Asn Asp Leu Lys Lys
            20                  25

<210> SEQ ID NO 10
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 10

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys
            20                  25

<210> SEQ ID NO 11
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (28)..(28)
<223> OTHER INFORMATION: AMIDATION

<400> SEQUENCE: 11

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys
            20                  25

<210> SEQ ID NO 12
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 12
```

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys Gly Gly Thr
            20                  25                  30

<210> SEQ ID NO 13
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 13

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Leu Asn Gly Gly Thr
            20                  25                  30

<210> SEQ ID NO 14
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 14

His Ser Asp Ala Val Phe Thr Asp Asn Tyr Thr Lys Leu Arg Lys Gln
1               5                   10                  15

Leu Ala Ala Lys Lys Tyr Leu Asn Asp Ile Leu Asn Gly Gly Thr
            20                  25                  30

<210> SEQ ID NO 15
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 15

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gly Gly Thr
            20                  25                  30

<210> SEQ ID NO 16
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (28)..(28)
<223> OTHER INFORMATION: AMIDATION

<400> SEQUENCE: 16

His Ser Asp Ala Val Phe Thr Asp Asn Tyr Thr Arg Leu Arg Lys Gln
1               5                   10                  15

```
Leu Ala Ala Lys Lys Tyr Leu Asn Asp Ile Lys Lys
            20                  25
```

<210> SEQ ID NO 17
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 17

```
His Ser Asp Ala Val Phe Thr Asp Asn Tyr Thr Arg Leu Arg Lys Gln
1               5                   10                  15

Met Ala Val Lys Lys Tyr Leu Asn Asp Leu Lys Lys Gly Gly Thr
            20                  25                  30
```

<210> SEQ ID NO 18
<211> LENGTH: 40
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 18

```
His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr Ser
            20                  25                  30

Trp Cys Glu Pro Gly Trp Cys Arg
        35                  40
```

<210> SEQ ID NO 19
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 19

```
His Ser Asp Ala Val Phe Thr Asp Asn Tyr Thr Arg Leu Arg Lys Gln
1               5                   10                  15

Met Ala Ala Lys Lys Tyr Leu Asn Asp Ile Lys Lys Gly Gly Thr
            20                  25                  30
```

<210> SEQ ID NO 20
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 20

```
His Ser Asp Ala Val Phe Thr Asp Asn Tyr Thr Arg Leu Arg Lys Gln
1               5                   10                  15
```

-continued

Leu Ala Val Lys Lys Tyr Leu Asn Asp Ile Lys Lys Gly Gly Thr
            20                  25                  30

<210> SEQ ID NO 21
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 21

His Ser Asp Ala Val Phe Thr Asp Asn Tyr Thr Arg Leu Arg Lys Gln
1               5                  10                  15

Leu Ala Ala Lys Lys Tyr Leu Asn Ser Ile Lys Lys Gly Gly Thr
            20                  25                  30

<210> SEQ ID NO 22
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 22

His Ser Asp Ala Val Phe Thr Asp Asn Tyr Thr Arg Leu Arg Lys Gln
1               5                  10                  15

Leu Ala Ala Lys Lys Tyr Leu Asn Asp Ile Lys Asn Gly Gly Thr
            20                  25                  30

<210> SEQ ID NO 23
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 23

His Ser Asp Ala Val Phe Thr Asp Asn Tyr Thr Arg Leu Arg Lys Gln
1               5                  10                  15

Leu Ala Val Lys Lys Tyr Leu Asn Ser Ile Lys Lys Gly Gly Thr
            20                  25                  30

<210> SEQ ID NO 24
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 24

His Ser Asp Ala Val Phe Thr Asp Asn Tyr Thr Arg Leu Arg Lys Gln
1               5                  10                  15

Met Ala Ala Lys Lys Tyr Leu Asn Ser Ile Lys Lys Gly Gly Thr
            20                  25                  30

```
<210> SEQ ID NO 25
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 25

His Ser Asp Ala Val Phe Thr Asp Asn Tyr Thr Arg Leu Arg Lys Gln
1               5                   10                  15

Leu Ala Val Lys Lys Tyr Leu Asn Asp Ile Lys Asn Gly Gly Thr
            20                  25                  30

<210> SEQ ID NO 26
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 26

His Ser Asp Ala Val Phe Thr Asp Asn Tyr Thr Arg Leu Arg Lys Gln
1               5                   10                  15

Leu Ala Ala Lys Lys Tyr Leu Asn Ser Ile Lys Asn Gly Gly Thr
            20                  25                  30

<210> SEQ ID NO 27
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 27

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gly Gly
            20                  25                  30

<210> SEQ ID NO 28
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 28

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gly
            20                  25

<210> SEQ ID NO 29
```

```
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 29
```

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys
            20                  25

```
<210> SEQ ID NO 30
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 30
```

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gln
            20                  25

```
<210> SEQ ID NO 31
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 31
```

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Asn Gln
            20                  25                  30

```
<210> SEQ ID NO 32
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 32
```

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Lys Arg Tyr
            20                  25                  30

```
<210> SEQ ID NO 33
<211> LENGTH: 28
<212> TYPE: PRT
<213> ORGANISM: Artificial
```

```
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 33

His Ser Asp Ala Val Phe Thr Asp Asn Tyr Thr Arg Leu Arg Lys Gln
 1               5                  10                  15

Met Ala Val Lys Lys Tyr Leu Asn Ser Ile Lys Lys
            20                  25

<210> SEQ ID NO 34
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 34

His Ser Asp Ala Val Phe Thr Asp Asn Tyr Thr Arg Leu Arg Lys Gln
 1               5                  10                  15

Met Ala Val Lys Lys Tyr Leu Asn Ser Ile Lys Asn
            20                  25

<210> SEQ ID NO 35
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 35

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Lys
            20                  25

<210> SEQ ID NO 36
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 36

His Ser Asp Ala Val Phe Thr Asp Asn Tyr Thr Glu Leu Arg Lys Gln
 1               5                  10                  15

Met Ala Val Lys Lys Tyr Leu Asn Ser Ile Leu Asn
            20                  25

<210> SEQ ID NO 37
<211> LENGTH: 28
<212> TYPE: PRT
<213> ORGANISM: Artificial
<220> FEATURE:
<223> OTHER INFORMATION: Synthetic Construct
<220> FEATURE:
```

```
<221> NAME/KEY: PEPTIDE
<222> LOCATION: (1)..(28)

<400> SEQUENCE: 37

His Ser Asp Ala Val Phe Thr Asp Asn Tyr Thr Arg Leu Arg Glu Gln
1               5                   10                  15

Met Ala Val Lys Lys Tyr Leu Asn Ser Ile Leu Asn
            20                  25

<210> SEQ ID NO 38
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 38

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
            20                  25

<210> SEQ ID NO 39
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 39

His Ser Asp Ala Val Phe Thr Asp Asn Tyr Thr Arg Leu Arg Lys Gln
1               5                   10                  15

Met Ala Ala Lys Lys Tyr Leu Asn Ser Ile Leu Asn
            20                  25

<210> SEQ ID NO 40
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 40

His Ser Asp Ala Val Phe Thr Asp Asn Tyr Thr Arg Leu Arg Lys Gln
1               5                   10                  15

Met Ala Val Lys Lys Tyr Leu Asn Asp Ile Leu Asn
            20                  25

<210> SEQ ID NO 41
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)
```

-continued

<400> SEQUENCE: 41

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn
            20                  25

<210> SEQ ID NO 42
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 42

His Ser Asp Ala Val Phe Thr Asp Asn Tyr Thr Arg Leu Arg Lys Gln
1               5                   10                  15

Met Ala Ala Lys Lys Tyr Leu Asn Ser Ile Leu Lys
            20                  25

<210> SEQ ID NO 43
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 43

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys
            20                  25

<210> SEQ ID NO 44
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 44

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Lys Arg Tyr
            20                  25                  30

<210> SEQ ID NO 45
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 45

His Ser Asp Ala Val Phe Thr Asp Asn Tyr Thr Arg Leu Arg Lys Gln

```
          1               5                  10                 15
Met Ala Ala Lys Lys Tyr Leu Asn Ser Ile Lys Lys Arg
            20                 25                 30

<210> SEQ ID NO 46
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 46

His Ser Asp Ala Val Phe Thr Asp Asn Tyr Thr Arg Leu Arg Lys Gln
  1               5                  10                 15
Met Ala Ala Lys Lys Tyr Leu Asn Ser Ile Lys Lys Lys
            20                 25

<210> SEQ ID NO 47
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 47

His Ser Asp Ala Val Phe Thr Asp Asn Tyr Thr Arg Leu Arg Lys Gln
  1               5                  10                 15
Met Ala Ala Lys Lys Tyr Leu Asn Ser Ile Lys Asn Lys Arg Tyr
            20                 25                 30

<210> SEQ ID NO 48
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 48

His Ser Asp Ala Val Phe Thr Asp Asn Tyr Thr Arg Leu Arg Lys Gln
  1               5                  10                 15
Met Ala Val Lys Lys Tyr Leu Asn Ser Ile Lys Lys Lys Arg Tyr
            20                 25                 30

<210> SEQ ID NO 49
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 49

His Ser Asp Ala Val Phe Thr Asp Asn Tyr Thr Arg Leu Arg Lys Gln
  1               5                  10                 15
Met Ala Val Lys Lys Tyr Leu Asn Ser Ile Lys Lys Lys Arg
```

```
                    20                  25                  30
```

<210> SEQ ID NO 50
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 50

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys Lys
            20                  25
```

<210> SEQ ID NO 51
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 51

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Asn Lys Arg Tyr
            20                  25                  30
```

<210> SEQ ID NO 52
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 52

```
His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Lys
            20                  25
```

<210> SEQ ID NO 53
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 53

```
His Ser Asp Ala Val Phe Thr Asp Asn Tyr Thr Arg Leu Arg Lys Gln
1               5                   10                  15

Ile Ala Ala Lys Lys Tyr Leu Gln Thr Ile Lys Lys
            20                  25
```

```
<210> SEQ ID NO 54
<211> LENGTH: 144
<212> TYPE: DNA
<213> ORGANISM: Artificial
<220> FEATURE:
<223> OTHER INFORMATION: Synthetic Construct

<400> SEQUENCE: 54
ggatccatcg aaggtcgtca ctccgatggt atcttcaccg actcctactc tcggtaccgc      60
aagcagatgg ctgtaaagaa atatctggct gcagtcctag gcaaacgtta caagcaacgc     120
gttaaaaaca gtaatgact cgag                                             144

<210> SEQ ID NO 55
<211> LENGTH: 114
<212> TYPE: DNA
<213> ORGANISM: Artificial
<220> FEATURE:
<223> OTHER INFORMATION: Synthetic Construct

<400> SEQUENCE: 55
ggatccatcg aaggtcgtca ctccgacgct gttttcaccg acaactacac gcgtctgcgt      60
aaacagatgg ctgttaagaa atacctgaat tccatcctga ctaatgact cgag            114

<210> SEQ ID NO 56
<211> LENGTH: 123
<212> TYPE: DNA
<213> ORGANISM: Artificial
<220> FEATURE:
<223> OTHER INFORMATION: Synthetic Construct

<400> SEQUENCE: 56
ggatccatcg aaggtcgtca ctccgatgct gttttcaccg aaaactacac caagcttcgt      60
aaacagctgg cagctaagaa atacctcaac gacctgaaaa agggcggtac ctaatgactc     120
gag                                                                  123

<210> SEQ ID NO 57
<211> LENGTH: 38
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(38)

<400> SEQUENCE: 57

His Ser Asp Gly Ile Phe Thr Glu Ser Tyr Ser Arg Tyr Arg Lys Gln
1               5                   10                  15

Met Ala Val Lys Lys Tyr Leu Ala Ala Leu Lys Lys Arg Tyr Lys
            20                  25                  30

Gln Arg Val Lys Asn Lys
        35

<210> SEQ ID NO 58
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (28)..(28)
<223> OTHER INFORMATION: AMIDATION
```

-continued

```
<400> SEQUENCE: 58

His Ser Asp Ala Val Phe Thr Glu Asn Tyr Thr Arg Leu Arg Lys Gln
1               5                   10                  15

Met Ala Val Lys Lys Tyr Leu Asn Ser Leu Lys Lys
            20                  25

<210> SEQ ID NO 59
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: AMIDATION

<400> SEQUENCE: 59

His Ser Asp Gly Ile Phe Thr Asp Ser Tyr Ser Arg Tyr Arg Lys Gln
1               5                   10                  15

Met Ala Val Lys Lys Tyr Leu Ser Ala Val Arg His Gly Gly Thr
            20                  25                  30

<210> SEQ ID NO 60
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: AMIDATION

<400> SEQUENCE: 60

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys Gln Gly Gly Thr
            20                  25                  30

<210> SEQ ID NO 61
<211> LENGTH: 36
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: AMIDATION

<400> SEQUENCE: 61

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys Lys Tyr Leu Ala Ala
            20                  25                  30

Val Arg His Gly
        35

<210> SEQ ID NO 62
<211> LENGTH: 40
<212> TYPE: PRT
<213> ORGANISM: Artificial
<220> FEATURE:
<223> OTHER INFORMATION: Synthetic Construct
<220> FEATURE:
```

```
<221> NAME/KEY: PEPTIDE
<222> LOCATION: (1)..(40)

<400> SEQUENCE: 62

Ser Trp Cys Glu Pro Gly Trp Cys Arg His Ser Asp Ala Val Phe Thr
 1               5                  10                  15

Glu Asn Tyr Thr Lys Leu Arg Lys Gln Leu Ala Ala Lys Lys Tyr Leu
            20                  25                  30

Asn Asp Leu Lys Lys Gly Gly Thr
            35                  40

<210> SEQ ID NO 63
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 63

His Ser Asp Ala Val Phe Thr Asp Asn Tyr Thr Arg Leu Arg Lys Gln
 1               5                  10                  15

Leu Ala Ala Lys Lys Tyr Leu Asn Asp Ile Leu Lys Gly Gly Thr
            20                  25                  30

<210> SEQ ID NO 64
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 64

His Ser Asp Ala Val Phe Thr Asp Asn Tyr Thr Arg Leu Arg Lys Gln
 1               5                  10                  15

Leu Ala Ala Lys Lys Tyr Leu Asn Asp Ile Leu Asn Gly Gly Thr
            20                  25                  30

<210> SEQ ID NO 65
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 65

His Ser Asp Ala Val Phe Thr Asp Asn Tyr Thr Arg Leu Arg Lys Gln
 1               5                  10                  15

Leu Ala Val Lys Lys Tyr Leu Asn Asp Ile Leu Lys Gly Gly Thr
            20                  25                  30

<210> SEQ ID NO 66
<211> LENGTH: 31
<212> TYPE: PRT
<213> ORGANISM: Artificial
<220> FEATURE:
<223> OTHER INFORMATION: Synthetic Construct
<220> FEATURE:
```

```
<221> NAME/KEY: PEPTIDE
<222> LOCATION: (1)..(31)

<400> SEQUENCE: 66

His Ser Asp Gly Ile Phe Thr Asp Ser Tyr Ser Arg Tyr Arg Lys Gln
1               5                   10                  15

Leu Ala Ala Lys Lys Tyr Leu Ala Asp Val Lys Lys Gly Gly Thr
            20                  25                  30

<210> SEQ ID NO 67
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 67

His Ser Asp Gly Ile Phe Thr Asp Ser Tyr Ser Arg Tyr Arg Lys Gln
1               5                   10                  15

Leu Ala Ala Lys Lys Tyr Leu Ala Asp Val Lys Lys
            20                  25

<210> SEQ ID NO 68
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 68

His Ser Asp Gly Ile Phe Thr Asp Ser Tyr Ser Arg Tyr Arg Lys Gln
1               5                   10                  15

Leu Ala Val Lys Lys Tyr Leu Ala Ala Val Lys Lys
            20                  25

<210> SEQ ID NO 69
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)

<400> SEQUENCE: 69

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys Lys
            20                  25

<210> SEQ ID NO 70
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(28)
```

-continued

```
<400> SEQUENCE: 70

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys
            20                  25

<210> SEQ ID NO 71
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 71

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Arg
            20                  25                  30

<210> SEQ ID NO 72
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 72

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 73
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 73

His Ser Asp Ala Val Phe Thr Asp Asn Tyr Thr Arg Leu Arg Lys Gln
1               5                   10                  15

Leu Ala Ala Lys Lys Tyr Leu Asn Thr Ile Lys Asn Lys Arg Tyr
            20                  25                  30

<210> SEQ ID NO 74
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 74

His Ser Asp Ala Val Phe Thr Asp Asn Tyr Thr Arg Leu Arg Lys Gln
```

```
                1               5                  10                 15
Val Ala Ala Lys Lys Tyr Leu Asn Ser Ile Lys Asn Lys Arg Tyr
            20                  25                 30

<210> SEQ ID NO 75
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 75

His Ser Asp Ala Val Phe Thr Asp Asn Tyr Thr Arg Leu Arg Lys Gln
1               5                  10                 15

Met Ala Ala Lys Lys Tyr Leu Gln Ser Ile Lys Asn Lys Arg Tyr
            20                  25                 30

<210> SEQ ID NO 76
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 76

His Ser Asp Ala Val Phe Thr Asp Asn Tyr Thr Arg Leu Arg Lys Gln
1               5                  10                 15

Met Ala Ala Lys Lys Tyr Leu Asn Thr Ile Lys Asn Lys Arg Tyr
            20                  25                 30

<210> SEQ ID NO 77
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 77

His Ser Asp Ala Val Phe Thr Asp Gln Tyr Thr Arg Leu Arg Lys Gln
1               5                  10                 15

Met Ala Ala Lys Lys Tyr Leu Asn Ser Ile Lys Asn Lys Arg Tyr
            20                  25                 30

<210> SEQ ID NO 78
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 78

His Ser Asp Ala Val Phe Thr Asp Gln Tyr Thr Arg Leu Arg Lys Gln
1               5                  10                 15

Leu Ala Ala Lys Lys Tyr Leu Asn Thr Ile Lys Asn Lys Arg Tyr
```

```
              20                  25                  30

<210> SEQ ID NO 79
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 79

His Ser Asp Ala Val Phe Thr Asp Asn Tyr Thr Arg Leu Arg Lys Gln
1               5                  10                  15

Met Ala Ala His Lys Tyr Leu Asn Ser Ile Lys Asn Lys Arg Tyr
              20                  25                  30

<210> SEQ ID NO 80
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 80

His Ser Asp Ala Val Phe Thr Asp Asn Tyr Thr Arg Leu Arg Lys Gln
1               5                  10                  15

Met Ala Ala Lys His Tyr Leu Asn Ser Ile Lys Asn Lys Arg Tyr
              20                  25                  30

<210> SEQ ID NO 81
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 81

His Ser Asp Ala Val Phe Thr Asp Gln Tyr Thr Arg Leu Arg Lys Gln
1               5                  10                  15

Leu Ala Ala His Lys Tyr Leu Asn Thr Ile Lys Asn Lys Arg Tyr
              20                  25                  30

<210> SEQ ID NO 82
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 82

His Ser Asp Ala Val Phe Thr Asp Gln Tyr Thr Arg Leu Arg Lys Gln
1               5                  10                  15

Leu Ala Ala Lys His Tyr Leu Asn Thr Ile Lys Asn Lys Arg Tyr
              20                  25                  30
```

```
<210> SEQ ID NO 83
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 83

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Lys Lys Arg
            20                  25                  30

<210> SEQ ID NO 84
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 84

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys Lys Arg
            20                  25                  30

<210> SEQ ID NO 85
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 85

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Asn Lys Arg Tyr
            20                  25                  30

<210> SEQ ID NO 86
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 86

His Ser Asp Ala Val Phe Thr Asp Asn Tyr Thr Arg Leu Arg Lys Gln
1               5                   10                  15

Val Ala Val Lys Lys Tyr Leu Gln Ser Ile Lys Lys Lys Arg
            20                  25                  30

<210> SEQ ID NO 87
<211> LENGTH: 29
<212> TYPE: PRT
```

<210> SEQ ID NO 87
<211> LENGTH: 29 (implied)
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 87

His Ser Asp Ala Val Phe Thr Asp Asn Tyr Thr Arg Leu Arg Lys Gln
 1               5                  10                  15
Val Ala Val Lys Lys Tyr Leu Gln Ser Ile Lys Lys Lys
                20                  25

<210> SEQ ID NO 88
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 88

His Ser Asp Ala Val Phe Thr Asp Asn Tyr Thr Arg Leu Arg Lys Gln
 1               5                  10                  15
Val Ala Val Lys Lys Tyr Leu Gln Ser Ile Lys Asn Lys Arg Tyr
                20                  25                  30

<210> SEQ ID NO 89
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 89

His Ser Asp Ala Val Phe Thr Asp Asn Tyr Thr Arg Leu Arg Lys Gln
 1               5                  10                  15
Val Ala Ala Lys Lys Tyr Leu Gln Ser Ile Leu Lys Lys Arg Tyr
                20                  25                  30

<210> SEQ ID NO 90
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 90

His Ser Asp Ala Val Phe Thr Asp Asn Tyr Thr Arg Leu Arg Lys Gln
 1               5                  10                  15
Val Ala Ala Lys Lys Tyr Leu Gln Ser Ile Leu Lys Lys Arg
                20                  25                  30

<210> SEQ ID NO 91
<211> LENGTH: 29
<212> TYPE: PRT
<213> ORGANISM: Artificial
<220> FEATURE:
<223> OTHER INFORMATION: Synthetic Construct

```
<220> FEATURE:
<221> NAME/KEY: PEPTIDE
<222> LOCATION: (1)..(29)

<400> SEQUENCE: 91

His Ser Asp Ala Val Phe Thr Asp Asn Tyr Thr Arg Leu Arg Lys Gln
 1               5                  10                  15

Val Ala Ala Lys Lys Tyr Leu Gln Ser Ile Leu Lys Lys
            20                  25

<210> SEQ ID NO 92
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 92

His Ser Asp Ala Val Phe Thr Asp Asn Tyr Thr Arg Leu Arg Lys Gln
 1               5                  10                  15

Val Ala Ala Lys Lys Tyr Leu Gln Ser Ile Lys Asn Lys
            20                  25

<210> SEQ ID NO 93
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 93

His Ser Asp Ala Val Phe Thr Asp Asn Tyr Thr Arg Leu Arg Lys Gln
 1               5                  10                  15

Val Ala Val Lys Lys Tyr Leu Gln Ser Ile Leu Lys Lys Arg Tyr
            20                  25                  30

<210> SEQ ID NO 94
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 94

His Ser Asp Ala Val Phe Thr Asp Asn Tyr Thr Arg Leu Arg Lys Gln
 1               5                  10                  15

Val Ala Val Lys Lys Tyr Leu Gln Ser Ile Leu Lys Lys Arg
            20                  25                  30

<210> SEQ ID NO 95
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)
```

<400> SEQUENCE: 95

His Ser Asp Ala Val Phe Thr Asp Asn Tyr Thr Arg Leu Arg Lys Gln
1               5                   10                  15

Val Ala Val Lys Lys Tyr Leu Gln Ser Ile Leu Lys Lys
            20                  25

<210> SEQ ID NO 96
<211> LENGTH: 29
<212> TYPE: PRT
<213> ORGANISM: Artificial
<220> FEATURE:
<223> OTHER INFORMATION: Synthetic Construct

<400> SEQUENCE: 96

His Ser Asp Ala Val Phe Thr Asp Asn Tyr Thr Arg Leu Arg Lys Gln
1               5                   10                  15

Val Ala Val Lys Lys Tyr Leu Gln Ser Ile Lys Asn Lys
            20                  25

<210> SEQ ID NO 97
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 97

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Asn Lys Arg Tyr
            20                  25                  30

<210> SEQ ID NO 98
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 98

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Asn Lys Arg
            20                  25                  30

<210> SEQ ID NO 99
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(29)

<400> SEQUENCE: 99

His Ser Asp Ala Val Phe Thr Asp Asn Tyr Thr Arg Leu Arg Lys Gln
1               5                   10                  15

-continued

Val Ala Ala Lys Lys Tyr Leu Gln Ser Ile Leu Asn Lys
            20                  25

<210> SEQ ID NO 100
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 100

His Ser Asp Ala Val Phe Thr Asp Asn Tyr Thr Arg Leu Arg Lys Gln
1               5                   10                  15

Met Ala Cys Lys Lys Tyr Leu Asn Ser Ile Lys Asn Lys Arg
            20                  25                  30

<210> SEQ ID NO 101
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 101

His Ser Asp Ala Val Phe Thr Asp Asn Tyr Thr Arg Leu Arg Lys Gln
1               5                   10                  15

Met Ala Asp Lys Lys Tyr Leu Asn Ser Ile Lys Asn Lys Arg
            20                  25                  30

<210> SEQ ID NO 102
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 102

His Ser Asp Ala Val Phe Thr Asp Asn Tyr Thr Arg Leu Arg Lys Gln
1               5                   10                  15

Met Ala Glu Lys Lys Tyr Leu Asn Ser Ile Lys Asn Lys Arg
            20                  25                  30

<210> SEQ ID NO 103
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 103

His Ser Asp Ala Val Phe Thr Asp Asn Tyr Thr Arg Leu Arg Lys Gln
1               5                   10                  15

Met Ala Phe Lys Lys Tyr Leu Asn Ser Ile Lys Asn Lys Arg
            20                  25                  30

```
<210> SEQ ID NO 104
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 104

His Ser Asp Ala Val Phe Thr Asp Asn Tyr Thr Arg Leu Arg Lys Gln
1               5                   10                  15

Met Ala Gly Lys Lys Tyr Leu Asn Ser Ile Lys Asn Lys Arg
            20                  25                  30

<210> SEQ ID NO 105
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 105

His Ser Asp Ala Val Phe Thr Asp Asn Tyr Thr Arg Leu Arg Lys Gln
1               5                   10                  15

Met Ala His Lys Lys Tyr Leu Asn Ser Ile Lys Asn Lys Arg
            20                  25                  30

<210> SEQ ID NO 106
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 106

His Ser Asp Ala Val Phe Thr Asp Asn Tyr Thr Arg Leu Arg Lys Gln
1               5                   10                  15

Met Ala Ile Lys Lys Tyr Leu Asn Ser Ile Lys Asn Lys Arg
            20                  25                  30

<210> SEQ ID NO 107
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 107

His Ser Asp Ala Val Phe Thr Asp Asn Tyr Thr Arg Leu Arg Lys Gln
1               5                   10                  15

Met Ala Lys Lys Lys Tyr Leu Asn Ser Ile Lys Asn Lys Arg
            20                  25                  30

<210> SEQ ID NO 108
<211> LENGTH: 30
```

```
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 108
```

His Ser Asp Ala Val Phe Thr Asp Asn Tyr Thr Arg Leu Arg Lys Gln
1               5                   10                  15

Met Ala Leu Lys Lys Tyr Leu Asn Ser Ile Lys Asn Lys Arg
            20                  25                  30

```
<210> SEQ ID NO 109
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 109
```

His Ser Asp Ala Val Phe Thr Asp Asn Tyr Thr Arg Leu Arg Lys Gln
1               5                   10                  15

Met Ala Met Lys Lys Tyr Leu Asn Ser Ile Lys Asn Lys Arg
            20                  25                  30

```
<210> SEQ ID NO 110
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 110
```

His Ser Asp Ala Val Phe Thr Asp Asn Tyr Thr Arg Leu Arg Lys Gln
1               5                   10                  15

Met Ala Asn Lys Lys Tyr Leu Asn Ser Ile Lys Asn Lys Arg
            20                  25                  30

```
<210> SEQ ID NO 111
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 111
```

His Ser Asp Ala Val Phe Thr Asp Asn Tyr Thr Arg Leu Arg Lys Gln
1               5                   10                  15

Met Ala Pro Lys Lys Tyr Leu Asn Ser Ile Lys Asn Lys Arg
            20                  25                  30

```
<210> SEQ ID NO 112
<211> LENGTH: 30
<212> TYPE: PRT
<213> ORGANISM: Artificial
<220> FEATURE:
```

```
<223> OTHER INFORMATION: Synthetic Construct
<220> FEATURE:
<221> NAME/KEY: PEPTIDE
<222> LOCATION: (1)..(30)

<400> SEQUENCE: 112

His Ser Asp Ala Val Phe Thr Asp Asn Tyr Thr Arg Leu Arg Lys Gln
1               5                   10                  15

Met Ala Gln Lys Lys Tyr Leu Asn Ser Ile Lys Asn Lys Arg
            20                  25                  30

<210> SEQ ID NO 113
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 113

His Ser Asp Ala Val Phe Thr Asp Asn Tyr Thr Arg Leu Arg Lys Gln
1               5                   10                  15

Met Ala Arg Lys Lys Tyr Leu Asn Ser Ile Lys Asn Lys Arg
            20                  25                  30

<210> SEQ ID NO 114
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 114

His Ser Asp Ala Val Phe Thr Asp Asn Tyr Thr Arg Leu Arg Lys Gln
1               5                   10                  15

Met Ala Ser Lys Lys Tyr Leu Asn Ser Ile Lys Asn Lys Arg
            20                  25                  30

<210> SEQ ID NO 115
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 115

His Ser Asp Ala Val Phe Thr Asp Asn Tyr Thr Arg Leu Arg Lys Gln
1               5                   10                  15

Met Ala Thr Lys Lys Tyr Leu Asn Ser Ile Lys Asn Lys Arg
            20                  25                  30

<210> SEQ ID NO 116
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
```

```
<222> LOCATION: (1)..(30)

<400> SEQUENCE: 116

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Asn Lys Arg
            20                  25                  30

<210> SEQ ID NO 117
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 117

His Ser Asp Ala Val Phe Thr Asp Asn Tyr Thr Arg Leu Arg Lys Gln
1               5                   10                  15

Met Ala Trp Lys Lys Tyr Leu Asn Ser Ile Lys Asn Lys Arg
            20                  25                  30

<210> SEQ ID NO 118
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 118

His Ser Asp Ala Val Phe Thr Asp Asn Tyr Thr Arg Leu Arg Lys Gln
1               5                   10                  15

Met Ala Tyr Lys Lys Tyr Leu Asn Ser Ile Lys Asn Lys Arg
            20                  25                  30

<210> SEQ ID NO 119
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 119

His Ser Asp Ala Val Phe Thr Asp Asn Tyr Thr Arg Leu Arg Lys Gln
1               5                   10                  15

Met Ala Ala Lys Lys Tyr Leu Asn Ser Ile Ala Asn Lys Arg
            20                  25                  30

<210> SEQ ID NO 120
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 120
```

His Ser Asp Ala Val Phe Thr Asp Asn Tyr Thr Arg Leu Arg Lys Gln
1               5                   10                  15

Met Ala Ala Lys Lys Tyr Leu Asn Ser Ile Cys Asn Lys Arg
            20                  25                  30

<210> SEQ ID NO 121
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 121

His Ser Asp Ala Val Phe Thr Asp Asn Tyr Thr Arg Leu Arg Lys Gln
1               5                   10                  15

Met Ala Ala Lys Lys Tyr Leu Asn Ser Ile Asp Asn Lys Arg
            20                  25                  30

<210> SEQ ID NO 122
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 122

His Ser Asp Ala Val Phe Thr Asp Asn Tyr Thr Arg Leu Arg Lys Gln
1               5                   10                  15

Met Ala Ala Lys Lys Tyr Leu Asn Ser Ile Glu Asn Lys Arg
            20                  25                  30

<210> SEQ ID NO 123
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 123

His Ser Asp Ala Val Phe Thr Asp Asn Tyr Thr Arg Leu Arg Lys Gln
1               5                   10                  15

Met Ala Ala Lys Lys Tyr Leu Asn Ser Ile Phe Asn Lys Arg
            20                  25                  30

<210> SEQ ID NO 124
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 124

His Ser Asp Ala Val Phe Thr Asp Asn Tyr Thr Arg Leu Arg Lys Gln
1               5                   10                  15

```
Met Ala Ala Lys Lys Tyr Leu Asn Ser Ile Gly Asn Lys Arg
            20                  25                  30

<210> SEQ ID NO 125
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 125

His Ser Asp Ala Val Phe Thr Asp Asn Tyr Thr Arg Leu Arg Lys Gln
1               5                   10                  15

Met Ala Ala Lys Lys Tyr Leu Asn Ser Ile His Asn Lys Arg
            20                  25                  30

<210> SEQ ID NO 126
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 126

His Ser Asp Ala Val Phe Thr Asp Asn Tyr Thr Arg Leu Arg Lys Gln
1               5                   10                  15

Met Ala Ala Lys Lys Tyr Leu Asn Ser Ile Ile Asn Lys Arg
            20                  25                  30

<210> SEQ ID NO 127
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 127

His Ser Asp Ala Val Phe Thr Asp Asn Tyr Thr Arg Leu Arg Lys Gln
1               5                   10                  15

Met Ala Ala Lys Lys Tyr Leu Asn Ser Ile Met Asn Lys Arg
            20                  25                  30

<210> SEQ ID NO 128
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 128

His Ser Asp Ala Val Phe Thr Asp Asn Tyr Thr Arg Leu Arg Lys Gln
1               5                   10                  15

Met Ala Ala Lys Lys Tyr Leu Asn Ser Ile Asn Asn Lys Arg
            20                  25                  30
```

<210> SEQ ID NO 129
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 129

His Ser Asp Ala Val Phe Thr Asp Asn Tyr Thr Arg Leu Arg Lys Gln
1               5                   10                  15

Met Ala Ala Lys Lys Tyr Leu Asn Ser Ile Pro Asn Lys Arg
            20                  25                  30

<210> SEQ ID NO 130
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 130

His Ser Asp Ala Val Phe Thr Asp Asn Tyr Thr Arg Leu Arg Lys Gln
1               5                   10                  15

Met Ala Ala Lys Lys Tyr Leu Asn Ser Ile Gln Asn Lys Arg
            20                  25                  30

<210> SEQ ID NO 131
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 131

His Ser Asp Ala Val Phe Thr Asp Asn Tyr Thr Arg Leu Arg Lys Gln
1               5                   10                  15

Met Ala Ala Lys Lys Tyr Leu Asn Ser Ile Arg Asn Lys Arg
            20                  25                  30

<210> SEQ ID NO 132
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 132

His Ser Asp Ala Val Phe Thr Asp Asn Tyr Thr Arg Leu Arg Lys Gln
1               5                   10                  15

Met Ala Ala Lys Lys Tyr Leu Asn Ser Ile Ser Asn Lys Arg
            20                  25                  30

<210> SEQ ID NO 133

```
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 133

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Thr Asn Lys Arg
            20                  25                  30

<210> SEQ ID NO 134
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 134

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Val Asn Lys Arg
            20                  25                  30

<210> SEQ ID NO 135
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 135

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Trp Asn Lys Arg
            20                  25                  30

<210> SEQ ID NO 136
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 136

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Tyr Asn Lys Arg
            20                  25                  30

<210> SEQ ID NO 137
<211> LENGTH: 30
<212> TYPE: PRT
<213> ORGANISM: Artificial
```

```
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 137
```

His Ser Asp Ala Val Phe Thr Asp Asn Tyr Thr Arg Leu Arg Lys Gln
1               5                  10                  15

Met Ala Ala Lys Lys Tyr Leu Asn Ser Ile Lys Asn Ala Arg
            20                  25                  30

```
<210> SEQ ID NO 138
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 138
```

His Ser Asp Ala Val Phe Thr Asp Asn Tyr Thr Arg Leu Arg Lys Gln
1               5                  10                  15

Met Ala Ala Lys Lys Tyr Leu Asn Ser Ile Lys Asn Cys Arg
            20                  25                  30

```
<210> SEQ ID NO 139
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 139
```

His Ser Asp Ala Val Phe Thr Asp Asn Tyr Thr Arg Leu Arg Lys Gln
1               5                  10                  15

Met Ala Ala Lys Lys Tyr Leu Asn Ser Ile Lys Asn Asp Arg
            20                  25                  30

```
<210> SEQ ID NO 140
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 140
```

His Ser Asp Ala Val Phe Thr Asp Asn Tyr Thr Arg Leu Arg Lys Gln
1               5                  10                  15

Met Ala Ala Lys Lys Tyr Leu Asn Ser Ile Lys Asn Glu Arg
            20                  25                  30

```
<210> SEQ ID NO 141
<211> LENGTH: 30
<212> TYPE: PRT
<213> ORGANISM: Artificial
<220> FEATURE:
<223> OTHER INFORMATION: Synthetic Construct
<220> FEATURE:
```

```
<221> NAME/KEY: PEPTIDE
<222> LOCATION: (1)..(30)

<400> SEQUENCE: 141

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Phe Arg
            20                  25                  30

<210> SEQ ID NO 142
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 142

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Gly Arg
            20                  25                  30

<210> SEQ ID NO 143
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 143

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn His Arg
            20                  25                  30

<210> SEQ ID NO 144
<211> LENGTH: 30
<212> TYPE: PRT
<213> ORGANISM: Artificial
<220> FEATURE:
<223> OTHER INFORMATION: Synthetic Construct

<400> SEQUENCE: 144

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Ile Arg
            20                  25                  30

<210> SEQ ID NO 145
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 145

His Ser Asp Ala Val Phe Thr Asp Asn Tyr Thr Arg Leu Arg Lys Gln
```

```
                1               5                  10                 15
Met Ala Ala Lys Lys Tyr Leu Asn Ser Ile Lys Asn Leu Arg
            20                  25                 30

<210> SEQ ID NO 146
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 146

His Ser Asp Ala Val Phe Thr Asp Asn Tyr Thr Arg Leu Arg Lys Gln
1               5                  10                 15

Met Ala Ala Lys Lys Tyr Leu Asn Ser Ile Lys Asn Met Arg
            20                  25                 30

<210> SEQ ID NO 147
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 147

His Ser Asp Ala Val Phe Thr Asp Asn Tyr Thr Arg Leu Arg Lys Gln
1               5                  10                 15

Met Ala Ala Lys Lys Tyr Leu Asn Ser Ile Lys Asn Asn Arg
            20                  25                 30

<210> SEQ ID NO 148
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 148

His Ser Asp Ala Val Phe Thr Asp Asn Tyr Thr Arg Leu Arg Lys Gln
1               5                  10                 15

Met Ala Ala Lys Lys Tyr Leu Asn Ser Ile Lys Asn Pro Arg
            20                  25                 30

<210> SEQ ID NO 149
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 149

His Ser Asp Ala Val Phe Thr Asp Asn Tyr Thr Arg Leu Arg Lys Gln
1               5                  10                 15

Met Ala Ala Lys Lys Tyr Leu Asn Ser Ile Lys Asn Gln Arg
```

```
                20                  25                  30

<210> SEQ ID NO 150
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 150

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Arg Arg
            20                  25                  30

<210> SEQ ID NO 151
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 151

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Ser Arg
            20                  25                  30

<210> SEQ ID NO 152
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 152

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Thr Arg
            20                  25                  30

<210> SEQ ID NO 153
<211> LENGTH: 30
<212> TYPE: PRT
<213> ORGANISM: Artificial
<220> FEATURE:
<223> OTHER INFORMATION: Synthetic Construct

<400> SEQUENCE: 153

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Val Arg
            20                  25                  30

<210> SEQ ID NO 154
<211> LENGTH: 30
<212> TYPE: PRT
```

```
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 154

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Trp Arg
            20                  25                  30

<210> SEQ ID NO 155
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 155

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Tyr Arg
            20                  25                  30

<210> SEQ ID NO 156
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 156

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Ala
            20                  25                  30

<210> SEQ ID NO 157
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 157

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Asp
            20                  25                  30

<210> SEQ ID NO 158
<211> LENGTH: 30
<212> TYPE: PRT
<213> ORGANISM: Artificial
<220> FEATURE:
<223> OTHER INFORMATION: Synthetic Construct
```

```
<220> FEATURE:
<221> NAME/KEY: PEPTIDE
<222> LOCATION: (1)..(30)

<400> SEQUENCE: 158

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Lys Asn Lys Glu
            20                  25                  30

<210> SEQ ID NO 159
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 159

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Lys Asn Lys Phe
            20                  25                  30

<210> SEQ ID NO 160
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 160

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Lys Asn Lys Gly
            20                  25                  30

<210> SEQ ID NO 161
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 161

His Ser Asp Ala Val Phe Thr Asp Asn Tyr Thr Arg Leu Arg Lys Gln
 1               5                  10                  15

Met Ala Ala Lys Lys Tyr Leu Asn Ser Ile Lys Asn Lys His
            20                  25                  30

<210> SEQ ID NO 162
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)
```

<400> SEQUENCE: 162

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Ile
            20                  25                  30

<210> SEQ ID NO 163
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 163

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Lys
            20                  25                  30

<210> SEQ ID NO 164
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 164

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Leu
            20                  25                  30

<210> SEQ ID NO 165
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 165

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Met
            20                  25                  30

<210> SEQ ID NO 166
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 166

-continued

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Asn
            20                  25                  30

<210> SEQ ID NO 167
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 167

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Pro
            20                  25                  30

<210> SEQ ID NO 168
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 168

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Gln
            20                  25                  30

<210> SEQ ID NO 169
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 169

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Ser
            20                  25                  30

<210> SEQ ID NO 170
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 170

His Ser Asp Ala Val Phe Thr Asp Asn Tyr Thr Arg Leu Arg Lys Gln
1               5                   10                  15

```
Met Ala Ala Lys Lys Tyr Leu Asn Ser Ile Lys Asn Lys Thr
            20                  25                  30

<210> SEQ ID NO 171
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 171

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Val
            20                  25                  30

<210> SEQ ID NO 172
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 172

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Trp
            20                  25                  30

<210> SEQ ID NO 173
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 173

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Tyr
            20                  25                  30

<210> SEQ ID NO 174
<211> LENGTH: 40
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(40)

<400> SEQUENCE: 174

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr Ser
            20                  25                  30
```

```
Trp Cys Glu Pro Gly Trp Cys Arg
        35                  40
```

<210> SEQ ID NO 175
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(31)

<400> SEQUENCE: 175

```
His Ser Asp Ala Val Phe Thr Asp Asp Tyr Thr Arg Leu Arg Lys Glu
1               5                   10                  15
Val Ala Ala Lys Lys Tyr Leu Glu Ser Ile Lys Asp Lys Arg Tyr
            20                  25                  30
```

<210> SEQ ID NO 176
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 176

```
Glu Ser Asp Gly Ile Phe Thr Asp Ser Tyr Ser Arg Tyr Arg Lys Gln
1               5                   10                  15
Met Ala Val Lys Lys Tyr Leu Ala Ala Val Leu
            20                  25
```

<210> SEQ ID NO 177
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 177

```
His Lys Asp Gly Ile Phe Thr Asp Ser Tyr Ser Arg Tyr Arg Lys Gln
1               5                   10                  15
Met Ala Val Lys Lys Tyr Leu Ala Ala Val Leu
            20                  25
```

<210> SEQ ID NO 178
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 178

```
His Ser Lys Gly Ile Phe Thr Asp Ser Tyr Ser Arg Tyr Arg Lys Gln
1               5                   10                  15
```

```
Met Ala Val Lys Lys Tyr Leu Ala Ala Val Leu
            20                  25
```

```
<210> SEQ ID NO 179
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 179

His Ser Asp Lys Ile Phe Thr Asp Ser Tyr Ser Arg Tyr Arg Lys Gln
1               5                   10                  15

Met Ala Val Lys Lys Tyr Leu Ala Ala Val Leu
            20                  25
```

```
<210> SEQ ID NO 180
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 180

His Ser Asp Gly Lys Phe Thr Asp Ser Tyr Ser Arg Tyr Arg Lys Gln
1               5                   10                  15

Met Ala Val Lys Lys Tyr Leu Ala Ala Val Leu
            20                  25
```

```
<210> SEQ ID NO 181
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 181

His Ser Asp Gly Ile Lys Thr Asp Ser Tyr Ser Arg Tyr Arg Lys Gln
1               5                   10                  15

Met Ala Val Lys Lys Tyr Leu Ala Ala Val Leu
            20                  25
```

```
<210> SEQ ID NO 182
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 182

His Ser Asp Gly Ile Phe Lys Asp Ser Tyr Ser Arg Tyr Arg Lys Gln
1               5                   10                  15
```

```
Met Ala Val Lys Lys Tyr Leu Ala Ala Val Leu
            20                  25

<210> SEQ ID NO 183
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 183

His Ser Asp Gly Ile Phe Thr Lys Ser Tyr Ser Arg Tyr Arg Lys Gln
1               5                   10                  15

Met Ala Val Lys Lys Tyr Leu Ala Ala Val Leu
            20                  25

<210> SEQ ID NO 184
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 184

His Ser Asp Gly Ile Phe Thr Asp Lys Tyr Ser Arg Tyr Arg Lys Gln
1               5                   10                  15

Met Ala Val Lys Lys Tyr Leu Ala Ala Val Leu
            20                  25

<210> SEQ ID NO 185
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 185

His Ser Asp Gly Ile Phe Thr Asp Ser Lys Ser Arg Tyr Arg Lys Gln
1               5                   10                  15

Met Ala Val Lys Lys Tyr Leu Ala Ala Val Leu
            20                  25

<210> SEQ ID NO 186
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 186

His Ser Asp Gly Ile Phe Thr Asp Ser Tyr Lys Arg Tyr Arg Lys Gln
```

```
                1               5                  10                  15
Met Ala Val Lys Lys Tyr Leu Ala Ala Val Leu
            20                  25

<210> SEQ ID NO 187
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 187

His Ser Asp Gly Ile Phe Thr Asp Ser Tyr Ser Glu Tyr Arg Lys Gln
1               5                   10                  15

Met Ala Val Lys Lys Tyr Leu Ala Ala Val Leu
            20                  25

<210> SEQ ID NO 188
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 188

His Ser Asp Gly Ile Phe Thr Asp Ser Tyr Ser Arg Lys Arg Lys Gln
1               5                   10                  15

Met Ala Val Lys Lys Tyr Leu Ala Ala Val Leu
            20                  25

<210> SEQ ID NO 189
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 189

His Ser Asp Gly Ile Phe Thr Asp Ser Tyr Ser Arg Tyr Glu Lys Gln
1               5                   10                  15

Met Ala Val Lys Lys Tyr Leu Ala Ala Val Leu
            20                  25

<210> SEQ ID NO 190
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 190
```

His Ser Asp Gly Ile Phe Thr Asp Ser Tyr Ser Arg Tyr Arg Glu Gln
1               5                   10                  15

Met Ala Val Lys Lys Tyr Leu Ala Ala Val Leu
            20                  25

<210> SEQ ID NO 191
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 191

His Ser Asp Gly Ile Phe Thr Asp Ser Tyr Ser Arg Tyr Arg Lys Lys
1               5                   10                  15

Met Ala Val Lys Lys Tyr Leu Ala Ala Val Leu
            20                  25

<210> SEQ ID NO 192
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 192

His Ser Asp Gly Ile Phe Thr Asp Ser Tyr Ser Arg Tyr Arg Lys Gln
1               5                   10                  15

Lys Ala Val Lys Lys Tyr Leu Ala Ala Val Leu
            20                  25

<210> SEQ ID NO 193
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 193

His Ser Asp Gly Ile Phe Thr Asp Ser Tyr Ser Arg Tyr Arg Lys Gln
1               5                   10                  15

Met Lys Val Lys Lys Tyr Leu Ala Ala Val Leu
            20                  25

<210> SEQ ID NO 194
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 194

His Ser Asp Gly Ile Phe Thr Asp Ser Tyr Ser Arg Tyr Arg Lys Gln
1               5                   10                  15

Met Ala Lys Lys Lys Tyr Leu Ala Ala Val Leu
            20                  25

<210> SEQ ID NO 195
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 195

His Ser Asp Gly Ile Phe Thr Asp Ser Tyr Ser Arg Tyr Arg Lys Gln
1               5                   10                  15

Met Ala Val Glu Lys Tyr Leu Ala Ala Val Leu
            20                  25

<210> SEQ ID NO 196
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 196

His Ser Asp Gly Ile Phe Thr Asp Ser Tyr Ser Arg Tyr Arg Lys Gln
1               5                   10                  15

Met Ala Val Lys Glu Tyr Leu Ala Ala Val Leu
            20                  25

<210> SEQ ID NO 197
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 197

His Ser Asp Gly Ile Phe Thr Asp Ser Tyr Ser Arg Tyr Arg Lys Gln
1               5                   10                  15

Met Ala Val Lys Lys Lys Leu Ala Ala Val Leu
            20                  25

<210> SEQ ID NO 198
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

```
<400> SEQUENCE: 198

His Ser Asp Gly Ile Phe Thr Asp Ser Tyr Ser Arg Tyr Arg Lys Gln
1               5                   10                  15

Met Ala Val Lys Lys Tyr Lys Ala Ala Val Leu
            20                  25

<210> SEQ ID NO 199
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 199

His Ser Asp Gly Ile Phe Thr Asp Ser Tyr Ser Arg Tyr Arg Lys Gln
1               5                   10                  15

Met Ala Val Lys Lys Tyr Leu Lys Ala Val Leu
            20                  25

<210> SEQ ID NO 200
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 200

His Ser Asp Gly Ile Phe Thr Asp Ser Tyr Ser Arg Tyr Arg Lys Gln
1               5                   10                  15

Met Ala Val Lys Lys Tyr Leu Ala Lys Val Leu
            20                  25

<210> SEQ ID NO 201
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION

<400> SEQUENCE: 201

His Ser Asp Gly Ile Phe Thr Asp Ser Tyr Ser Arg Tyr Arg Lys Gln
1               5                   10                  15

Met Ala Val Lys Lys Tyr Leu Ala Ala Lys Leu
            20                  25

<210> SEQ ID NO 202
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (27)..(27)
<223> OTHER INFORMATION: AMIDATION
```

```
<400> SEQUENCE: 202

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys
            20                  25

<210> SEQ ID NO 203
<211> LENGTH: 111
<212> TYPE: DNA
<213> ORGANISM: Artificial
<220> FEATURE:
<223> OTHER INFORMATION: Synthetic Construct

<400> SEQUENCE: 203
ggatccatcg aaggtcgtca ctccgatggt atcttcaccg actcctactc gaggtaccgc      60
aagcagatgg ctgtaaagaa atatctggct gcagttctgt aatgactcga g              111

<210> SEQ ID NO 204
<211> LENGTH: 123
<212> TYPE: DNA
<213> ORGANISM: Artificial
<220> FEATURE:
<223> OTHER INFORMATION: Synthetic Construct

<400> SEQUENCE: 204
ggatccatcg aaggtcgtca ctccgacgct gttttcaccg acaactacac gcgtctgcgt      60
aaacagatgg ctgttaagaa atacctgaat tccatcaaga aggcggtac ctaatgactc     120 gag                                                                   123

<210> SEQ ID NO 205
<211> LENGTH: 123
<212> TYPE: DNA
<213> ORGANISM: Artificial
<220> FEATURE:
<223> OTHER INFORMATION: Synthetic Construct

<400> SEQUENCE: 205
ggatccatcg aaggtcgtca ctccgacgct gttttcaccg acaactacac gcgtctgcgt      60
aaacagctgg ctgctaagaa atacctgaac gacatcaaga aggtggcac ctaatgactc     120 gag                                                                   123

<210> SEQ ID NO 206
<211> LENGTH: 109
<212> TYPE: DNA
<213> ORGANISM: Artificial
<220> FEATURE:
<223> OTHER INFORMATION: Synthetic Construct

<400> SEQUENCE: 206
ggatccatcg aaggtcgtca ctccgacgct gttttcaccg acaactacac gcgtctgcgt      60
aaacagctgg ctgctaagaa atacctgaac gacatcaaga ataatgac                 109

<210> SEQ ID NO 207
<211> LENGTH: 114
<212> TYPE: DNA
<213> ORGANISM: Artificial
<220> FEATURE:
<223> OTHER INFORMATION: Synthetic Construct

<400> SEQUENCE: 207
```

```
ggatccatcg aaggtcgtca ctccgacgct gttttcaccg acaactacac gcgtctgcgt      60
aaacagatgg ctgttaagaa atacctgaat tccatcaaga ataatgact cgag             114

<210> SEQ ID NO 208
<211> LENGTH: 114
<212> TYPE: DNA
<213> ORGANISM: Artificial
<220> FEATURE:
<223> OTHER INFORMATION: Synthetic Construct

<400> SEQUENCE: 208
ggatccatcg aaggtcgtca ctccgacgct gttttcaccg acaactacac gcgtctgcgt      60
aaacagatgg ctgttaagaa atacctgaat tccatcaaga actaatgact cgag            114

<210> SEQ ID NO 209
<211> LENGTH: 114
<212> TYPE: DNA
<213> ORGANISM: Artificial
<220> FEATURE:
<223> OTHER INFORMATION: Synthetic Construct

<400> SEQUENCE: 209
ggatccatcg aaggtcgtca ctccgacgct gttttcaccg acaactacac gcgtctgcgt      60
aaacagatgg ctgttaagaa atacctgaat tccatcctga ataatgact cgag             114

<210> SEQ ID NO 210
<211> LENGTH: 114
<212> TYPE: DNA
<213> ORGANISM: Artificial
<220> FEATURE:
<223> OTHER INFORMATION: Synthetic Construct

<400> SEQUENCE: 210
ggatccatcg aaggtcgtca ctccgacgct gttttcaccg acaactacac ggaactgcgt      60
aaacagatgg ctgttaagaa atacctgaat tccatcctga actaatgact cgag            114

<210> SEQ ID NO 211
<211> LENGTH: 114
<212> TYPE: DNA
<213> ORGANISM: Artificial
<220> FEATURE:
<223> OTHER INFORMATION: Synthetic Construct

<400> SEQUENCE: 211
ggatccatcg aaggtcgtca ctccgacgct gttttcaccg acaactacac gcgtctgcgt      60
gaacagatgg ctgttaagaa atacctgaat tccatcctga actaatgact cgag            114

<210> SEQ ID NO 212
<211> LENGTH: 114
<212> TYPE: DNA
<213> ORGANISM: Artificial
<220> FEATURE:
<223> OTHER INFORMATION: Synthetic Construct

<400> SEQUENCE: 212
ggatccatcg aaggtcgtca ctccgacgct gttttcaccg acaactacac gcgtctgcgt      60
aaacagctgg ctgttaagaa atacctgaat tccatcctga actaatgact cgag            114

<210> SEQ ID NO 213
<211> LENGTH: 114
<212> TYPE: DNA
<213> ORGANISM: Artificial
```

```
<220> FEATURE:
<223> OTHER INFORMATION: Synthetic Construct

<400> SEQUENCE: 213
ggatccatcg aaggtcgtca ctccgacgct gttttcaccg acaactacac gcgtctgcgt      60
aaacagatgg ctgcaaagaa atacctgaat tccatcctga actaatgact cgag           114

<210> SEQ ID NO 214
<211> LENGTH: 114
<212> TYPE: DNA
<213> ORGANISM: Artificial
<220> FEATURE:
<223> OTHER INFORMATION: Synthetic Construct

<400> SEQUENCE: 214
ggatccatcg aaggtcgtca ctccgacgct gttttcaccg acaactacac gcgtctgcgt      60
aaacagatgg ctgttaagaa atacctgaat gacatcctga actaatgact cgag           114

<210> SEQ ID NO 215
<211> LENGTH: 114
<212> TYPE: DNA
<213> ORGANISM: Artificial
<220> FEATURE:
<223> OTHER INFORMATION: Synthetic Construct

<400> SEQUENCE: 215
ggatccatcg aaggtcgtca ctccgacgct gttttcaccg acaactacac gcgtctgcgt      60
aaacagatgg ctgcaaagaa atacctgaat tccatcaaga actaatgact cgag           114

<210> SEQ ID NO 216
<211> LENGTH: 114
<212> TYPE: DNA
<213> ORGANISM: Artificial
<220> FEATURE:
<223> OTHER INFORMATION: Synthetic Construct

<400> SEQUENCE: 216
ggatccatcg aaggtcgtca ctccgacgct gttttcaccg acaactacac gcgtctgcgt      60
aaacagatgg ctgcaaagaa atacctgaat tccatcctga ataatgact cgag            114

<210> SEQ ID NO 217
<211> LENGTH: 114
<212> TYPE: DNA
<213> ORGANISM: Artificial
<220> FEATURE:
<223> OTHER INFORMATION: Synthetic Construct

<400> SEQUENCE: 217
ggatccatcg aaggtcgtca ctccgacgct gttttcaccg acaactacac gcgtctgcgt      60
aaacagatgg ctgcaaagaa atacctgaat tccatcaaga ataatgact cgag            114

<210> SEQ ID NO 218
<211> LENGTH: 123
<212> TYPE: DNA
<213> ORGANISM: Artificial
<220> FEATURE:
<223> OTHER INFORMATION: Synthetic Construct

<400> SEQUENCE: 218
ggatccatcg aaggtcgtca ctccgacgct gttttcaccg acaactacac gcgtctgcgt      60
aaacagatgg ctgcaaagaa atacctgaat tccatcaaga aaaagcgtta ctaatgactc     120
``` gag                                                                      123

<210> SEQ ID NO 219
<211> LENGTH: 120
<212> TYPE: DNA
<213> ORGANISM: Artificial
<220> FEATURE:
<223> OTHER INFORMATION: Synthetic Construct

<400> SEQUENCE: 219
ggatccatcg aaggtcgtca ctccgacgct gttttcaccg acaactacac gcgtctgcgt    60
aaacagatgg ctgcaaagaa atacctgaat tccatcaaga aaaagcgtta atgactcgag   120

<210> SEQ ID NO 220
<211> LENGTH: 117
<212> TYPE: DNA
<213> ORGANISM: Artificial
<220> FEATURE:
<223> OTHER INFORMATION: Synthetic Construct

<400> SEQUENCE: 220
ggatccatcg aaggtcgtca ctccgacgct gttttcaccg acaactacac gcgtctgcgt    60
aaacagatgg ctgcaaagaa atacctgaat tccatcaaga aaagtaatg actcgag       117

<210> SEQ ID NO 221
<211> LENGTH: 123
<212> TYPE: DNA
<213> ORGANISM: Artificial
<220> FEATURE:
<223> OTHER INFORMATION: Synthetic Construct

<400> SEQUENCE: 221
ggatccatcg aaggtcgtca ctccgacgct gttttcaccg acaactacac gcgtctgcgt    60
aaacagatgg ctgcaaagaa atacctgaat tccatcaaga acaagcgtta ctaatgactc   120
gag                                                                  123

<210> SEQ ID NO 222
<211> LENGTH: 123
<212> TYPE: DNA
<213> ORGANISM: Artificial
<220> FEATURE:
<223> OTHER INFORMATION: Synthetic Construct

<400> SEQUENCE: 222
ggatccatcg aaggtcgtca ctccgacgct gttttcaccg acaactacac gcgtctgcgt    60
aaacagatgg ctgttaagaa atacctgaat tccatcaaga aaaagcgtta ctaatgactc   120
gag                                                                  123

<210> SEQ ID NO 223
<211> LENGTH: 120
<212> TYPE: DNA
<213> ORGANISM: Artificial
<220> FEATURE:
<223> OTHER INFORMATION: Synthetic Construct

<400> SEQUENCE: 223
ggatccatcg aaggtcgtca ctccgacgct gttttcaccg acaactacac gcgtctgcgt    60
aaacagatgg ctgttaagaa atacctgaat tccatcaaga aaaagcgtta atgactcgag   120

<210> SEQ ID NO 224
<211> LENGTH: 117

```
<212> TYPE: DNA
<213> ORGANISM: Artificial
<220> FEATURE:
<223> OTHER INFORMATION: Synthetic Construct

<400> SEQUENCE: 224
ggatccatcg aaggtcgtca ctccgacgct gttttcaccg acaactacac gcgtctgcgt      60
aaacagatgg ctgttaagaa atacctgaat tccatcaaga aaaagtaatg actcgag       117

<210> SEQ ID NO 225
<211> LENGTH: 123
<212> TYPE: DNA
<213> ORGANISM: Artificial
<220> FEATURE:
<223> OTHER INFORMATION: Synthetic Construct

<400> SEQUENCE: 225
ggatccatcg aaggtcgtca ctccgacgct gttttcaccg acaactacac gcgtctgcgt      60
aaacagatgg ctgttaagaa atacctgaat tccatcaaga acaagcgtta ctaatgactc     120
gag                                                                   123

<210> SEQ ID NO 226
<211> LENGTH: 114
<212> TYPE: DNA
<213> ORGANISM: Artificial
<220> FEATURE:
<223> OTHER INFORMATION: Synthetic Construct

<400> SEQUENCE: 226
ggatccatcg aaggtcgtca ctccgacgct gttttcaccg acaactacac gcgcttaaga      60
aaacaggttg ctgcaaagaa atacctgcag tccatcaaga ataatgact cgag            114

<210> SEQ ID NO 227
<211> LENGTH: 114
<212> TYPE: DNA
<213> ORGANISM: Artificial
<220> FEATURE:
<223> OTHER INFORMATION: Synthetic Construct

<400> SEQUENCE: 227
ggatccatcg aaggtcgtca ctccgacgct gttttcaccg acaactacac gcgcttaaga      60
aaacagatcg ctgcaaagaa atacctgcag actatcaaga ataatgact cgag            114

<210> SEQ ID NO 228
<211> LENGTH: 114
<212> TYPE: DNA
<213> ORGANISM: Artificial
<220> FEATURE:
<223> OTHER INFORMATION: Synthetic Construct

<400> SEQUENCE: 228
ggatccatcg aaggtcgtca ctccgacgct gttttcaccg acaactacac gcgcttaaga      60
aaacaggttg ctgcaaagaa atacctgaat tccatcaaga ataatgact cgag            114

<210> SEQ ID NO 229
<211> LENGTH: 120
<212> TYPE: DNA
<213> ORGANISM: Artificial
<220> FEATURE:
<223> OTHER INFORMATION: Synthetic Construct

<400> SEQUENCE: 229
```

```
ggatccatcg aaggtcgtca ctccgacgct gttttcaccg acaactacac gcgtctgcgt      60
aaacagatgg ctgcaaagaa atacctgaac tccatcaaga acaagcgtta atgagaattc     120
```

<210> SEQ ID NO 230
<211> LENGTH: 120
<212> TYPE: DNA
<213> ORGANISM: Artificial
<220> FEATURE:
<223> OTHER INFORMATION: Synthetic Construct

<400> SEQUENCE: 230

```
ggatccatcg aaggtcgtca ctccgacgct gttttcaccg acaactacac gcgtctgcgt      60
aaacagatgg ctgcaaagaa atacctgaac tccatcctga acaagcgtta atgagaattc     120
```

<210> SEQ ID NO 231
<211> LENGTH: 120
<212> TYPE: DNA
<213> ORGANISM: Artificial
<220> FEATURE:
<223> OTHER INFORMATION: Synthetic Construct

<400> SEQUENCE: 231

```
ggatccatcg aaggtcgtca ctccgacgct gttttcaccg acaactacac gcgcttaaga      60
aaacagatgg ctgacaagaa atacctgaac tccatcaaga acaagcgtta atgagaattc     120
```

<210> SEQ ID NO 232
<211> LENGTH: 120
<212> TYPE: DNA
<213> ORGANISM: Artificial
<220> FEATURE:
<223> OTHER INFORMATION: Synthetic Construct

<400> SEQUENCE: 232

```
ggatccatcg aaggtcgtca ctccgacgct gttttcaccg acaactacac gcgcttaaga      60
aaacagatgg ctgagaagaa atacctgaac tccatcaaga acaagcgtta atgagaattc     120
```

<210> SEQ ID NO 233
<211> LENGTH: 120
<212> TYPE: DNA
<213> ORGANISM: Artificial
<220> FEATURE:
<223> OTHER INFORMATION: Synthetic Construct

<400> SEQUENCE: 233

```
ggatccatcg aaggtcgtca ctccgacgct gttttcaccg acaactacac gcgcttaaga      60
aaacagatgg ctttcaagaa atacctgaac tccatcaaga acaagcgtta atgagaattc     120
```

<210> SEQ ID NO 234
<211> LENGTH: 120
<212> TYPE: DNA
<213> ORGANISM: Artificial
<220> FEATURE:
<223> OTHER INFORMATION: Synthetic Construct

<400> SEQUENCE: 234

```
ggatccatcg aaggtcgtca ctccgacgct gttttcaccg acaactacac gcgcttaaga      60
aaacagatgg ctgcaagaa atacctgaac tccatcaaga acaagcgtta atgagaattc      120
```

<210> SEQ ID NO 235
<211> LENGTH: 120
<212> TYPE: DNA
<213> ORGANISM: Artificial

```
<220> FEATURE:
<223> OTHER INFORMATION: Synthetic Construct

<400> SEQUENCE: 235
ggatccatcg aaggtcgtca ctccgacgct gttttcaccg acaactacac gcgcttaaga      60
aaacagatgg ctcacaagaa atacctgaac tccatcaaga acaagcgtta atgagaattc     120

<210> SEQ ID NO 236
<211> LENGTH: 120
<212> TYPE: DNA
<213> ORGANISM: Artificial
<220> FEATURE:
<223> OTHER INFORMATION: Synthetic Construct

<400> SEQUENCE: 236
ggatccatcg aaggtcgtca ctccgacgct gttttcaccg acaactacac gcgcttaaga      60
aaacagatgg ctatcaagaa atacctgaac tccatcaaga acaagcgtta atgagaattc     120

<210> SEQ ID NO 237
<211> LENGTH: 120
<212> TYPE: DNA
<213> ORGANISM: Artificial
<220> FEATURE:
<223> OTHER INFORMATION: Synthetic Construct

<400> SEQUENCE: 237
ggatccatcg aaggtcgtca ctccgacgct gttttcaccg acaactacac gcgcttaaga      60
aaacagatgg ctaaaaagaa atacctgaac tccatcaaga acaagcgtta atgagaattc     120

<210> SEQ ID NO 238
<211> LENGTH: 120
<212> TYPE: DNA
<213> ORGANISM: Artificial
<220> FEATURE:
<223> OTHER INFORMATION: Synthetic Construct

<400> SEQUENCE: 238
ggatccatcg aaggtcgtca ctccgacgct gttttcaccg acaactacac gcgcttaaga      60
aaacagatgg ctctgaagaa atacctgaac tccatcaaga acaagcgtta atgagaattc     120

<210> SEQ ID NO 239
<211> LENGTH: 120
<212> TYPE: DNA
<213> ORGANISM: Artificial
<220> FEATURE:
<223> OTHER INFORMATION: Synthetic Construct

<400> SEQUENCE: 239
ggatccatcg aaggtcgtca ctccgacgct gttttcaccg acaactacac gcgcttaaga      60
aaacagatgg ctatgaagaa atacctgaac tccatcaaga acaagcgtta atgagaattc     120

<210> SEQ ID NO 240
<211> LENGTH: 120
<212> TYPE: DNA
<213> ORGANISM: Artificial
<220> FEATURE:
<223> OTHER INFORMATION: Synthetic Construct

<400> SEQUENCE: 240
ggatccatcg aaggtcgtca ctccgacgct gttttcaccg acaactacac gcgcttaaga      60
aaacagatgg ctaacaagaa atacctgaac tccatcaaga acaagcgtta atgagaattc     120
```

<210> SEQ ID NO 241
<211> LENGTH: 120
<212> TYPE: DNA
<213> ORGANISM: Artificial
<220> FEATURE:
<223> OTHER INFORMATION: Synthetic Construct

<400> SEQUENCE: 241
ggatccatcg aaggtcgtca ctccgacgct gttttcaccg acaactacac gcgcttaaga      60
aaacagatgg ctccgaagaa atacctgaac tccatcaaga acaagcgtta atgagaattc     120

<210> SEQ ID NO 242
<211> LENGTH: 120
<212> TYPE: DNA
<213> ORGANISM: Artificial
<220> FEATURE:
<223> OTHER INFORMATION: Synthetic Construct

<400> SEQUENCE: 242
ggatccatcg aaggtcgtca ctccgacgct gttttcaccg acaactacac gcgcttaaga      60
aaacagatgg ctcagaagaa atacctgaac tccatcaaga acaagcgtta atgagaattc     120

<210> SEQ ID NO 243
<211> LENGTH: 120
<212> TYPE: DNA
<213> ORGANISM: Artificial
<220> FEATURE:
<223> OTHER INFORMATION: Synthetic Construct

<400> SEQUENCE: 243
ggatccatcg aaggtcgtca ctccgacgct gttttcaccg acaactacac gcgcttaaga      60
aaacagatgg ctcgcaagaa atacctgaac tccatcaaga acaagcgtta atgagaattc     120

<210> SEQ ID NO 244
<211> LENGTH: 120
<212> TYPE: DNA
<213> ORGANISM: Artificial
<220> FEATURE:
<223> OTHER INFORMATION: Synthetic Construct

<400> SEQUENCE: 244
ggatccatcg aaggtcgtca ctccgacgct gttttcaccg acaactacac gcgcttaaga      60
aaacagatgg cttccaagaa atacctgaac tccatcaaga acaagcgtta atgagaattc     120

<210> SEQ ID NO 245
<211> LENGTH: 120
<212> TYPE: DNA
<213> ORGANISM: Artificial
<220> FEATURE:
<223> OTHER INFORMATION: Synthetic Construct

<400> SEQUENCE: 245
ggatccatcg aaggtcgtca ctccgacgct gttttcaccg acaactacac gcgcttaaga      60
aaacagatgg ctaccaagaa atacctgaac tccatcaaga acaagcgtta atgagaattc     120

<210> SEQ ID NO 246
<211> LENGTH: 120
<212> TYPE: DNA
<213> ORGANISM: Artificial
<220> FEATURE:
<223> OTHER INFORMATION: Synthetic Construct

<400> SEQUENCE: 246

```
ggatccatcg aaggtcgtca ctccgacgct gttttcaccg acaactacac gcgcttaaga    60
aaacagatgg ctgtgaagaa atacctgaac tccatcaaga acaagcgtta atgagaattc   120
```

<210> SEQ ID NO 247
<211> LENGTH: 120
<212> TYPE: DNA
<213> ORGANISM: Artificial
<220> FEATURE:
<223> OTHER INFORMATION: Synthetic Construct

<400> SEQUENCE: 247

```
ggatccatcg aaggtcgtca ctccgacgct gttttcaccg acaactacac gcgcttaaga    60
aaacagatgg cttggaagaa atacctgaac tccatcaaga acaagcgtta atgagaattc   120
```

<210> SEQ ID NO 248
<211> LENGTH: 120
<212> TYPE: DNA
<213> ORGANISM: Artificial
<220> FEATURE:
<223> OTHER INFORMATION: Synthetic Construct

<400> SEQUENCE: 248

```
ggatccatcg aaggtcgtca ctccgacgct gttttcaccg acaactacac gcgcttaaga    60
aaacagatgg cttacaagaa atacctgaac tccatcaaga acaagcgtta atgagaattc   120
```

<210> SEQ ID NO 249
<211> LENGTH: 120
<212> TYPE: DNA
<213> ORGANISM: Artificial
<220> FEATURE:
<223> OTHER INFORMATION: Synthetic Construct

<400> SEQUENCE: 249

```
ggatccatcg aaggtcgtca ctccgacgct gttttcaccg acaactacac gcgtctgcgt    60
aaacagatgg ctgcaaagaa atacctgaac tccatcgcga acaagcgtta atgagaattc   120
```

<210> SEQ ID NO 250
<211> LENGTH: 120
<212> TYPE: DNA
<213> ORGANISM: Artificial
<220> FEATURE:
<223> OTHER INFORMATION: Synthetic Construct

<400> SEQUENCE: 250

```
ggatccatcg aaggtcgtca ctccgacgct gttttcaccg acaactacac gcgtctgcgt    60
aaacagatgg ctgcaaagaa atacctgaac tccatcgaca acaagcgtta atgagaattc   120
```

<210> SEQ ID NO 251
<211> LENGTH: 120
<212> TYPE: DNA
<213> ORGANISM: Artificial
<220> FEATURE:
<223> OTHER INFORMATION: Synthetic Construct

<400> SEQUENCE: 251

```
ggatccatcg aaggtcgtca ctccgacgct gttttcaccg acaactacac gcgtctgcgt    60
aaacagatgg ctgcaaagaa atacctgaac tccatcgaga acaagcgtta atgagaattc   120
```

<210> SEQ ID NO 252
<211> LENGTH: 120
<212> TYPE: DNA

<213> ORGANISM: Artificial
<220> FEATURE:
<223> OTHER INFORMATION: Synthetic Construct

<400> SEQUENCE: 252
ggatccatcg aaggtcgtca ctccgacgct gttttcaccg acaactacac gcgtctgcgt    60
aaacagatgg ctgcaaagaa atacctgaac tccatcttca acaagcgtta atgagaattc   120

<210> SEQ ID NO 253
<211> LENGTH: 119
<212> TYPE: DNA
<213> ORGANISM: Artificial
<220> FEATURE:
<223> OTHER INFORMATION: Synthetic Construct

<400> SEQUENCE: 253
ggatccatcg aaggtcgtca ctccgacgct gttttcaccg acaactacac gcgtctgcgt    60
aaacagatgg ctgcaaagaa atacctgaac tccatcggca acaagcgtta agagaattc    119

<210> SEQ ID NO 254
<211> LENGTH: 120
<212> TYPE: DNA
<213> ORGANISM: Artificial
<220> FEATURE:
<223> OTHER INFORMATION: Synthetic Construct

<400> SEQUENCE: 254
ggatccatcg aaggtcgtca ctccgacgct gttttcaccg acaactacac gcgtctgcgt    60
aaacagatgg ctgcaaagaa atacctgaac tccatccaca acaagcgtta atgagaattc   120

<210> SEQ ID NO 255
<211> LENGTH: 120
<212> TYPE: DNA
<213> ORGANISM: Artificial
<220> FEATURE:
<223> OTHER INFORMATION: Synthetic Construct

<400> SEQUENCE: 255
ggatccatcg aaggtcgtca ctccgacgct gttttcaccg acaactacac gcgtctgcgt    60
aaacagatgg ctgcaaagaa atacctgaac tccatcatca acaagcgtta atgagaattc   120

<210> SEQ ID NO 256
<211> LENGTH: 120
<212> TYPE: DNA
<213> ORGANISM: Artificial
<220> FEATURE:
<223> OTHER INFORMATION: Synthetic Construct

<400> SEQUENCE: 256
ggatccatcg aaggtcgtca ctccgacgct gttttcaccg acaactacac gcgtctgcgt    60
aaacagatgg ctgcaaagaa atacctgaac tccatcatga acaagcgtta atgagaattc   120

<210> SEQ ID NO 257
<211> LENGTH: 120
<212> TYPE: DNA
<213> ORGANISM: Artificial
<220> FEATURE:
<223> OTHER INFORMATION: Synthetic Construct

<400> SEQUENCE: 257
ggatccatcg aaggtcgtca ctccgacgct gttttcaccg acaactacac gcgtctgcgt    60
aaacagatgg ctgcaaagaa atacctgaac tccatcaaca acaagcgtta atgagaattc   120

<210> SEQ ID NO 258
<211> LENGTH: 120
<212> TYPE: DNA
<213> ORGANISM: Artificial
<220> FEATURE:
<223> OTHER INFORMATION: Synthetic Construct

<400> SEQUENCE: 258
ggatccatcg aaggtcgtca ctccgacgct gttttcaccg acaactacac gcgtctgcgt    60
aaacagatgg ctgcaaagaa atacctgaac tccatcccga caagcgtta atgagaattc   120

<210> SEQ ID NO 259
<211> LENGTH: 120
<212> TYPE: DNA
<213> ORGANISM: Artificial
<220> FEATURE:
<223> OTHER INFORMATION: Synthetic Construct

<400> SEQUENCE: 259
ggatccatcg aaggtcgtca ctccgacgct gttttcaccg acaactacac gcgtctgcgt    60
aaacagatgg ctgcaaagaa atacctgaac tccatccaga acaagcgtta atgagaattc   120

<210> SEQ ID NO 260
<211> LENGTH: 120
<212> TYPE: DNA
<213> ORGANISM: Artificial
<220> FEATURE:
<223> OTHER INFORMATION: Synthetic Construct

<400> SEQUENCE: 260
ggatccatcg aaggtcgtca ctccgacgct gttttcaccg acaactacac gcgtctgcgt    60
aaacagatgg ctgcaaagaa atacctgaac tccatcagga acaagcgtta atgagaattc   120

<210> SEQ ID NO 261
<211> LENGTH: 120
<212> TYPE: DNA
<213> ORGANISM: Artificial
<220> FEATURE:
<223> OTHER INFORMATION: Synthetic Construct

<400> SEQUENCE: 261
ggatccatcg aaggtcgtca ctccgacgct gttttcaccg acaactacac gcgtctgcgt    60
aaacagatgg ctgcaaagaa atacctgaac tccatcagca acaagcgtta atgagaattc   120

<210> SEQ ID NO 262
<211> LENGTH: 120
<212> TYPE: DNA
<213> ORGANISM: Artificial
<220> FEATURE:
<223> OTHER INFORMATION: Synthetic Construct

<400> SEQUENCE: 262
ggatccatcg aaggtcgtca ctccgacgct gttttcaccg acaactacac gcgtctgcgt    60
aaacagatgg ctgcaaagaa atacctgaac tccatcacga acaagcgtta atgagaattc   120

<210> SEQ ID NO 263
<211> LENGTH: 120
<212> TYPE: DNA
<213> ORGANISM: Artificial
<220> FEATURE:
<223> OTHER INFORMATION: Synthetic Construct

<400> SEQUENCE: 263
ggatccatcg aaggtcgtca ctccgacgct gttttcaccg acaactacac gcgtctgcgt      60
aaacagatgg ctgcaaagaa atacctgaac tccatcgtga acaagcgtta atgagaattc     120

<210> SEQ ID NO 264
<211> LENGTH: 120
<212> TYPE: DNA
<213> ORGANISM: Artificial
<220> FEATURE:
<223> OTHER INFORMATION: Synthetic Construct

<400> SEQUENCE: 264
ggatccatcg aaggtcgtca ctccgacgct gttttcaccg acaactacac gcgtctgcgt      60
aaacagatgg ctgcaaagaa atacctgaac tccatctgga acaagcgtta atgagaattc     120

<210> SEQ ID NO 265
<211> LENGTH: 120
<212> TYPE: DNA
<213> ORGANISM: Artificial
<220> FEATURE:
<223> OTHER INFORMATION: Synthetic Construct

<400> SEQUENCE: 265
ggatccatcg aaggtcgtca ctccgacgct gttttcaccg acaactacac gcgtctgcgt      60
aaacagatgg ctgcaaagaa atacctgaac tccatctaca acaagcgtta atgagaattc     120

<210> SEQ ID NO 266
<211> LENGTH: 120
<212> TYPE: DNA
<213> ORGANISM: Artificial
<220> FEATURE:
<223> OTHER INFORMATION: Synthetic Construct

<400> SEQUENCE: 266
ggatccatcg aaggtcgtca ctccgacgct gttttcaccg acaactacac gcgtctgcgt      60
aaacagatgg ctgcaaagaa atacctgaac tccatcaaga acgcgcgtta atgagaattc     120

<210> SEQ ID NO 267
<211> LENGTH: 120
<212> TYPE: DNA
<213> ORGANISM: Artificial
<220> FEATURE:
<223> OTHER INFORMATION: Synthetic Construct

<400> SEQUENCE: 267
ggatccatcg aaggtcgtca ctccgacgct gttttcaccg acaactacac gcgtctgcgt      60
aaacagatgg ctgcaaagaa atacctgaac tccatcaaga acgaccgtta atgagaattc     120

<210> SEQ ID NO 268
<211> LENGTH: 120
<212> TYPE: DNA
<213> ORGANISM: Artificial
<220> FEATURE:
<223> OTHER INFORMATION: Synthetic Construct

<400> SEQUENCE: 268
ggatccatcg aaggtcgtca ctccgacgct gttttcaccg acaactacac gcgtctgcgt      60
aaacagatgg ctgcaaagaa atacctgaac tccatcaaga acgaacgtta atgagaattc     120

<210> SEQ ID NO 269
<211> LENGTH: 120

```
<212> TYPE: DNA
<213> ORGANISM: Artificial
<220> FEATURE:
<223> OTHER INFORMATION: Synthetic Construct

<400> SEQUENCE: 269
ggatccatcg aaggtcgtca ctccgacgct gttttcaccg acaactacac gcgtctgcgt      60
aaacagatgg ctgcaaagaa atacctgaac tccatcaaga acttccgtta atgagaattc     120

<210> SEQ ID NO 270
<211> LENGTH: 120
<212> TYPE: DNA
<213> ORGANISM: Artificial
<220> FEATURE:
<223> OTHER INFORMATION: Synthetic Construct

<400> SEQUENCE: 270
ggatccatcg aaggtcgtca ctccgacgct gttttcaccg acaactacac gcgtctgcgt      60
aaacagatgg ctgcaaagaa atacctgaac tccatcaaga acggccgtta atgagaattc     120

<210> SEQ ID NO 271
<211> LENGTH: 120
<212> TYPE: DNA
<213> ORGANISM: Artificial
<220> FEATURE:
<223> OTHER INFORMATION: Synthetic Construct

<400> SEQUENCE: 271
ggatccatcg aaggtcgtca ctccgacgct gttttcaccg acaactacac gcgtctgcgt      60
aaacagatgg ctgcaaagaa atacctgaac tccatcaaga accaccgtta atgagaattc     120

<210> SEQ ID NO 272
<211> LENGTH: 120
<212> TYPE: DNA
<213> ORGANISM: Artificial
<220> FEATURE:
<223> OTHER INFORMATION: Synthetic Construct

<400> SEQUENCE: 272
ggatccatcg aaggtcgtca ctccgacgct gttttcaccg acaactacac gcgtctgcgt      60
aaacagatgg ctgcaaagaa atacctgaac tccatcaaga acatccgtta atgagaattc     120

<210> SEQ ID NO 273
<211> LENGTH: 120
<212> TYPE: DNA
<213> ORGANISM: Artificial
<220> FEATURE:
<223> OTHER INFORMATION: Synthetic Construct

<400> SEQUENCE: 273
ggatccatcg aaggtcgtca ctccgacgct gttttcaccg acaactacac gcgtctgcgt      60
aaacagatgg ctgcaaagaa atacctgaac tccatcaaga acctgcgtta atgagaattc     120

<210> SEQ ID NO 274
<211> LENGTH: 120
<212> TYPE: DNA
<213> ORGANISM: Artificial
<220> FEATURE:
<223> OTHER INFORMATION: Synthetic Construct

<400> SEQUENCE: 274
ggatccatcg aaggtcgtca ctccgacgct gttttcaccg acaactacac gcgtctgcgt      60
```
aaacagatgg ctgcaaagaa atacctgaac tccatcaaga acatgcgtta atgagaattc    120

<210> SEQ ID NO 275
<211> LENGTH: 120
<212> TYPE: DNA
<213> ORGANISM: Artificial
<220> FEATURE:
<223> OTHER INFORMATION: Synthetic Construct

<400> SEQUENCE: 275
ggatccatcg aaggtcgtca ctccgacgct gttttcaccg acaactacac gcgtctgcgt    60
aaacagatgg ctgcaaagaa atacctgaac tccatcaaga acaaccgtta atgagaattc    120

<210> SEQ ID NO 276
<211> LENGTH: 120
<212> TYPE: DNA
<213> ORGANISM: Artificial
<220> FEATURE:
<223> OTHER INFORMATION: Synthetic Construct

<400> SEQUENCE: 276
ggatccatcg aaggtcgtca ctccgacgct gttttcaccg acaactacac gcgtctgcgt    60
aaacagatgg ctgcaaagaa atacctgaac tccatcaaga acccgcgtta atgagaattc    120

<210> SEQ ID NO 277
<211> LENGTH: 120
<212> TYPE: DNA
<213> ORGANISM: Artificial
<220> FEATURE:
<223> OTHER INFORMATION: Synthetic Construct

<400> SEQUENCE: 277
ggatccatcg aaggtcgtca ctccgacgct gttttcaccg acaactacac gcgtctgcgt    60
aaacagatgg ctgcaaagaa atacctgaac tccatcaaga accagcgtta atgagaattc    120

<210> SEQ ID NO 278
<211> LENGTH: 120
<212> TYPE: DNA
<213> ORGANISM: Artificial
<220> FEATURE:
<223> OTHER INFORMATION: Synthetic Construct

<400> SEQUENCE: 278
ggatccatcg aaggtcgtca ctccgacgct gttttcaccg acaactacac gcgtctgcgt    60
aaacagatgg ctgcaaagaa atacctgaac tccatcaaga accgccgtta atgagaattc    120

<210> SEQ ID NO 279
<211> LENGTH: 120
<212> TYPE: DNA
<213> ORGANISM: Artificial
<220> FEATURE:
<223> OTHER INFORMATION: Synthetic Construct

<400> SEQUENCE: 279
ggatccatcg aaggtcgtca ctccgacgct gttttcaccg acaactacac gcgtctgcgt    60
aaacagatgg ctgcaaagaa atacctgaac tccatcaaga acagccgtta atgagaattc    120

<210> SEQ ID NO 280
<211> LENGTH: 120
<212> TYPE: DNA
<213> ORGANISM: Artificial
<220> FEATURE:
<223> OTHER INFORMATION: Synthetic Construct

<400> SEQUENCE: 280
ggatccatcg aaggtcgtca ctccgacgct gttttcaccg acaactacac gcgtctgcgt        60
aaacagatgg ctgcaaagaa atacctgaac tccatcaaga acacccgtta atgagaattc       120

<210> SEQ ID NO 281
<211> LENGTH: 119
<212> TYPE: DNA
<213> ORGANISM: Artificial
<220> FEATURE:
<223> OTHER INFORMATION: Synthetic Construct

<400> SEQUENCE: 281
gatccatcga aggtcgtcac tccgacgctg ttttcaccga caactacacg cgtctgcgta        60
aacagatggc tgcaaagaaa tacctgaact ccatcaagaa cgtgcgttaa tgagaattc       119

<210> SEQ ID NO 282
<211> LENGTH: 120
<212> TYPE: DNA
<213> ORGANISM: Artificial
<220> FEATURE:
<223> OTHER INFORMATION: Synthetic Construct

<400> SEQUENCE: 282
ggatccatcg aaggtcgtca ctccgacgct gttttcaccg acaactacac gcgtctgcgt        60
aaacagatgg ctgcaaagaa atacctgaac tccatcaaga actggcgtta atgagaattc       120

<210> SEQ ID NO 283
<211> LENGTH: 120
<212> TYPE: DNA
<213> ORGANISM: Artificial
<220> FEATURE:
<223> OTHER INFORMATION: Synthetic Construct

<400> SEQUENCE: 283
ggatccatcg aaggtcgtca ctccgacgct gttttcaccg acaactacac gcgtctgcgt        60
aaacagatgg ctgcaaagaa atacctgaac tccatcaaga actaccgtta atgagaattc       120

<210> SEQ ID NO 284
<211> LENGTH: 120
<212> TYPE: DNA
<213> ORGANISM: Artificial
<220> FEATURE:
<223> OTHER INFORMATION: Synthetic Construct

<400> SEQUENCE: 284
ggatccatcg aaggtcgtca ctccgacgct gttttcaccg acaactacac gcgtctgcgt        60
aaacagatgg ctgcaaagaa atacctgaac tccatcaaga acaaggcgta atgagaattc       120

<210> SEQ ID NO 285
<211> LENGTH: 120
<212> TYPE: DNA
<213> ORGANISM: Artificial
<220> FEATURE:
<223> OTHER INFORMATION: Synthetic Construct

<400> SEQUENCE: 285
ggatccatcg aaggtcgtca ctccgacgct gttttcaccg acaactacac gcgtctgcgt        60
aaacagatgg ctgcaaagaa atacctgaac tccatcaaga acaaggacta atgagaattc       120

<210> SEQ ID NO 286

```
<211> LENGTH: 119
<212> TYPE: DNA
<213> ORGANISM: Artificial
<220> FEATURE:
<223> OTHER INFORMATION: Synthetic Construct

<400> SEQUENCE: 286
ggatccatcg aaggtcgtca ctccgacgct gttttcaccg acaactacac gcgtctgcgt      60
aaacagatgg ctgcaaagaa atacctgaac tccatcaaga acaaggagta agagaattc     119

<210> SEQ ID NO 287
<211> LENGTH: 120
<212> TYPE: DNA
<213> ORGANISM: Artificial
<220> FEATURE:
<223> OTHER INFORMATION: Synthetic Construct

<400> SEQUENCE: 287
ggatccatcg aaggtcgtca ctccgacgct gttttcaccg acaactacac gcgtctgcgt      60
aaacagatgg ctgcaaagaa atacctgaac tccatcaaga acaagttcta atgagaattc    120

<210> SEQ ID NO 288
<211> LENGTH: 120
<212> TYPE: DNA
<213> ORGANISM: Artificial
<220> FEATURE:
<223> OTHER INFORMATION: Synthetic Construct

<400> SEQUENCE: 288
ggatccatcg aaggtcgtca ctccgacgct gttttcaccg acaactacac gcgtctgcgt      60
aaacagatgg ctgcaaagaa atacctgaac tccatcaaga acaaggccta atgagaattc    120

<210> SEQ ID NO 289
<211> LENGTH: 120
<212> TYPE: DNA
<213> ORGANISM: Artificial
<220> FEATURE:
<223> OTHER INFORMATION: Synthetic Construct

<400> SEQUENCE: 289
ggatccatcg aaggtcgtca ctccgacgct gttttcaccg acaactacac gcgtctgcgt      60
aaacagatgg ctgcaaagaa atacctgaac tccatcaaga acaagcacta atgagaattc    120

<210> SEQ ID NO 290
<211> LENGTH: 120
<212> TYPE: DNA
<213> ORGANISM: Artificial
<220> FEATURE:
<223> OTHER INFORMATION: Synthetic Construct

<400> SEQUENCE: 290
ggatccatcg aaggtcgtca ctccgacgct gttttcaccg acaactacac gcgtctgcgt      60
aaacagatgg ctgcaaagaa atacctgaac tccatcaaga acaagatcta atgagaattc    120

<210> SEQ ID NO 291
<211> LENGTH: 120
<212> TYPE: DNA
<213> ORGANISM: Artificial
<220> FEATURE:
<223> OTHER INFORMATION: Synthetic Construct

<400> SEQUENCE: 291
ggatccatcg aaggtcgtca ctccgacgct gttttcaccg acaactacac gcgtctgcgt      60
```
aaacagatgg ctgcaaagaa atacctgaac tccatcaaga acaagaagta atgagaattc      120

<210> SEQ ID NO 292
<211> LENGTH: 120
<212> TYPE: DNA
<213> ORGANISM: Artificial
<220> FEATURE:
<223> OTHER INFORMATION: Synthetic Construct

<400> SEQUENCE: 292
ggatccatcg aaggtcgtca ctccgacgct gttttcaccg acaactacac gcgtctgcgt      60
aaacagatgg ctgcaaagaa atacctgaac tccatcaaga acaagctgta atgagaattc      120

<210> SEQ ID NO 293
<211> LENGTH: 120
<212> TYPE: DNA
<213> ORGANISM: Artificial
<220> FEATURE:
<223> OTHER INFORMATION: Synthetic Construct

<400> SEQUENCE: 293
ggatccatcg aaggtcgtca ctccgacgct gttttcaccg acaactacac gcgtctgcgt      60
aaacagatgg ctgcaaagaa atacctgaac tccatcaaga acaagatgta atgagaattc      120

<210> SEQ ID NO 294
<211> LENGTH: 120
<212> TYPE: DNA
<213> ORGANISM: Artificial
<220> FEATURE:
<223> OTHER INFORMATION: Synthetic Construct

<400> SEQUENCE: 294
ggatccatcg aaggtcgtca ctccgacgct gttttcaccg acaactacac gcgtctgcgt      60
aaacagatgg ctgcaaagaa atacctgaac tccatcaaga acaagaacta atgagaattc      120

<210> SEQ ID NO 295
<211> LENGTH: 120
<212> TYPE: DNA
<213> ORGANISM: Artificial
<220> FEATURE:
<223> OTHER INFORMATION: Synthetic Construct

<400> SEQUENCE: 295
ggatccatcg aaggtcgtca ctccgacgct gttttcaccg acaactacac gcgtctgcgt      60
aaacagatgg ctgcaaagaa atacctgaac tccatcaaga acaagccgta atgagaattc      120

<210> SEQ ID NO 296
<211> LENGTH: 120
<212> TYPE: DNA
<213> ORGANISM: Artificial
<220> FEATURE:
<223> OTHER INFORMATION: Synthetic Construct

<400> SEQUENCE: 296
ggatccatcg aaggtcgtca ctccgacgct gttttcaccg acaactacac gcgtctgcgt      60
aaacagatgg ctgcaaagaa atacctgaac tccatcaaga acaagcagta atgagaattc      120

<210> SEQ ID NO 297
<211> LENGTH: 120
<212> TYPE: DNA
<213> ORGANISM: Artificial
<220> FEATURE:

<223> OTHER INFORMATION: Synthetic Construct

<400> SEQUENCE: 297
ggatccatcg aaggtcgtca ctccgacgct gttttcaccg acaactacac gcgtctgcgt    60
aaacagatgg ctgcaaagaa atacctgaac tccatcaaga acaagagcta atgagaattc   120

<210> SEQ ID NO 298
<211> LENGTH: 120
<212> TYPE: DNA
<213> ORGANISM: Artificial
<220> FEATURE:
<223> OTHER INFORMATION: Synthetic Construct

<400> SEQUENCE: 298
ggatccatcg aaggtcgtca ctccgacgct gttttcaccg acaactacac gcgtctgcgt    60
aaacagatgg ctgcaaagaa atacctgaac tccatcaaga acaagaccta atgagaattc   120

<210> SEQ ID NO 299
<211> LENGTH: 120
<212> TYPE: DNA
<213> ORGANISM: Artificial
<220> FEATURE:
<223> OTHER INFORMATION: Synthetic Construct

<400> SEQUENCE: 299
ggatccatcg aaggtcgtca ctccgacgct gttttcaccg acaactacac gcgtctgcgt    60
aaacagatgg ctgcaaagaa atacctgaac tccatcaaga acaaggtgta atgagaattc   120

<210> SEQ ID NO 300
<211> LENGTH: 120
<212> TYPE: DNA
<213> ORGANISM: Artificial
<220> FEATURE:
<223> OTHER INFORMATION: Synthetic Construct

<400> SEQUENCE: 300
ggatccatcg aaggtcgtca ctccgacgct gttttcaccg acaactacac gcgtctgcgt    60
aaacagatgg ctgcaaagaa atacctgaac tccatcaaga acaagtggta atgagaattc   120

<210> SEQ ID NO 301
<211> LENGTH: 120
<212> TYPE: DNA
<213> ORGANISM: Artificial
<220> FEATURE:
<223> OTHER INFORMATION: Synthetic Construct

<400> SEQUENCE: 301
ggatccatcg aaggtcgtca ctccgacgct gttttcaccg acaactacac gcgtctgcgt    60
aaacagatgg ctgcaaagaa atacctgaac tccatcaaga acaagtacta atgagaattc   120

<210> SEQ ID NO 302
<211> LENGTH: 120
<212> TYPE: DNA
<213> ORGANISM: Artificial
<220> FEATURE:
<223> OTHER INFORMATION: Synthetic Construct

<400> SEQUENCE: 302
ggatccatcg aaggtcgtca ctccgacgct gttttcaccg acaactacac gcgtctgcgt    60
aaacagatgg ctgcaaagaa atacctgaac tccatcaaga accgtatcta atgagaattc   120

<210> SEQ ID NO 303
<211> LENGTH: 120
<212> TYPE: DNA
<213> ORGANISM: Artificial
<220> FEATURE:
<223> OTHER INFORMATION: Synthetic Construct

<400> SEQUENCE: 303
ggatccatcg aaggtcgtca ctccgacgct gttttcaccg acaactacac gcgtctgcgt      60
aaacagatgg ctggcaagaa atacctgaac tccatcaaga accgtatcta atgagaattc     120

<210> SEQ ID NO 304
<211> LENGTH: 120
<212> TYPE: DNA
<213> ORGANISM: Artificial
<220> FEATURE:
<223> OTHER INFORMATION: Synthetic Construct

<400> SEQUENCE: 304
ggatccatcg aaggtcgtca ctccgacgct gttttcaccg acaactacac gcgtctgcgt      60
aaacagatgg ctaaaaagaa atacctgaac tccatcaaga accgtatcta atgagaattc     120

<210> SEQ ID NO 305
<211> LENGTH: 120
<212> TYPE: DNA
<213> ORGANISM: Artificial
<220> FEATURE:
<223> OTHER INFORMATION: Synthetic Construct

<400> SEQUENCE: 305
ggatccatcg aaggtcgtca ctccgacgct gttttcaccg acaactacac gcgtctgcgt      60
aaacagatgg ctcgcaagaa atacctgaac tccatcaaga accgtatcta atgagaattc     120

<210> SEQ ID NO 306
<211> LENGTH: 120
<212> TYPE: DNA
<213> ORGANISM: Artificial
<220> FEATURE:
<223> OTHER INFORMATION: Synthetic Construct

<400> SEQUENCE: 306
ggatccatcg aaggtcgtca ctccgacgct gttttcaccg acaactacac gcgtctgcgt      60
aaacagatgg cttccaagaa atacctgaac tccatcaaga accgtatcta atgagaattc     120

<210> SEQ ID NO 307
<211> LENGTH: 120
<212> TYPE: DNA
<213> ORGANISM: Artificial
<220> FEATURE:
<223> OTHER INFORMATION: Synthetic Construct

<400> SEQUENCE: 307
ggatccatcg aaggtcgtca ctccgacgct gttttcaccg acaactacac gcgtctgcgt      60
aaacagatgg ctgcaaagaa atacctgaac tccatcccga accgtatcta atgagaattc     120

<210> SEQ ID NO 308
<211> LENGTH: 120
<212> TYPE: DNA
<213> ORGANISM: Artificial
<220> FEATURE:
<223> OTHER INFORMATION: Synthetic Construct

<400> SEQUENCE: 308

```
ggatccatcg aaggtcgtca ctccgacgct gttttcaccg acaactacac gcgtctgcgt    60
aaacagatgg ctggcaagaa atacctgaac tccatcccga accgtatcta atgagaattc   120
```

<210> SEQ ID NO 309
<211> LENGTH: 120
<212> TYPE: DNA
<213> ORGANISM: Artificial
<220> FEATURE:
<223> OTHER INFORMATION: Synthetic Construct

<400> SEQUENCE: 309

```
ggatccatcg aaggtcgtca ctccgacgct gttttcaccg acaactacac gcgtctgcgt    60
aaacagatgg ctaaaaagaa atacctgaac tccatcccga accgtatcta atgagaattc   120
```

<210> SEQ ID NO 310
<211> LENGTH: 120
<212> TYPE: DNA
<213> ORGANISM: Artificial
<220> FEATURE:
<223> OTHER INFORMATION: Synthetic Construct

<400> SEQUENCE: 310

```
ggatccatcg aaggtcgtca ctccgacgct gttttcaccg acaactacac gcgtctgcgt    60
aaacagatgg ctcgcaagaa atacctgaac tccatcccga accgtatcta atgagaattc   120
```

<210> SEQ ID NO 311
<211> LENGTH: 120
<212> TYPE: DNA
<213> ORGANISM: Artificial
<220> FEATURE:
<223> OTHER INFORMATION: Synthetic Construct

<400> SEQUENCE: 311

```
ggatccatcg aaggtcgtca ctccgacgct gttttcaccg acaactacac gcgtctgcgt    60
aaacagatgg cttccaagaa atacctgaac tccatcccga accgtatcta atgagaattc   120
```

<210> SEQ ID NO 312
<211> LENGTH: 120
<212> TYPE: DNA
<213> ORGANISM: Artificial
<220> FEATURE:
<223> OTHER INFORMATION: Synthetic Construct

<400> SEQUENCE: 312

```
ggatccatcg aaggtcgtca ctccgacgct gttttcaccg acaactacac gcgtctgcgt    60
aaacagatgg ctgcaaagaa atacctgaac tccatccaga accgtatcta atgagaattc   120
```

<210> SEQ ID NO 313
<211> LENGTH: 120
<212> TYPE: DNA
<213> ORGANISM: Artificial
<220> FEATURE:
<223> OTHER INFORMATION: Synthetic Construct

<400> SEQUENCE: 313

```
ggatccatcg aaggtcgtca ctccgacgct gttttcaccg acaactacac gcgtctgcgt    60
aaacagatgg ctggcaagaa atacctgaac tccatccaga accgtatcta atgagaattc   120
```

<210> SEQ ID NO 314
<211> LENGTH: 120
<212> TYPE: DNA
<213> ORGANISM: Artificial
<220> FEATURE:
<223> OTHER INFORMATION: Synthetic Construct

<400> SEQUENCE: 314
ggatccatcg aaggtcgtca ctccgacgct gttttcaccg acaactacac gcgtctgcgt    60
aaacagatgg ctaaaaagaa atacctgaac tccatccaga accgtatcta atgagaattc   120

<210> SEQ ID NO 315
<211> LENGTH: 120
<212> TYPE: DNA
<213> ORGANISM: Artificial
<220> FEATURE:
<223> OTHER INFORMATION: Synthetic Construct

<400> SEQUENCE: 315
ggatccatcg aaggtcgtca ctccgacgct gttttcaccg acaactacac gcgtctgcgt    60
aaacagatgg ctcgcaagaa atacctgaac tccatccaga accgtatcta atgagaattc   120

<210> SEQ ID NO 316
<211> LENGTH: 120
<212> TYPE: DNA
<213> ORGANISM: Artificial
<220> FEATURE:
<223> OTHER INFORMATION: Synthetic Construct

<400> SEQUENCE: 316
ggatccatcg aaggtcgtca ctccgacgct gttttcaccg acaactacac gcgtctgcgt    60
aaacagatgg cttccaagaa atacctgaac tccatccaga accgtatcta atgagaattc   120

<210> SEQ ID NO 317
<211> LENGTH: 120
<212> TYPE: DNA
<213> ORGANISM: Artificial
<220> FEATURE:
<223> OTHER INFORMATION: Synthetic Construct

<400> SEQUENCE: 317
ggatccatcg aaggtcgtca ctccgacgct gttttcaccg acaactacac gcgtctgcgt    60
aaacagatgg ctgcaaagaa atacctgaac tccatccgta accgtatcta atgagaattc   120

<210> SEQ ID NO 318
<211> LENGTH: 120
<212> TYPE: DNA
<213> ORGANISM: Artificial
<220> FEATURE:
<223> OTHER INFORMATION: Synthetic Construct

<400> SEQUENCE: 318
ggatccatcg aaggtcgtca ctccgacgct gttttcaccg acaactacac gcgtctgcgt    60
aaacagatgg ctggcaagaa atacctgaac tccatccgta accgtatcta atgagaattc   120

<210> SEQ ID NO 319
<211> LENGTH: 120
<212> TYPE: DNA
<213> ORGANISM: Artificial
<220> FEATURE:
<223> OTHER INFORMATION: Synthetic Construct

<400> SEQUENCE: 319
ggatccatcg aaggtcgtca ctccgacgct gttttcaccg acaactacac gcgtctgcgt    60
aaacagatgg ctaaaaagaa atacctgaac tccatccgta accgtatcta atgagaattc   120

```
<210> SEQ ID NO 320
<211> LENGTH: 120
<212> TYPE: DNA
<213> ORGANISM: Artificial
<220> FEATURE:
<223> OTHER INFORMATION: Synthetic Construct

<400> SEQUENCE: 320
ggatccatcg aaggtcgtca ctccgacgct gttttcaccg acaactacac gcgtctgcgt      60
aaacagatgg ctcgcaagaa atacctgaac tccatccgta accgtatcta atgagaattc     120

<210> SEQ ID NO 321
<211> LENGTH: 120
<212> TYPE: DNA
<213> ORGANISM: Artificial
<220> FEATURE:
<223> OTHER INFORMATION: Synthetic Construct

<400> SEQUENCE: 321
ggatccatcg aaggtcgtca ctccgacgct gttttcaccg acaactacac gcgtctgcgt      60
aaacagatgg cttccaagaa atacctgaac tccatccgta accgtatcta atgagaattc     120

<210> SEQ ID NO 322
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 322

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Arg Ile
            20                  25                  30

<210> SEQ ID NO 323
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 323

His Ser Asp Ala Val Phe Thr Asp Asn Tyr Thr Arg Leu Arg Lys Gln
1               5                   10                  15

Met Ala Gly Lys Lys Tyr Leu Asn Ser Ile Lys Asn Arg Ile
            20                  25                  30

<210> SEQ ID NO 324
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 324
```

His Ser Asp Ala Val Phe Thr Asp Asn Tyr Thr Arg Leu Arg Lys Gln
1               5                   10                  15

Met Ala Lys Lys Lys Tyr Leu Asn Ser Ile Lys Asn Arg Ile
            20                  25                  30

<210> SEQ ID NO 325
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 325

His Ser Asp Ala Val Phe Thr Asp Asn Tyr Thr Arg Leu Arg Lys Gln
1               5                   10                  15

Met Ala Arg Lys Lys Tyr Leu Asn Ser Ile Lys Asn Arg Ile
            20                  25                  30

<210> SEQ ID NO 326
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 326

His Ser Asp Ala Val Phe Thr Asp Asn Tyr Thr Arg Leu Arg Lys Gln
1               5                   10                  15

Met Ser Lys Lys Lys Tyr Leu Asn Ser Ile Lys Asn Arg Ile
            20                  25                  30

<210> SEQ ID NO 327
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 327

His Ser Asp Ala Val Phe Thr Asp Asn Tyr Thr Arg Leu Arg Lys Gln
1               5                   10                  15

Met Ala Ala Lys Lys Tyr Leu Asn Ser Ile Pro Asn Arg Ile
            20                  25                  30

<210> SEQ ID NO 328
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 328

His Ser Asp Ala Val Phe Thr Asp Asn Tyr Thr Arg Leu Arg Lys Gln
1               5                   10                  15

Met Ala Gly Lys Lys Tyr Leu Asn Ser Ile Pro Asn Arg Ile
            20                  25                  30

<210> SEQ ID NO 329
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 329

His Ser Asp Ala Val Phe Thr Asp Asn Tyr Thr Arg Leu Arg Lys Gln
1               5                   10                  15

Met Ala Lys Lys Lys Tyr Leu Asn Ser Ile Pro Asn Arg Ile
            20                  25                  30

<210> SEQ ID NO 330
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 330

His Ser Asp Ala Val Phe Thr Asp Asn Tyr Thr Arg Leu Arg Lys Gln
1               5                   10                  15

Met Ala Arg Lys Lys Tyr Leu Asn Ser Ile Pro Asn Arg Ile
            20                  25                  30

<210> SEQ ID NO 331
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 331

His Ser Asp Ala Val Phe Thr Asp Asn Tyr Thr Arg Leu Arg Lys Gln
1               5                   10                  15

Met Ala Ser Lys Lys Tyr Leu Asn Ser Ile Pro Asn Arg Ile
            20                  25                  30

<210> SEQ ID NO 332
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 332

His Ser Asp Ala Val Phe Thr Asp Asn Tyr Thr Arg Leu Arg Lys Gln
1               5                   10                  15

Met Ala Ala Lys Lys Tyr Leu Asn Ser Ile Gln Asn Arg Ile
            20                  25                  30

<210> SEQ ID NO 333
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 333

His Ser Asp Ala Val Phe Thr Asp Asn Tyr Thr Arg Leu Arg Lys Gln
1               5                   10                  15
Met Ala Gly Lys Lys Tyr Leu Asn Ser Ile Gln Asn Arg Ile
            20                  25                  30

<210> SEQ ID NO 334
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 334

His Ser Asp Ala Val Phe Thr Asp Asn Tyr Thr Arg Leu Arg Lys Gln
1               5                   10                  15
Met Ala Lys Lys Lys Tyr Leu Asn Ser Ile Gln Asn Arg Ile
            20                  25                  30

<210> SEQ ID NO 335
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 335

His Ser Asp Ala Val Phe Thr Asp Asn Tyr Thr Arg Leu Arg Lys Gln
1               5                   10                  15
Met Ala Arg Lys Lys Tyr Leu Asn Ser Ile Gln Asn Arg Ile
            20                  25                  30

<210> SEQ ID NO 336
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 336

His Ser Asp Ala Val Phe Thr Asp Asn Tyr Thr Arg Leu Arg Lys Gln
1               5                   10                  15
Met Ala Ser Lys Lys Tyr Leu Asn Ser Ile Gln Asn Arg Ile
            20                  25                  30

<210> SEQ ID NO 337
<211> LENGTH: 30

```
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 337
```

His Ser Asp Ala Val Phe Thr Asp Asn Tyr Thr Arg Leu Arg Lys Gln
1               5                   10                  15

Met Ala Ala Lys Lys Tyr Leu Asn Ser Ile Arg Asn Arg Ile
            20                  25                  30

```
<210> SEQ ID NO 338
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 338
```

His Ser Asp Ala Val Phe Thr Asp Asn Tyr Thr Arg Leu Arg Lys Gln
1               5                   10                  15

Met Ala Gly Lys Lys Tyr Leu Asn Ser Ile Arg Asn Arg Ile
            20                  25                  30

```
<210> SEQ ID NO 339
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 339
```

His Ser Asp Ala Val Phe Thr Asp Asn Tyr Thr Arg Leu Arg Lys Gln
1               5                   10                  15

Met Ala Lys Lys Lys Tyr Leu Asn Ser Ile Arg Asn Arg Ile
            20                  25                  30

```
<210> SEQ ID NO 340
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(30)

<400> SEQUENCE: 340
```

His Ser Asp Ala Val Phe Thr Asp Asn Tyr Thr Arg Leu Arg Lys Gln
1               5                   10                  15

Met Ala Arg Lys Lys Tyr Leu Asn Ser Ile Arg Asn Arg Ile
            20                  25                  30

```
<210> SEQ ID NO 341
<211> LENGTH: 30
<212> TYPE: PRT
<213> ORGANISM: Artificial
<220> FEATURE:
```

```
<223> OTHER INFORMATION: Synthetic Construct
<220> FEATURE:
<221> NAME/KEY: PEPTIDE
<222> LOCATION: (1)..(30)

<400> SEQUENCE: 341

His Ser Asp Ala Val Phe Thr Asp Asn Tyr Thr Arg Leu Arg Lys Gln
1               5                   10                  15

Met Ala Ser Lys Lys Tyr Leu Asn Ser Ile Arg Asn Arg Ile
            20                  25                  30

<210> SEQ ID NO 342
<211> LENGTH: 19
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(19)

<400> SEQUENCE: 342

Cys Arg Lys Gln Val Ala Ala Lys Lys Tyr Leu Gln Ser Ile Lys Asn
1               5                   10                  15

Lys Arg Tyr

<210> SEQ ID NO 343
<211> LENGTH: 9
<212> TYPE: PRT
<213> ORGANISM: Artificial
<220> FEATURE:
<223> OTHER INFORMATION: Synthetic Construct
<220> FEATURE:
<221> NAME/KEY: PEPTIDE
<222> LOCATION: (1)..(9)

<400> SEQUENCE: 343

Ser Trp Cys Glu Pro Gly Trp Cys Arg
1               5
```

PITUITARY ADENYLATE CYCLASE ACTIVATING PEPTIDE (PACAP)RECEPTOR 3 (R3) AGONISTS AND THEIR PHARMACOLOGICAL METHODS OF USE

This application claims benefit of U.S. Provisional Applications Nos. 60/327,556, filed Jun. 15, 2000 and 60/240,954, filed Sep. 28, 1999.

FIELD OF THE INVENTION

This invention relates to newly identified polypeptides and the use of such polypeptides for therapeutic purposes. More particularly, the polypeptides of the present invention are useful in stimulating the release of insulin from pancreatic beta cells in a glucose-dependent manner, thereby providing a treatment option for those individuals afflicted with a metabolic disorder such as diabetes or impaired glucose tolerance, a prediabetic state.

BACKGROUND OF THE RELATED ART

Diabetes is characterized by impaired glucose metabolism manifesting itself among other things by an elevated blood glucose level in the diabetic patient. Underlying defects lead to a classification of diabetes into two major groups: type I diabetes, or insulin dependent diabetes mellitus (IDDM), which arises when patients lack beta-cells producing insulin in their pancreatic glands, and type 2 diabetes, or non-insulin dependent diabetes mellitus (NIDDM), which occurs in patients with an impaired beta-cell function and alterations in insulin action.

Type I diabetic patients are currently treated with insulin, while the majority of type 2 diabetic patients are treated with agents that stimulate beta-cell function or with agents that enhance the tissue sensitivity of the patients towards insulin. Over time almost one-half of type 2 diabetic subjects lose their response to these agents and then must be placed on insulin therapy. The drugs presently used to treat type 2 Diabetes include:

Alpha-glucosidase inhibitors (PRECOSE®, VOGLIBOSE™, and MIGLITOL®). Alpha-glucosidase inhibitors reduce the excursion of postprandial glucose by delaying the absorption of glucose from the gut. These drugs are safe and provide treatment for mild to moderately affected diabetic subjects. However, gastrointestinal side effects have been reported in the literature.

Insulin sensitizers. Insulin sensitizers are drugs that enhance the body's response to insulin. Thiozolidinediones such as REZULIN™ (troglitazone) activate the PPAR gamma receptor and modulate the activity of a set of genes that have not been well described. Although effective, these drugs have been associated with liver toxicity. Because of hepatotoxicity, REZULIN has been withdrawn from the market.

Insulin secretagogues (sulfonylureas and other agents that act by the ATP-dependent K+ channel). SFUs are standard therapy for type 2 diabetics that have mild to moderate fasting glycemia. The SFUs have limitations that include a potential for inducing hypoglycemia, weight gain, and high primary and secondary failure rates. 10 to 20% of initially treated patients fail to show a significant treatment effect (primary failure). Secondary failure is demonstrated by an additional 20–30% loss of treatment effect after six months on an SFU. Insulin treatment is required in 50% of the SFU responders after 5–7 years of therapy (Scheen, A. J., et al., *Diabetes Res. Clin. Pract.* 6:533–543 (1989)).

GLUCOPHAGE™ (metformin HCl) is a biguanide that lowers blood glucose by decreasing hepatic glucose output and increasing peripheral glucose uptake and utilization. The drug is effective at lowering blood glucose in mildly and moderately affected subjects and does not have the side effects of weight gain or the potential to induce hypoglycemia. However, GLUCOPHAGE has a number of side effects including gastrointestinal disturbances and lactic acidosis. GLUCOPHAGE is contraindicated in diabetics over the age of 70 and in subjects with impairment in renal or liver function. Finally, GLUCOPHAGE has the same primary and secondary failure rates as the SFUs.

Insulin treatment is instituted after diet, exercise, and oral medications have failed to adequately control blood glucose. This treatment has the drawbacks that it is an injectable, that it can produce hypoglycemia, and that it causes weight gain.

Because of the problems with current treatments, new therapies to treat type 2 diabetes are needed. In particular, new treatments to retain normal (glucose-dependent) insulin secretion are needed. Such new drugs should have the following characteristics: dependent on glucose for promoting insulin secretion, i.e. produce insulin secretion only in the presence of elevated blood glucose; low primary and secondary failure rates; and preserve islet cell function. The strategy to develop the new therapy disclosed herein is based on the cyclic adenosine monophosphate (cAMP) signaling mechanism and its effects on insulin secretion.

Cyclic AMP is a major regulator of the insulin secretion process. Elevation of this signaling molecule promotes the closure of the K+ channels following the activation of protein kinase A pathway. Closure of the K+ channels causes cell depolarization and subsequent opening of Ca++ channels, which in turn leads to exocytosis of insulin granules. Little if any effects on insulin secretion occurs in the absence of low glucose concentrations (Weinhaus, A., et al., *Diabetes* 47: 1426–1435 (1998)). Secretagogues like pituitary adenylate cyclase activating peptide ("PACAP") and GLP-1 use the cAMP system to regulate insulin secretion in a glucose-dependent fashion (Komatsu, M., et al., *Diabetes* 46: 1928–1938, (1997)). Insulin secretagogues working through the elevation of cAMP such as GLP-1 and PACAP is also able to enhance insulin synthesis in addition to insulin release (Skoglund, G. et al., Diabetes 49: 1156–1164, (2000). Borboni, P. et al., Endocrinology 140: 5530–5537, (1999)).

PACAP is a potent stimulator of glucose-dependent insulin secretion from pancreatic beta-cells. Three different PACAP receptor types (R1, R2, and R3) have been described (Harmar, A. et al., *Pharmacol. Reviews* 50: 265–270 (1998)). PACAP displays no receptor selectivities, having comparable activities and potencies at all three receptors. R1 is located predominately in the CNS, whereas R2 and R3 are more widely distributed. R2 is located in the CNS as well as in liver, lungs and intestine. R3 is located in the CNS, pancreas, skeletal muscle, heart, kidney, adipose tissue, testis and stomach. Recent work argues that R3 is responsible for the insulin secretion from beta cells (Inagaki, N. et al., *PNAS* 91: 2679–2683, (1994)). This insulinotropic action of PACAP is mediated by the GTP binding protein Gs. Accumulation of intracellular cAMP in turn activates the nonselective cation channels in beta cells increasing [Ca++], and promotes exocytosis of insulin-containing secretory granules.

PACAP is the newest member of the superfamily of metabolic, neuroendocrine and neurotransmitter peptide hormones that exert their action through the cAMP-mediated signal transduction pathway (Arimura, *Regul. Peptides* 37:287–303 (1992)). The biologically active peptides are released from the biosynthetic precursor in two molecular forms, either as a 38-amino acid peptide (PACAP-38) and/or as a 27-amino acid peptide (PACAP-27) with an amidated carboxyl termini (Arimura, supra).

The highest concentrations of the two forms of the peptide are found in the brain and testis (reviewed in Arimura, supra). The shorter form of the peptide, PACAP-27, shows 68% structural homology to vasoactive intestinal polypeptide (VIP). However, the distribution of PACAP and VIP in the central nervous system suggests that these structurally related peptides have distinct neurotransmitter functions (Koves et al., *Neuroendocrinology* 54:159–169, (1991)).

Recent studies have demonstrated diverse biological effects of PACAP-38, from a role in reproduction (McArdle, *Endocrinology* 135:815–817 (1994)) to ability to stimulate insulin secretion (Yada et al., *J. Biol. Chem.* 269:1290–1293 (1994)).

Vasoactive intestinal peptide (VIP) is a 28 amino acid peptide that was first isolated from hog upper small intestine (Said and Mutt, *Science* 169: 1217–1218, 1970; U.S. Pat. No. 3,879,371). This peptide belongs to a family of structurally-related, small polypeptides that includes helodermin, secretin, the somatostatins, and glucagon. The biological effects of VIP are mediated by the activation of membrane-bound receptor proteins that are coupled to the intracellular cAMP signaling system. These receptors were originally known as VIP-R1 and VIP-R2, however, they were later found to be the same receptors as PACAP-R2 and PACAP-R3. VIP displays comparable activities and potencies at PACAP-R2 and PACAP-R3.

To improve the stability of VIP in human lung fluid, Bolin et al (*Biopolymers* 37: 57–66, (1995)) made a series of VIP variants designed to enhance the helical propensity of this peptide and reduce proteolytic degradation. Substitutions were focused on positions 8, 12, 17, and 25–28, which were implicated to be unimportant for receptor binding. Moreover, the "GGT" sequence was tagged onto the C-terminus of VIP muteins with the hope of more effectively capping the helix. Finally, to further stabilize the helix, several cyclic variants were synthesized (U.S. Pat. No. 5,677,419). Although these efforts were not directed toward receptor selectivity, they yielded two analogs (designated herein as R3P0 and R3P4) that have greater than 100-fold PACAP-R3 selectivity (Gouriet et al., *Peptides* 18: 403–408, (1997); Xia et al., *J. Pharmacol. Exp. Ther.*, 281: 629–633, (1997)).

GLP-1 is released from the intestinal L-cell after a meal and functions as an incretin hormone (i.e. it potentiates glucose-induced insulin release from the pancreatic beta-cell). It is a 37-amino acid peptide that is differentially expressed by the Glucagon gene, depending upon tissue type. The clinical data that support the beneficial effect of raising cAMP levels in β-cells have been collected with GLP-1. Infusions of GLP-1 in poorly controlled type 2 diabetics normalized their fasting blood glucose levels (Gutniak, M., et al., *New Eng. J. Med.* 326:1316–1322, (1992)) and with longer infusions improved the beta cell function to those of normal subjects (Rachman, J. et al., *Diabetes* 45: 1524–1530, (1996)). A recent report has shown that GLP-1 improves the β-cells' ability to respond to glucose in subjects with impaired glucose tolerance (Byrne M., et al., *Diabetes* 47: 1259–1265 (1998)). All of these effects, however, are short-lived because of the short half-life of the peptide. Recently Novo Nordisk has discontinued clinical trials with GLP-1. This failure reportedly was due to a very short plasma half-life of the peptide of a few minutes.

EXENDIN 4™. Amylin Pharmaceuticals is conducting Phase I trials with EXENDIN 4 (AC2993), a 39 amino acid peptide originally identified in Gila Monster. Phase II trials have recently begun. Amylin claims preclinical results showing a 4 hour duration of efficacy and efficacy in animal models when AC2993 is administered subcutaneously, orally, and nasally. However, at doses of 0.2 and 0.3 ug/kg, the incidence of headaches, postural hypotension, nausea and vomiting was significant.

There exists a need for an improved peptide that has the glucose-dependent insulin secretagogue activity of PACAP, GLP-1, or EXENDIN 4, and yet has fewer side-effects.

SUMMARY OF THE INVENTION

This invention provides novel polypeptides that function in vivo as agonists of the PACAP R3 receptor (hereafter, R3) and are effective in the treatment of diseases and conditions that can be ameliorated by agents having R3 agonist activity. Preferably, the polypeptides of this invention are selective R3 agonists, having greater potency at R3 than at R2 and R1. For example, but not by way of limitation, these polypeptides stimulate insulin synthesis and release from pancreatic beta cells in a glucose-dependent fashion and subsequent plasma glucose reduction. These insulin secretagogue polypeptides are shown to stimulate insulin release in rat and human islet cells in vitro and in vivo. Unlike PACAP-27, these secretagogue polypeptides also lower blood glucose in vivo more than vehicle control upon glucose challenge.

The polypeptides of the present invention provide a new therapy for patients with, for example, metabolic disorders such as those resulting from decreased endogenous insulin secretion, in particular type 2 diabetics, or for patients with impaired glucose tolerance, a prediabetic state that has a mild alteration in insulin secretion.

In particular, one aspect of the invention is a polypeptide selected from the group consisting of SEQ ID NOs: 11 through 14, SEQ ID NO: 18, SEQ ID NOs: 21 through 26, SEQ ID NOs: 32 through 36, SEQ ID NOs: 40 through 53, SEQ ID NOs: 57 through 61, SEQ ID NOs: 63 through 99, SEQ ID NOs: 102 through 119, SEQ ID NOs: 121 through 137, SEQ ID NOs: 139 through 177, SEQ ID NOs: 179, 180, SEQ ID NOs: 183 through 202, 322 through 341, and fragments, derivatives and variants thereof that demonstrate at least one biological function that is substantially the same as the polypeptides of the listed SEQ ID NOs. (collectively, "polypeptides of this invention"), including functional equivalents thereof. A preferred embodiment of this invention is a polypeptide selected from the group consisting of SEQ ID NOs. 12, 18, 21–26, 32–35, 41, 43–53, 63, 66, 70–92, 94–99, 102–104, 107, 109, 112–119, 121–137, 139, 140, 142–153, 156–174, 187, 322 through 341, and fragments, derivatives, and variants thereof that demonstrate at least one biological function that is substantially the same as the polypeptides of the listed SEQ ID NOs. A more preferred embodiment of this invention is a polypeptide selected from the group consisting of SEQ ID NOs 18, 24, 25, 32, 33, 43–50, 52, 53, 70–87, 92, 98, 99, 104, 107, 112–114, 129–131, 137, 140, 144, 147–151, 156–159, and 161–173, 323, 324, 326, 327, 335, 338, 341, and fragments, derivatives and variants thereof that demonstrate at least one biological function that is substantially the same as the polypeptides of the listed SEQ ID NOs. A most preferred embodiment of this invention is a polypeptide selected from the group consisting of SEQ ID NOs 18, 32, 43, 45, 47, 50, 52, 71, 72, 83, 86, and 87, and fragments, derivatives and variants thereof that demonstrate at least one biological function that is substantially the same as the polypeptides of the listed SEQ ID NOs.

Another embodiment of the invention is a polynucleotide that encodes for the polypeptides of this invention, and the attendant vectors and host cells necessary to recombinantly express the polypeptides of this invention. These polynucleotide sequences include those identified as SEQ ID NOs: 204, 207–211, 214–230, and 232–321. Preferred polynucleotides include those identified as SEQ. ID. NOs 204, 207–209, 215, 217–230, 232–234, 237, 239, 242–268, 270–281, and 284–321. More preferred polynucleotides include those identified as SEQ ID NOs 207, 218–224, 226–230, 234, 237, 242–244, 258–260, 266, 268, 272, 275–279, 284–287, 289–301, and 303, 304, 306, 307, 318, and 321. Most preferred polynucleotides include those identified as SEQ ID NO 217, 221, and 226.

Antibodies and antibody fragments that selectively bind the polypeptides of this invention are also provided. Such antibodies are useful in detecting the polypeptides of this invention, and can be identified and made by procedures well known in the art, including those analogous to that described in Example 17 below, The invention is also directed to a method of treating diabetes and/or other diseases or conditions affected by the polypeptides of this invention, preferably effected by the R3 agonist function of the polypeptides of this invention, in a mammal, comprising administering a therapeutically effective amount of any of the polypeptides of the present invention or any polypeptide active at R3 such as SEQ ID NO 5 and 9 to said mammal.

Also disclosed are methods of making the polypeptides of this invention, both recombinant and synthetic.

BRIEF DESCRIPTION OF THE DRAWING

FIG. 1 depicts amino acid sequences of polypeptides of SEQ ID NO: 11 through 14, SEQ ID NO: 18, SEQ ID NOs: 21 through 26, SEQ ID NOs: 32 through 36, SEQ ID NOs: 40 through 53, SEQ ID NOs: 57 through 61, SEQ ID NOs: 63 through 99, SEQ ID NOs: 102 through 119, SEQ ID NOs: 121 through 137, SEQ ID NOs: 139 through 177, SEQ ID NOs: 179, 180, SEQ ID NOs: 183 through 202, and SEQ ID NOs: 322 through 341 which are claimed polypeptides.

FIG. 2 is a sequence alignment of VIP mutants and native polypeptides VIP, PACAP38, GLP-1, EXENDIN-4 and examples of R3 selective polypeptides. Conserved residues are bolded and shaded in dark gray while conservative changes are shaded in light gray.

FIG. 8 depicts polynucleotide sequences SEQ ID NOs 54 through 56 and 203 through 301 that encode for the polypeptides of this invention.

The first 6 nucleotides represent the Bam HI restriction enzyme recognition site followed by the next 12 nucleotides which encode the "IEGR" Factor Xa recognition site. The last 6 nucleotides represent the Xho I or Eco RI restriction enzyme recognition site preceded by the 6 nucleotides that encode the two stop codons. The nucleotides between the Factor Xa site and stop codons encode the amino acid sequence of the corresponding polypeptide. The nucleotides between the two restriction sites are cloned into the corresponding restriction sites on the pGEX-6P-1 vector (Amershm Pharmacia Biotech). The SEQ ID NOs are denoted in parenthesis.

Figure 9:
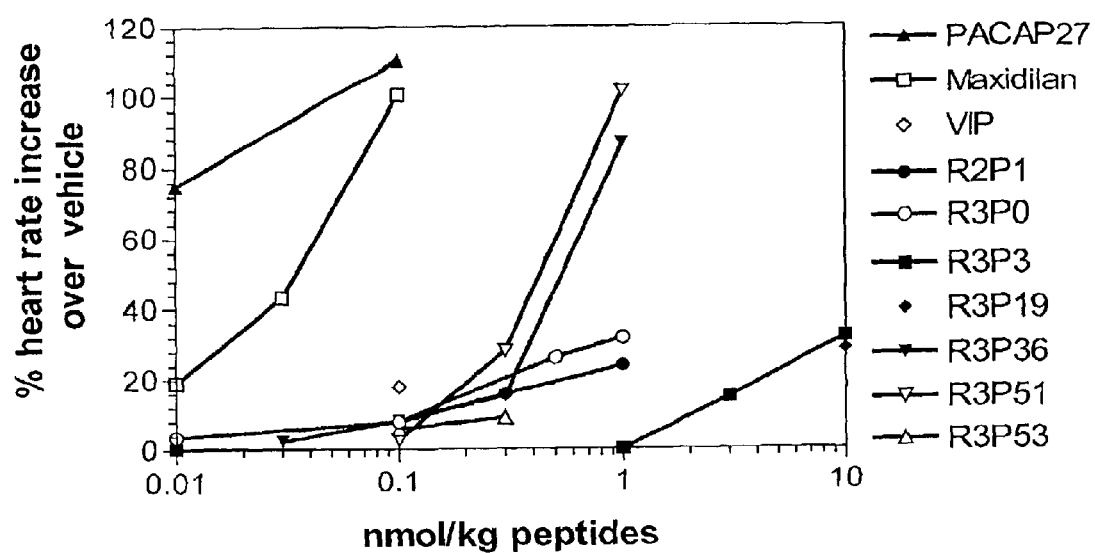

FIG. 9 shows the effect of PACAP-27, VIP and receptor selective agonists on the heart rate in conscious dogs (see example 15).

Figure 10:
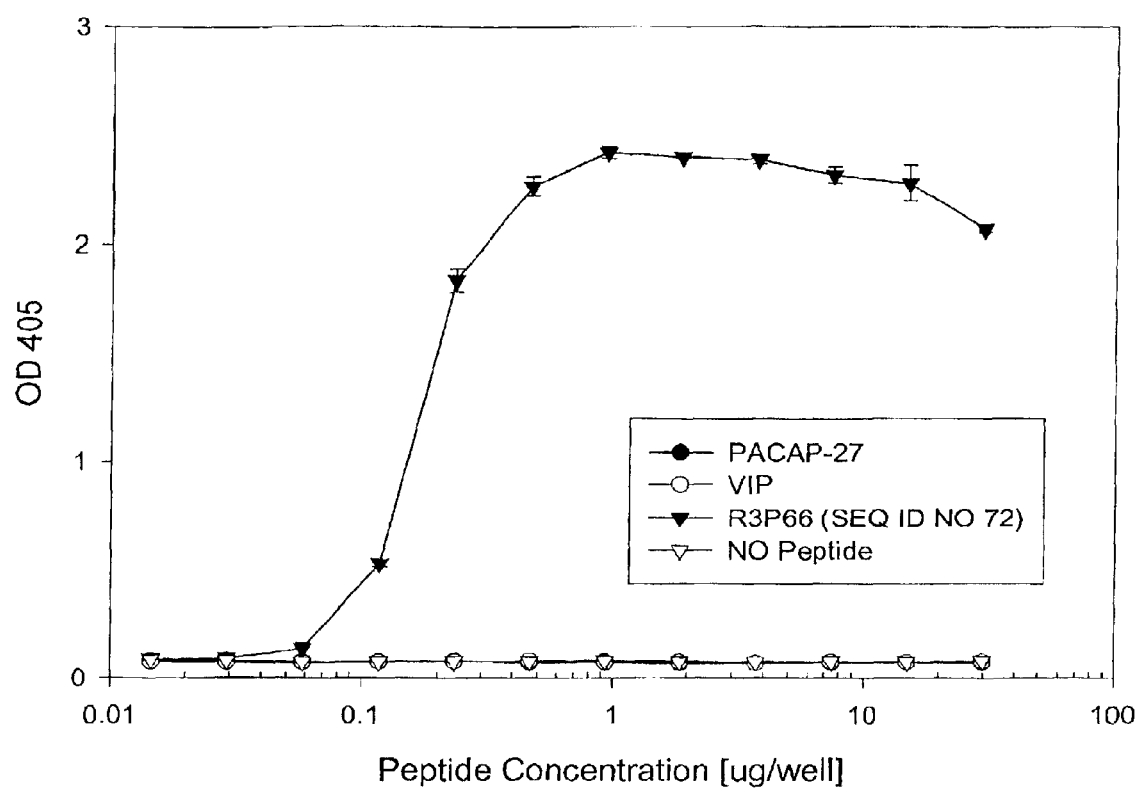

FIG. 10 shows detection of R3P66 by polyclonal antibodies produced in rabbits immunized with R3P66 C-terminus sequence (Ac-CRKQVAAKKYLQSIKNKRY-COOH) (SEQ ID NO: 342), using ELISA.

DETAILED DESCRIPTION OF THE PREFERRED EMBODIMENTS

This invention provides novel polypeptides, and fragments, derivatives and variants thereof that demonstrate at least one biological function that is substantially the same as the polypeptides of FIG. 1 (collectively, polypeptides of this invention). The polypeptides of this invention function in vivo as R3 agonists or otherwise in the prevention and/or treatment of such diseases or conditions as diabetes, asthma, hypertension, male reproduction problems including human sperm motility, cardiovascular diseases, ulcers, and other conditions identified herein, or function otherwise as described later herein. Preferably, the polypeptides of this invention will stimulate insulin release from pancreatic beta cells in a glucose-dependent fashion.

The polypeptides of this invention are R3 agonists. Preferably, they are selective R3 agonists with at least 10-fold selectivity for R3 over R2 and/or R1. More preferably, they are selective R3 agonists with at least 100-fold selectivity for R3 over R2 and/or R1. Most preferably, they stimulate insulin release into plasma in a glucose-dependent fashion without inducing a stasis or increase in the level of plasma glucose that is counterproductive to the treatment of, for example, type 2 diabetes. Additionally, it is preferable for the polypeptides of this invention to be selective agonists of the R3 receptor, thereby causing, for example, an increase in insulin release into plasma, while being selective against other receptors that are responsible for such disagreeable or dangerous side effects as gastrointestinal water retention, and/or unwanted cardiovascular effects such as increased heart rate. It has now been discovered that R3-mediated insulin secretion does not cause hypoglycemia, R2 activation leads to glucose release into plasma which is counterproductive to the treatment of type 2 diabetes and gastrointestinal water retention, and R1 activation leads to cardiovascular effects such as increased heart rate.

The polypeptides of this invention provide a new therapy for patients with decreased endogenous insulin secretion or impaired glucose tolerance in particular type 2 diabetes.

A. Discussion

PACAP, VIP, GLP-1 and Exendin-4 are polypeptides capable of stimulating insulin release in a glucose-dependent fashion. However, this fact alone does not guarantee glucose reduction in vivo. Since PACAP is known to bind to PACAP-R1, -R2 and -R3 receptors, and VIP is known to bind to PACAP-R2 and -R3 receptors, it was thought that they may have similar conserved structural features. The stacking alignment below shows the primary structural relationships:

|  |  |  | SEQ ID NO. |
|---|---|---|---|
| VIP | 1 HSDAVFTDNY TRLRKQMAVK KYLNSILN-NH$_2$ | 28 | 1 |
| PACAP38 | 1 HSDGIFTDSY SRYRKQMAVK KYLAAVLGKR YKQRVKNK-NH$_2$ | 38 | 2 |
| GLP-1 | 1 HAEGTFTSDV SSYLEGQAAK EFIAWLVKGR-NH$_2$ | 30 | 3 |
| Exendin 4 | 1 HGEGTFTSDL SKQMEEEAVR LFIEWLKNGG PSSGAPPPS-NH$_2$ | 39 | 4 |

(where single-letter abbreviations for amino acids can be found in Zubay, *Biochemistry* 2d ed., 1988, MacMillan Publishing, New York, p. 33), and are defined below. The polypeptides of the present invention (FIG. 1) are most closely related to VIP in terms of their primary structure with the exception of SEQ ID NO: 57–61, 66–69, and 176, 177, 179, 180, 183–202 which are more closely related to PACAP.

The inventors herein have created a new polypeptide that is an R3 agonist, preferably a selective R3 agonist, and/or that exhibits a selective glucose-dependent insulin secretagogue effect wherein selective activation of the PACAP R3 receptor indeed leads to a glucose dependent pathway to insulin secretion by pancreatic beta cells, with concomitant glucose reduction in vivo. In that light, they first studied the structures of PACAP-27 and VIP in an effort to determine the residues most likely responsible for receptor selectivity. It is known that PACAP and VIP do not reduce glucose in vivo, but, rather, they stimulate glucose release from the liver. It has been shown that activation of R2 increases plasma glucose levels in vivo. Previously, both PACAP and VIP have been mutagenized extensively for various reasons. For instance, serial deletions of PACAP27 and PACAP38 from both ends confirmed the importance of both termini for receptor binding (Gourlet et al., *Eur. J. Pharm.* 287: 7–11, (1995); Gouriet et al., *Regul. Peptides* 62: 125–130, (1996)). Rat brain membrane binding and adenylate cyclase activities of PACAP27/VIP hybrid muteins implicated the importance of the N-terminal residues of PACAP for PACAP-R1 recognition (Ando et al., *Blomed. Pept. Proteins Nucleic Acids* 2:41–46, (1996)). Increasing the basicity of Leu[17]-PACAP27 and Leu[17]-VIP by making K15R, K20R, and K21R mutations and extension of the C-terminus with "GKR" sequence led to an increase in duration of guinea pig tracheal relaxant activity proposed to be due to protection from heparin binding (Kashimoto et al., *Ann. NY Acad. Sci.* 805: 505–510, (1996)). Gourlet et al. (*Biochim. BioDhys, Acta* 1314: 267–273, (1996)) demonstrated that the Q16R mutein of VIP and PACAP possessed greater affinities than their respective native polypeptides for PACAP-R2 and R1, respectively. Gourlet et al. (*Peptides* 18: 1539–1545, (1997)) developed a high affinity R2-selective agonist by making the chimeric substituted peptide [K15, R16, L27] VIP(1–7)/GRF(8–27). N-terminal acylation and D-Phe2 substitution of this selective agonist led to a potent R2 selective antagonist (Gourlet et al., *Peptides* 18 1555–1560, (1997)). VIP muteins Y22L and Y22A, but not Y22F, display lower affinity for PACAP-R3, suggesting the importance of an aromatic group at position 22 for receptor R3 binding but not for receptor R2 binding (Gourlet, *Eur. J. Biochem.* 348: 95–99, (1998)). Helodermin and helospectin, VIP-like peptides isolated from the salivary gland venom of lizards exhibit ~100-fold PACAP-R3 selectivity (Gourlet, *Ann. NY Acad. Sci.* 865: 247–252, (1998)). Photoaffinity labeling of PACAP27 by replacing F6 and Y22 with p-benzoyl-L-phenylalanine (pBz) or K15, K20, and K21 with pBz$_2$ suggested that K15 and F22 are closer to PACAP-R1 than F6, K20, and K21 (Cao et al., *Eur. J. Biochem.* 244: 400–406, (1997); Cao et al., *Ann. NY Acad. Sci.*, 865 82–91, (1998)).

The inventors herein have found several polypeptides that cause the stimulation of release of insulin in a glucose-dependent manner and cause glucose reduction in vivo. Those polypeptides bear some similarity to VIP and PACAP. In particular, a stacked alignment shows the following:

|  |  |  | SEQ. ID NO. |
|---|---|---|---|
| VIP | 1 HSDAVFTDNY TRLRKQMAVK KYLNSILN-NH$_2$ | 28 | 1 |
| PACAP38 | 1 HSDGIFTDSY SRYRKQMAVK KYLAAVLGKR YKQRVKNK-NH$_2$ | 38 | 2 |
| R3P1 | Ac-HSDAVFTENY TKLRKQLAAK KYLNDLKKGG T-NH$_2$ | 31 | 6 |
| R3P3 | 1 HSDAVFTENY TKLRKQLAAK KYLNDLKKGG T | 31 | 8 |
| R3P12 | 1 HSDAVFTDNY TRLRKQLAAK KYLNDIKKGG T | 31 | 15 |
| R3P13 | 1 HSDAVFTDNY TRLRKQLAAK KYLNDIKK-NH$_2$ | 28 | 16 |
| R3P36 | 1 HSDAVFTDNY TRLRKQLAAK KYLNDIKKKR Y | 31 | 32 |
| R3P66 | 1 HSDAVFTDNY TRLRKQLAAK KYLQSIKNKR Y | 31 | 72 |

However, there is no teaching in the scientific or patent literature that suggests that select modifications to the VIP and PACAP sequences lead to a polypeptide with the ability to stimulate insulin secretion in a glucose-dependent fashion, and reduce plasma glucose concentration.

Certain terms used throughout this specification will now be defined, and others will be defined as introduced. The single letter abbreviation for a particular amino acid, its corresponding amino acid, and three letter abbreviation are as follows: A, alanine (ala); C, cysteine (cys); D, aspartic acid (asp); E, glutamic acid (glu); F, phenylalanine (phe); G, glycine (gly); H, histidine (his); I, isoleucine (ile); K, lycine (lys); L, leucine (leu); M, methionine (met); N, asparagine (asn); P, proline (pro); Q, glutamine (gin); R, arginine (arg); S, serine (ser); T, threonine (thr); V, valine (val); W, tryptophan (trp); Y, tyrosine (tyr).

The term "polynucleotide encoding a polypeptide" encompasses a polynucleotide which includes only coding sequence for the polypeptide as well as a polynucleotide which includes additional coding and/or non-coding sequence. The present invention further relates to polynucleotides which hybridize to the hereinabove-described sequences if there is at least about 70%, preferably at least about 90%, and more preferably at least about 95% identity between the sequences. The present invention particularly relates to polynucleotides encoding polypeptides which hybridize under stringent conditions to the hereinabove-described polynucleotides. As herein used, the term "stringent conditions" means "stringent hybridization conditions" Preferably, hybridization will occur only if there is at least about 90% and preferably about 95% through 97% identity between the sequences. The polynucleotides which hybridize to the hereinabove described polynucleotides in a preferred embodiment encode polypeptides which retain substantially the same biological function or activity as the mature polypeptide encoded by the cDNAs.

"Functional equivalent" and "substantially the same biological function or activity" each means that degree of biological activity that is within about 30% to 100% or more of that biological activity demonstrated by the polypeptide to which it is being compared when the biological activity of each polypeptide is determined by the same procedure. For example, a polypeptide that is functionally equivalent to a polypeptide of FIG. 1 is one that, when tested in the Cyclic AMP scintillation proximity assay of Specific Example 16, demonstrates accumulation of cAMP in CHO cell line expressing the human PACAP/VIP R2 (PACAP R3) receptor.

A polypeptide of this invention that is an R3 agonist is one that demonstrates about 30%–100% or more of maximal PACAP-27 R3 agonist activity when tested in the protocol of Example 16. The preferred polypeptides of this invention that are selective agonists for R3 over PACAP R2 and R1 receptors are those polypeptides that demonstrate the ratio of R3 agonist activity to R2 activity of about 10:1 or greater, and more preferably, about 100:1 or greater, and/or demonstrate the ratio of R3 agonist activity to R1 receptor activity of about 10:1 or greater, and more preferably, about 100:1 or greater when the polypeptide is tested in the protocol of Example 16, using cells that express the appropriate receptors.

"Stringent hybridization conditions" refers to an overnight incubation of the two pieces of polynucleotides to be hybridized at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

The terms "fragment," "derivative", and "variant", when referring to the polypeptides of FIG. 1, means fragments, derivatives, and variants of the polypeptides which retain substantially the same biological function or activity as such polypeptides, as described further below.

An analog includes a propolypeptide which includes within it, the amino acid sequence of the polypeptide of this invention. The active polypeptide of this invention can be cleaved from the additional amino acids that complete the propolypeptide molecule by natural, in vivo processes or by procedures well known in the art such as by enzymatic or chemical cleavage. For example, the 28-amino acid native peptide VIP is naturally expressed as a much larger polypeptide which is then processed in vivo to release the 28-amino acid active mature peptide.

A fragment is a portion of the polypeptide which retains substantially similar functional activity, as shown in the in vivo models disclosed herein as described further below.

A derivative includes all modifications to the polypeptide which substantially preserve the functions disclosed herein and include additional structure and attendant function, e.g., PEGylated polypeptides which have greater half-life, fusion polypeptides which confer targeting specificity or an additional activity such as toxicity to an intended target, as described further below.

The polypeptides of the present invention may be recombinant polypeptides, natural purified polypeptides or synthetic polypeptides.

The fragment, derivative, or variant of the polypeptides of the present invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethyleneglycol), or (iv) one in which the additional amino acids are fused to the mature polypeptide, such as a leader or secretory sequence or a sequence which is employed for purification of the mature polypeptide or a propolypeptide sequence, or v) one in which the polypeptide sequence is fused with a larger polypeptide, i.e. human albumin, a antibody or Fc, for increased duration of effect. Such fragments, derivatives, and variants and analogs are deemed to be within the scope of those skilled in the art from the teachings herein.

Preferably, the derivatives of the present invention will contain conservative amino acid substitutions (defined further below) made at one or more predicted, preferably nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystelne), nonpolar side chains (e.g., alanine, vailne, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non conservative substitutions would not be made for conserved amino acid residues or for amino acid residues residing within a conserved protein domain, such as residues 19 and 27 where such residues are essential for protein activity such as R3 activity and/or R3 selectivity. Fragments, or biologically active portions include polypeptide fragments suitable for use as a medicament, to generate antibodies, as a research reagent, and the like. Fragments include peptides comprising amino acid sequences sufficiently similar to or derived from the amino acid sequences of a polypeptide of this invention and exhibiting at least one activity of that polypeptide, but which include fewer amino acids than the full-length polypeptides disclosed herein.

Typically, biologically active portions comprise a domain or motif with at least one activity of the polypeptide. A biologically active portion of a polypeptide can be a peptide which is, for example, 5 or more amino acids in length. Such biologically active portions can be prepared synthetically or by recombinant techniques and can be evaluated for one or more of the functional activities of a polypeptide of this invention by means disclosed herein and/or well known in the art.

Moreover, preferred derivatives of the present invention include mature polypeptides that have been fused with another compound, such as a compound to increase the half-life of the polypeptide and/or to reduce potential immunogenicity of the polypeptide (for example, polyethyleneglycol "PEG"). In the case of PEGylation, the fusion of the polypeptide to PEG can be accomplished by any means known to one skilled in the art. For example, PEGylation can be accomplished by first introducing a cysteine mutation into the polypeptide, followed by site-specific derivatization with PEG-maleimide. The cysteine can be added to the C-terminus of the peptides. (See, for instance, Tsutsumi et al., *Proc Natl Acad Sci U S A* 2000 Jul. 18;97(15):8548–53).

Variants of the polypeptides of this invention include polypeptides having an amino acid sequence sufficiently similar to the amino acid sequence of the SEQ ID NOs of FIG. 1 or a domain thereof. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Preferably, variants will be sufficiently similar to the amino acid sequence of the preferred polypeptides of this invention. Variants include variants of polypeptides encoded by a polynucleotide that hybridizes to a polynucleotide of this invention or a complement thereof under stringent conditions. Such variants generally retain the functional activity of the polypeptides of this invention. Libraries of fragments of the polynucleotides can be used to generate a variegated population of fragments for screening and subsequent selection. For example, a library of fragments can be generated by treating a double-stranded PCR fragment of a polynucleotide with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the polypeptide of this invention.

Variants include polypeptides that differ in amino acid sequence due to mutagenesis. Variants that function as R3 agonists can be identified by screening combinatorial libraries of mutants, for example truncation mutants, of the polypeptides of this invention for R3 agonist activity.

In one embodiment, a variegated library of analogs is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential variant amino acid sequences is expressible as individual polypeptides, or, alternatively, as a set of larger fusion proteins (for example, for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential variant sequences. Methods for synthesizing degenerate oligonucleotides are known in the art (see, e.g., Narang (1983)*Tetrahedron* 39:3; Itakura et al (1984) *Annu. Rev. Biochem.* 53:323; Itakura et al (1984) *Science* 198:1056; Ike et al (1983)*Nucleic Acid Res.* 11:477).

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of R-agonist polypeptides. The most widely used techniques, which are amenable to high through-put analysis for screening large gene libraries typically include cloning the gene library into replicable expression vectors, transforming appropriate cells with the resulting library of vectors and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify the desired variants.

The invention also provides chimeric or fusion polypeptides. Examples include those polypeptides of this invention described in SEQ ID NOs 18 and 172 which are fusions of the pancreatic targeting sequence "SWCEPGWCR" (SEQ ID NO: 343) (Rajotte D., et al (1998) *J Clin Invest* 102:430437) with SEQ ID NOs 8 and 32, respectively. The targeting sequence is designed to localize the delivery of the polypeptide to the pancreas to minimize potential side effects. The polypeptides of this invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formulation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins, Structure and Molecular Properties*, 2nd ed., T. E. Creighton, W.H. Freeman and Company, New York (1993); *Posttranslational Covalent Modification of Proteins*, B. C. Johnson, ed., Academic Press, New York, pgs. 1–12 (1983); Seifter et al., *Meth. Enzymol* 182:626–646 (1990); Rattan et al., *Ann. N.Y. Acad. Sci.* 663:48–62 (1992)).

The polypeptides of the present invention include the polypeptides of FIG. 1, that are SEQ ID NOs: 11 through 14, SEQ ID NO: 18, SEQ ID NOs: 21 through 26, SEQ ID NOs: 32 through 36, SEQ ID NOs: 40 through 53, SEQ ID NOs: 57 through 61, SEQ ID NOs: 63 through 99, SEQ ID NOs: 102 through 119, SEQ ID NOs: 121 through 137, SEQ ID NOs: 139 through 177, SEQ ID NOs: 179, 180, SEQ ID NOs: 183 through 202, SEQ ID NOs: 322 through 341, as well as those sequences having insubstantial variations in sequence from them. An "insubstantial variation" would include any sequence, substitution, or deletion variant that maintains substantially at least one biological function of the polypeptides of this invention, preferably R3 agonist activity, and more preferably selective R3 agonist activity, and most preferably, the insulin secreting activity demonstrated herein. These functional equivalents may preferably include polypeptides which have at least about a 90% identity to the polypeptides of FIG. 1, and more preferably at least a 95% identity to the polypeptides of FIG. 1, and still more preferably at least a 97% identity to the polypeptides of FIG. 1, and also include portions of such polypeptides having substantially the same biological activity. However, any polypeptide having insubstantial variation in amino acid sequence from the polypeptides of FIG. 1 that demonstrates functional equivalency as described further herein is included in the description of the present invention.

As known in the art "similarity" between two polypeptides is determined by comparing the amino acid sequence and its conserved amino acid substitutes of one polypeptide to the sequence of a second polypeptide. Such conservative substitutions include those described above and by Dayhoff in *The Atlas of Protein Sequence and Structure* 5 (1978), and by Argos in EMBO J., 8:779–785 (1989). For example, amino acids belonging to one of the following groups represent conservative changes:

ala, pro, gly, gin, asn, ser, thr;

cys, ser, tyr, thr;

val, ile, leu, met, ala, phe;

lys, arg, his;

phe, tyr, trp, his; and asp, glu.

The present invention also relates to vectors which include polynucleotides of the present invention, host cells which are genetically engineered with vectors of the invention and the production of polypeptides of the invention by recombinant techniques. Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, or selecting transformants. The culture conditions, such as temperature, pH and the like, are those previously used with the host cell selected for expression, and will be apparent to the ordinarily skilled artisan. The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, non-chromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art. The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*. The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as *E. coil, Salmonella typhimurium*, Streptomyces; fungal cells, such as yeast; insect cells, such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, PRIT5 (Pharmacia). Eukaryotic: pWLneo, pSV2cat, pOG44, pXT1, pSG (Stratagene) pSVK3, pBPV, pMSG, PSVL (Pharmacia). However, any other plasmid or vector may be used as long as they are replicable and viable in the host. Promoter regions can be selected from any desired gene using CAT(chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothlonein-I. Selection of the appropriate vector and promoter is well within the level of ordinary skill in the art.

The present invention also relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually from about 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers. Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation, initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E.coli, Bacillus subtilis, Salmonella typhimurium and various species within the genera Pseudomonas, Streptomyces, and Staphylococcus, although others may also be employed as a matter of choice. Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Blotec, Madison, Wis., USA). These pBR322 "backbone" sections are combined with an appropriate promoter and the structural sequence to be expressed.

After transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required non-transcribed genetic elements.

The polypeptides of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptides of this invention may be a product of chemical synthetic-procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of this invention may be glycosylated with mammalian or other eukaryotic carbohydrates or may be non-glycosylated. Polypeptides of this invention may also include an initial methionine amino acid residue. An isolated or purified polypeptide of this invention, or biologically active portion thereof, is substantially free of other cellular material, or culture medium when produced by recombinant techniques, or substantially free of chemical precursors or other chemicals when chemically synthesized. Preferably, an isolated polypeptide of this invention is substantially free of cellular material and has less than about 30% (by dry weight) of non-polypeptide, or contaminating, material. When the polypeptide of this invention or a biologically active portion thereof is recombinantly produced, preferably culture medium represents less than about 30% of the volume of the polypeptide preparation. When this invention is produced by chemical synthesis, preferably the preparations contain less than about 30% by dry weight of chemical precursors or non-invention chemicals.

The polypeptides of this invention can be conveniently isolated as described in the specific examples below. A preparation of purified polypeptide is at least about 70% pure; preferably, the preparations are 85% through 99% pure. Purity of the preparations can be assessed by any means known in the art, such as SDS-polyacrylamide gel electrophoresis and Mass Spec/Liquid Chromatography.

Polynucleotide sequences encoding a polypeptide of this invention can be synthesized, in whole or in part, using chemical methods well known in the art (see, for example, Caruthers et al, *Nucl. Acids Res. Symp. Ser.* 215–223, 1980; Horn et al, *Nucl. Acids Res. Symp. Ser* 225–232, 1980). The polynucleotide that encodes the polypeptide can then be cloned into an expression vector to express the polypeptide.

As will be understood by those of skill in the art, it may be advantageous to produce the polypeptide-encoding nucleotide sequences possessing non-naturally occurring codons. For example, codons preferred by a particular prokaryotic or eukaryotic host can be selected to increase the rate of polypeptide expression or to produce an RNA transcript having desirable properties, such as a half-life which is longer than that of a transcript generated from the naturally occurring sequence.

The nucleotide sequences disclosed herein can be engineered using methods generally known in the art to alter the polypeptide-encoding sequences for a variety of reasons, including but not limited to, alterations which modify the closing, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Alternatively, the polypeptides of this invention can be produced using chemical methods to synthesize its amino acid sequence, such as by direct peptide synthesis using solid-phase techniques (see, for example, Merrifield, *J. Am. Chem. Soc.* 85, 2149–2154, 1963; Roberge et al, *Science*, 269, 202–204, 1995). Polypeptide synthesis can be performed using manual techniques or by automation. Automated synthesis can be achieved, for example, using Applied Biosystems 431A Peptide Synthesizer (Perkin Elmer). Optionally, fragments of the polypeptide can be separately synthesized and combined using chemical methods to produce a full-length molecule.

The newly synthesized polypeptide can be substantially purified by preparative high performance liquid chromatography (see, for example, Creighton, PROTEINS: STRUCTURES AND MOLECULAR PRINCILPLES, WH Freeman and Co., New York, N.Y., 1983). The composition of a synthetic polypeptide of the present invention can be confirmed by amino acid analysis or sequencing by, for example, the Edman degradation procedure (see, Creighton, supra). Additionally, any portion of the amino acid sequence of the polypeptide can be altered during direct synthesis and/or combined using chemical methods with sequences from other proteins to produce a variant polypeptide or a fusion polypeptide.

The polypeptides of the present invention, as a result of the ability to stimulate insulin secretion from pancreatic islet cells in vitro, and by causing a decrease in blood glucose in vivo, may be employed in treatment of type 2 Diabetes (non-insulin dependent diabetes mellitus). Also, the polypeptides may be used to prevent subjects with impaired glucose tolerance from proceeding to develop type 2 diabetes. In addition, the polypeptides of the invention may be used for treatment of asthma (Bolin et al Biopolymer 37:57–66 (1995); U.S. Pat. No. 5,677,419)(showing that polypeptide R3P0 is active in relaxing guinea pig tracheal smooth muscle); hypotension induction (VIP induces hypotension, tachycardia, and facial flushing in asthmatic patients (Morice, A. H., and Sever, P. S., Peptides 7:279–280 (1986); Morice, A., et al., The Lancet II, 1225–1227 (1983)), male reproduction problems (Siow, Y., et al., Effects of vasoactive intestinal peptide on human sperm motility, Arch. Androl. 1999 July–August; 43(1):67–71); as a anti-apoptosis/neuroprotective agent (Brenneman D. E., et al., VIP neurotrophism in the central nervous system: multiple effectors and identification of a femtomolar-acting neuroprotective peptide, Ann. N. Y. Acad. Sci. 1998 Dec. 11 ;865:207–12); cardioprotection during ischemic events (Kaffin R., et al., Protective role of intracoronary vasoactive intestinal peptide in ischemic and reperfused myocardium, J. Pharmacol. Exp. Ther. 1994 February;268(2):952–8; Das, D. K., et al., Coordinated role of vasoactive intestinal peptide and nitric oxide in cardioprotection, Ann. N. Y. Acad. Sci. 1998 Dec. 11;865:297–308), and finally as an anti-ulcer agent (Tuncel, et al., The protective effect of vasoactive intestinal peptide (VIP) on stress-induced gastric ulceration in rats, Ann. N. Y. Acad. Sci. 1998 Dec. 11;865:309–22.

The polypeptides of the present invention may be employed in combination with a suitable pharmaceutical carrier to comprise a pharmaceutical composition for parenteral administration. Such compositions comprise a therapeutically effective amount of the polypeptide and a pharmaceutically acceptable carrier or excipient. Such a carrier includes but is not limited to saline, buffered saline, dextrose, water, glycerol, ethanol, and combinations thereof. The formulation should suit the mode of administration. The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 350 ng (0.1 nmol)/kg body weight and in most cases they will be administered in an amount not in excess of about 35 ug (10 nmol)/kg body weight per day. In most cases, the dosage is from about 0.1 $\mu$g/kg to about 100 mg/kg body weight daily, taking into account the routes of administration, symptoms, etc. These numbers do not take into account the bioavailability of the peptide in vivo, in which case more or less may be used to attain the effective dose desired. One of ordinary skill in the art is able to determine through dosing experiments or other conventional means the gross amount to be used to produce an effective dosage.

A polypeptide of the invention may also be employed in accordance with the present invention by expression of such polypeptide in vivo, which is often referred to as "gene therapy." Thus, for example, cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Local delivery of the insulin secretagogues using gene therapy may provide the therapeutic agent to the target area, i.e., the pancreas. For instance a pancreas-specific promoter was used to create a beta-cell pancreatic tumor mouse model (Hanahan, D., Heritable formation of pancreatic beta-cell tumors in transgenic mice expressing recombinant insulin/simian virus 40 oncogenes, Nature 315(6015):115–22 (1985)).

Both in vitro and in vivo gene therapy methodologies are contemplated. Several methods for transferring potentially therapeutic genes to defined cell populations are known. See, e.g., Mulligan, "The Basic Science Of Gene Therapy", Science. 260: 926–31 (1993). These methods include:

1) Direct gene transfer. See, e.g., Wolff et al., "Direct Gene transfer Into Mouse Muscle In Vivo", Science, 247:1465–68 (1990);

2) Liposome-mediated DNA transfer. See, e.g., Caplen at al., "Liposome-mediated CFTR Gene Transfer To The Nasal Epithelium Of Patients With Cystic Fibrosis", Nature Med. 3: 39–46 (1995); Crystal, "The Gene As A Drug", Nature Med. 1:15–17 (1995); Gao and Huang, "A Novel Cationic Liposome Reagent For Efficient Transfection Of Mammalian Cells", Biochem. Biophys. Res. Comm., 179:280–85 (1991);

3) Retrovirus-mediated DNA transfer. See, e.g., Kay et al., "In Vivo Gene Therapy Of Hemophilia B: Sustained Partial Correction in Factor IX-Deficient Dogs", Science, 262:117–19 (1993); Anderson, "Human Gene Therapy", Science, 256:808–13 (1992).

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., All et al., "The Use Of DNA Viruses As Vectors For Gene Therapy", Gene Therapy, 1:367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. See Naldini et al, in vivo gene delivery and stable transduction of nondividing cells by a lentiviral vector, Science 272:263–7 (1996).

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19 (Ali et al., supra, p. 377).

In a preferred embodiment, the DNA encoding the polypeptide insulin secretagogues of this invention is used in gene therapy for disorders such as diabetes.

According to this embodiment, gene therapy with DNA encoding polypeptide insulin secretagogues or muteins of this invention is provided to a patient in need thereof, concurrent with, or immediately after diagnosis.

The skilled artisan will appreciate that any suitable gene therapy vector containing polypeptide insulin secretagogues, DNA or DNA of fragment, derivative or variant of polypeptide insulin secretagogues may be used in accordance with this embodiment. The techniques for constructing such a vector are known. See, e.g., Anderson, W. F., "Human Gene Therapy," Nature, 392 25–30 (1998); Verma, I. M., and Somia, N., "Gene Therapy—Promises, Problems, and Prospects," Nature, 389 239–242 (1998). Introduction of the polypeptide insulin secretagogues DNA-containing vector to the target site may be accomplished using known techniques.

The vector includes one or more promoters. Suitable promoters which may be employed include, but are not limited to, the retroviral LTR; the SV40 promoter; and the human cytomegalovirus (CMV) promoter described in Miller, et al., Biotechniques, 7(9): 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidinekinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which maybe transfected include, but are not limited to, the PE501, PA317, Ψ-2, Ψ-AM, PA12, T19-14X, VT-19-17-H2, ΨCRE, ΨCRIP, GP+E-86, GP+envAm12, and DAN cell lines as described in Miller, Human Gene Therapy, 1: 5–14 (1990), which is incorporated herein by reference in its entirety. The vector may transduce the packaging cells through any means known in the art. Such means include, but are not limited to, electroporation, The use of liposomes, and $CaPO_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequencers) encoding the polypeptide. Eukaryotic cells which may be transduced include, but are not limited to, embryonic stem cells, embryonic carcinoma cells, as well as hematopoletic stem cells, hepatocytes, fibroblasts, myoblasts, keratinocytes, endothelial cells, and bronchial epithelial cells.

A different approach to gene therapy is "transkaryotic therapy" wherein the patient's cells are treated ex vivo to induce the dormant chromosomal genes to produce the protein of interest after reintroduction to the patient. Transkaryotic therapy assumes the individual has a normal complement of genes necessary for activation. Transkaryotic therapy involves introducing a promoter or other exogenous regulatory sequence capable of activating the nascent genes, into the chromosomal DNA of the patients' cells ex vivo, culturing and selecting for active protein-producing cells, and then reintroducing the activated cells into the patient with the intent that they then become fully established. The "gene activated" cells then manufacture the protein of interest for some significant amount of time, perhaps for as long as the life of the patient. U.S. Pat. Nos. 5,641,670 and 5,733,761 disclose in detail this concept, and are hereby incorporated by reference in their entirety.

In order that this invention may be better understood, the following examples are set forth. These examples are for the purpose of illustration only, and are not to be construed as limiting the scope of the invention in any manner. All publications mentioned herein are incorporated by reference in their entirety.

EXAMPLE 1

Protocol for Rat Islet Isolation

Sprague Dawley rats (275–320 g) were used as the source of donor islets. Briefly, the pancreas was filled with 10 ml of cold reconstituted Liberase RI (Boehringer Manheim), harvested and incubated with additional 5 ml enzyme solution in water bath for 30 minutes. Tissue suspension was washed twice with cold 10% FBS/Hanks buffer (Gibco), resuspended in 8 ml 25% ficoll (Sigma) and then layered with 5 ml each of 23%, 20% and 11% ficoll. The islets in the 20% layer after centrifugation were removed, washed twice with cold 10% FBS/Hank buffer and resuspended in 10% FBS/RPMI 1640 media (Sigma).

EXAMPLE 2

Protocol for Assaying Peptide-induced Elevation of Insulin Levels in Rats

Wistar rats are fasted overnight (17 hrs) and then anesthetized with pentobarbital (0.1 ml/100 g BW). Glucose (0.4 g/kg dissolved in 1% human albumin-saline)+/−peptide (dissolved in 1% human albumin-saline) is injected intravenously into the tail vein. The rats are eye-bled 1 minute after the injection and 50–100 ul of the plasma are assayed for insulin level with the Linco RIA kit (Linco Research, Inc., St. Charles, Mo.).

EXAMPLE 3

Protocol for Determining the Effect of Peptides on Intraperitoneal Glucose Tolerance in Rats Wistar rats are fasted overnight and then anesthetized with pentobarbital. The rats were eye-bled (zero time) and the peptide (in 1% human albumin) was injected into the tail vein. Five minutes later, 1 g/kg of glucose (in saline) was injected intraperitoneally, and the rats were eye-bled after 15, 30 and 60 minutes. Plasma glucose levels were determined using the Technicon Axon autoanalyzer, Bayer Diagnosics division of Bayer Corporation, Tarrytown N.Y., operated using Method No. SM4-2143F90"Glucose".

EXAMPLE 4

Protocol for Determining the Effect of Peptides on Intestinal Water Retention in Rats Male rats were fasted for 24 hours, and their water bottles were taken away for 2–3 hours before the start of the experiment. Peptide or saline was injected subcutaneously into conscious rats. The rats were euthanized with $CO_2$ 10 minutes after dosing, and the small intestine dissected out and weighed (1). The intestine was cut open, the water in the lumen absorbed with filter paper, and the intestine re-weighed (2). The amount of intestinal water (g)=weight (1)−weight (2).

EXAMPLE 5

Peptide Synthesis Methodology

The following general procedure was followed to synthesize some of the polypeptides of the invention. Peptide synthesis was carried out by the FMOC/t-Butyl strategy (Peptide Synthesis Protocols (1994), Volume 35 by Michael W. Pennington & Ben M. Dunn) under continuous flow conditions using Rapp-Polymere PEG-Polystyrene resins (Rapp-Polymere, Tubingen, Germany). At the completion of synthesis, peptides are cleaved from the resin and de-protected using $TFA/DTT/H_2O$/Triisopropyl silane (88/5/5/2). Peptides were precipitated from the cleavage cocktail using cold diethyl ether. The precipitate was washed three times with the cold ether and then dissolved in 5% acetic acid prior to lyophilization. Peptides were checked by reversed phase chromatography on a YMC-Pack ODS-AQ column (YMC, Inc., Wilmington, N.C.) on a Waters ALLIANCE® system (Waters Corporation, Milford, Mass.) using water/acetonitrile with 3% TFA as a gradient from 0% to 100% acetonitrile, and by MALDI mass spectrometry on a VOYAGER DE™ MALDI Mass Spectrometer, (model 5-2386-00, PerSeptive BioSystems, Framingham, Mass.). Matrix buffer (50/50 dH2O/acetonitrile with 3% TFA) peptide sample added to Matrix buffer 1/1. Those peptides not meeting the purity criteria of >95% are purified by reversed phase chromatography on a Waters Delta Prep 4000 HPLC system (Waters Corporation, Milford, Mass.).

EXAMPLE 6

Peptide Cloning

The recombinant expression of VIP has been attempted previously with mixed results. Simoncsits et al (*Eur. J. Biochem.* 178: 343–350, (1988)) expressed Leu$^{17}$, Gly$^{29}$-VIP or Leu$^{17}$Gly$^{29}$ Lys$^{30}$Arg$^{31}$-VIP as a C-terminal fusion to the N-terminal part of the *E. coli* β-alactosidase gene in *E. coli*. The removal of the methionine at position 17 eliminates a CNBR cleavage site. C-terminal addition of Gly or Gly-Lys-Arg was designed for potential in vivo C-terminal amidation by mammalian PAMase. Upon CNBR cleavage of the fusion proteins at the methionine introduced N-terminal to the VIP mutants, free VIP mutants were purified and shown to possess similar activities as the native VIP, although the activities were measured only at saturating concentrations of the peptides. Ralngeaud et al (*Biochimie* 78: 14–25 (1996)) expressed VIP as polymeric C-terminal fusions to glutathione S-transferase (GST) in *E. coli*. The free polymeric or monomeric VIP peptides were released upon sequential cleavages by Factor Xa and hydroxylamine. The requirement for the two-step cleavage led to inefficiency and a mixture of products. Polyrneric or monomeric VIP peptides produced by this method were less active than the native VIP. An improved version of the construct using only Factor Xa cleavage yielded a VIP mutant with a seven residue C-terminal extension that was also less active than the native VIP (Ottavi et al, *Biochimie* 80: 289–293 (1998)). No expression of PACAP has been reported to date. To establish a robust method for expressing PACAP, VIP, and their mutants, their genetic codes were cloned C-terminal to GST with a single Factor Xa recognition site separating the monomeric peptide and GST. The gene encoding Factor Xa recognition site fused to DNA sequence of the peptide to be produced has been synthesized by hybridizing two overlapping single-stranded DNA fragments (70–90 mers) containing a Bam HI or Xho I restriction enzyme site immediately 5' to the DNA sequence of the gene to be cloned, followed by DNA synthesis of the opposite strands via the large fragment of DNA polymerase I (Life Technologies, Inc., Gaithersburg, Md.). The DNA sequence chosen for each gene was based on the reverse translation of the designed amino acid sequence of each peptide. In some cases, the gene encoding the peptide is generated by PCR mutagenesis (Picard, V, et al., *Nucleic Acids Res* 22: 2587–91 (1994); Sambrook, J., Fritsch, E. F., & Maniatis, T. (1989) Molecular Cloning: A Laboratory Manual, 2nd ed., Cold Spring Harbor Laboratory Press, New York) of a gene already made by the method described above. The double-stranded product is then digested by Bam HI and Xho I and ligated into pGEX-6P-1 (Amersham Pharmacia Biotech) which has also been cleaved by Bam HI and Xho I. The DNA sequences of the cloned peptide genes are listed in FIG. 8.

For example, when DNA sequences of SEQ ID NOs: 54, 55, and 56 are doned into pGEX-6P-1, the following polypeptide sequences were expressed as fusions with glutathione S-transferase (GST):

PACAP38: IEGRHSDGIFTDSYSRYRKQMAVKKY-LMVLGKRYKQRVKNK (SEQ ID NO:2)

VIP: IEGRHSDAVFTDNYTRLRKQMAVKKYLNSILN (SEQ ID NO:1)

R3P3: IEGRHSDAVFTENYTKLRKOLAAKKY-LNDLKKGGT (SEQ ID NO:8)

Figure 3:
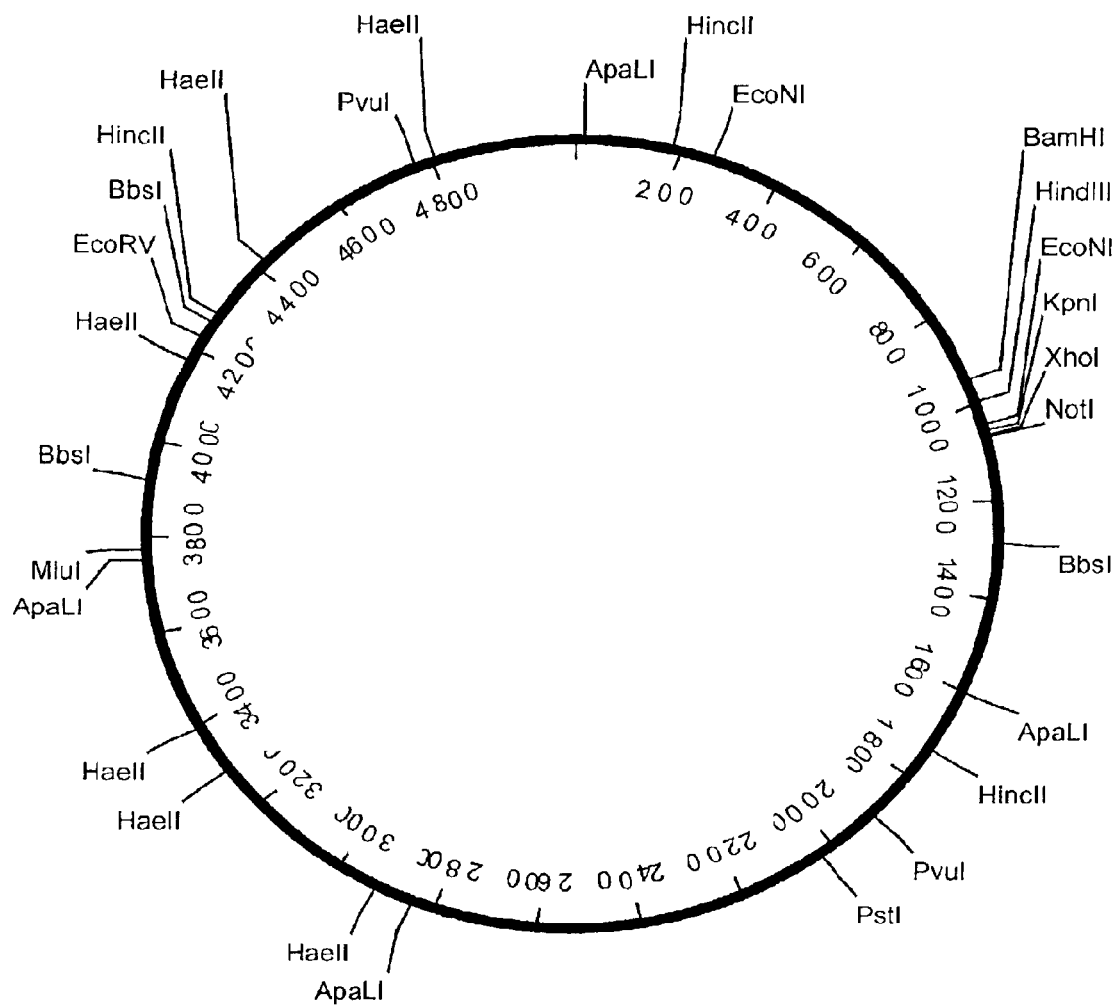
FIG. 3 is a restriction map of a typical plasmid containing the GST-peptide fusion.

A restriction map of a typical plasmid containing the GST-peptide fusion is shown as FIG. 3.

EXAMPLE 7

Peptide Recombinant Expression and Purification

BL21 cells (Stratagene) transformed with the GST-peptide fusion containing plasmids were grown at 37° C. until OD$_{600}$ reached 0.6 to 1.0 and induced by 1 mM IPTG (Life Technologies) for 2 hours at 37° C. 2 L of cells were spun at 7,700 g for 15 minutes, weighed, and stored at −20° C. for at least 3 hours. The frozen cell pellet was resuspended in 100 mL ice-cold PBS with 250 μl of protease inhibitor cocktail (Cat No. P-8465, Sigma Chemical) per gram of cells, sonicated at 3× for 1 minute with 15 second breaks. Cellular debris were spun down at 10,000 g for 20 minutes. The supernatant was mixed with 2 mL of 50% Glutathione Sepharose 4B resin (Pharmacia) on a shaker overnight at 4° C. The resins were spun down at 1,500 g for 15 minutes, packed into empty Poly-Prep Chromatography Columns (Bio-Rad), washed with 30 mL PBS followed by 10 mL of FactorXa buffer (1 mM CaCl$_2$, 100 mM NaCl, and 50 mM Tris-HCl, pH 8.0). The peptides were cleaved off the column by 60 units of Factor Xa (Pharmacia) in 1 mL of Factor Xa buffer for overnight at 4° C. and run on C18 HPLC (Beckman System Gold), using a 2 mL loop and flow rate of 2 mL/min with the following program: 10 minutes of Buffer A (0.1% TFA/H$_2$O), 30 minutes of gradient to Buffer B (0.1% TFA/ACN), 10 minutes of Buffer A, 10 minutes of gradient, and 10 minutes of Buffer A. Peak fractions (1 mL each) were collected and screened by 10–20% Tricine-SDS gel electrophoresis. Fractions containing the peptides of Table 1 were pooled and dried down. Typical yields are several hundred micrograms of free peptides per liter of *E. coli* culture. Recombinant peptides have been shown to have the same activities as their synthetic versions.

The following table contains some selected polypeptides made according to the Peptide Synthesis protocol discussed above (example 5), or recombinantly as described in Example 7. Peptides produced by the recombinant method are denoted with a small letter "r" in front of the peptide designator. Peptides produced by both recombinant and synthetic means are noted by asterisks next to their Peptide No's. Peptides R3P0 and R3P4 were reported by Bolin, et al. (Biopolymers 37: 57–66 (1995); U.S. Pat. No. 5,677,419).

TABLE 1

| Peptide No. | Sequence | SEQ ID NO: |
|---|---|---|
| R3P0 | Ac-HSDAVFTENYTKLRKQNleAAKKYLNDLKKGGT-NH$_2$ | 5 |
| R3P1 | Ac-HSDAVFTENYTKLRKQLAAKKYLNDLKKGGT-NH$_2$ | 6 |
| R3P2 | Ac-HSDAVFTENYTKLRKQLAAKKYLNDLKKGGT | 7 |

TABLE 1-continued

| Peptide No. | Sequence | SEQ ID NO: |
|---|---|---|
| rR3P3* | HSDAVFTENYTKLRKQLAAKKYLNDLKKGGT | 8 |
| R3P4 | Ac-HSDAVFTEN(CH$_3$O—Y)TKLRKQNleAAKKYLNDLKK-NH$_2$ | 9 |
| R3P5 | HSDAVFTENYTKLRKQLAAKKYLNDLKK | 10 |
| R3P8 | HSDAVFTDNYTRLRKQMAVKKYLNSIKK-NH$_2$ | 11 |
| rR3P9* | HSDAVFTDNYTRLRKQMAVKKYLNSIKKGGT | 12 |
| R3P10 | HSDAVFTENYTKLRKQLAAKKYLNDLLNGGT | 13 |
| R3P11 | HSDAVFTDNYTKLRKQLAAKKYLNDILNGGT | 14 |
| R3P12* | HSDAVFTDNYTRLRKQLAAKKYLNDIKKGGT | 15 |
| R3P13 | HSDAVFTDNYTRLRKQLAAKKYLNDIKK-NH$_2$ | 16 |
| R3P14 | HSDAVFTDNYTRLRKQMAVKKYLNDLKKGGT | 17 |
| R3P19 | HSDAVFTDNYTRLRKQLAAKKYLNDLKKGGTSWCEPGWCR | 18 |
| R3P20 | HSDAVFTDNYTRLRKQMAAKKYLNDIKKGGT | 19 |
| R3P21 | HSDAVFTDNYTRLRKQLAVKKYLNDIKKGGT | 20 |
| R3P22 | HSDAVFTDNYTRLRKQLAAKKYLNSIKKGGT | 21 |
| R3P24 | HSDAVFTDNYTRLRKQLAAKKYLNDIKNGGT | 22 |
| R3P25 | HSDAVFTDNYTRLRKQLAVKKYLNSIKKGGT | 23 |
| R3P26 | HSDAVFTDNYTRLRKQMAAKKYLNSIKKGGT | 24 |
| R3P29 | HSDAVFTDNYTRLRKQLAVKKYLNDIKNGGT | 25 |
| R3P30 | HSDAVFTDNYTRLRKQLAAKKYLNSIKNGGT | 26 |
| R3P31 | HSDAVFTDNYTRLRKQLAAKKYLNDIKKGG | 27 |
| R3P32 | HSDAVFTDNYTRLRKQLAAKKLNDIKKG | 28 |
| rR3P33* | HSDAVFTDNYTRLRKQLAAKKYLNDIKK | 29 |
| R3P34 | HSDAVFTDNYTRLRKQLAAKKYLNDIKKQ | 30 |
| R3P35 | HSDAVFTDNYTRLRKQLAAKKYLNDIKKNQ | 31 |
| R3P36 | HSDAVFTDNYTRLRKQLAAKKYLNDIKKKRY | 32 |
| rR3P41 | HSDAVFTDNYTRLRKQMAVKKYLNSIKK | 33 |
| rR3P42 | HSDAVFTDNYTRLRKQMAVKKYLNSIKN | 34 |
| rR3P43 | HSDAVFTDNYTRLRKQMAVKKYLNSILK | 35 |
| rR3P44 | HSDAVFTDNYTRLRKQMAVKKYLNSILN | 36 |
| rR3P45 | HSDAVFTDNYTRLREQMAVKKYLNSILN | 37 |
| rR3P46 | HSDAVFTDNYTRLRKQLAVKKYLNSILN | 38 |
| rR3P47 | HSDAVFTDNYTRLRKQMAAKKYLNSILN | 39 |
| rR3P48 | HSDAVFTDNYTRLRKQMAVKKYLNDILN | 40 |
| rR3P49 | HSDAVFTDNYTRLRKQMAAKKYLNSIKN | 41 |
| rR3P50 | HSDAVFTDNYTRLRKQMAAKKYLNSILK | 42 |
| rR3P51* | HSDAVFTDNYTRLRKQMAAKKYLNSIKK | 43 |
| rR3P52 | HSDAVFTDNYTRLRKQMAAKKYLNSIKKKRY | 44 |
| rR3P53* | HSDAVFTDNYTRLRKQMAAKKYLNSIKKKR | 45 |
| rR3P54 | HSDAVFTDNYTRLRKQMAAKKYLNSIKKK | 46 |
| rR3P55* | HSDAVFTDNYTRLRKQMAAKKYLNSIKNKRY | 47 |
| rR3P56 | HSDAVFTDNYTRLRKQMAVKKYLNSIKKKRY | 48 |
| rR3P57 | HSDAVFTDNYTRLRKQMAVKKYLNSIKKKR | 49 |
| rR3P58 | HSDAVFTDNYTRLRKQMAVKKYLNSIKKK | 50 |
| rR3P59 | HSDAVFTDNYTRLRKQMAVKKYLNSIKNKRY | 51 |
| rR3P60 | HSDAVFTDNYTRLRKQVAAKKYLQSIKK | 52 |
| rR3P61 | HSDAVFTDNYTRLRKQIAAKKYLQTIKK | 53 |
| R3P6 | HSDGIFTESYSRYRKQMAVKKYLAALKKKRYKQRVKNK | 57 |
| R3P7 | HSDAVFTENYTRLRKQMAVKKYLNSLKK-NH$_2$ | 58 |
| R3P15 | HSDGIFTDSYSRYRKQMAVKKYLSAVRHGQT-NH$_2$ | 59 |
| R3P16 | HSDGIFTDSYSRYRKQMAVKKYLAAVKQGGT-NH$_2$ | 60 |
| R3P17 | HSDGIFTDSYSRYRKQMAVKKYLAAVKKYLAAVRHG-NH$_2$ | 61 |
| R3P18 | SECEPGWCRHSDAVFTENYTKLRKQLAAKKYLNDLKKGGT | 62 |
| R3P23 | HSDAVFTDNYTRLRKQLAAKKYLNDILKGGT | 63 |
| R3P27 | HSDAVFTDNYTRLRKQLAAKKYLNDILNGGT | 64 |
| R3P28 | HSDAVFTDNYTRLRKQLAAKKYLNDILNGGT | 65 |
| R3P37 | HSDGIFTDSYSRYRKQLAAKKYLADVKKGGT | 66 |
| R3P38 | HSDGIFTDSYSRYRKQLAAKKYLADVKK | 67 |
| R3P39 | HSDGIFTDSYSRYRKQLAVKKYLADVKK | 68 |
| R3P40 | HSDGIFTDSYSRYRKQMAVKKYLADVKK | 69 |
| R3P62 | HSDAVFTDNYTRLRKQVAAKKYLNSIKK | 70 |
| R3P65 | HSDAVFTDNYTRLRKQMAAKKYLNSIKNKR | 71 |
| R3P66 | HSDAVFTDNYTRLRKQVAAKKYLQSIKNKRY | 72 |
| R3P67 | HSDAVFTDNYTRLRKQLAAKKYLNSIKNKRY | 73 |
| R3P68 | HSDAVFTDNYTRLRKQVAAKKYLNSIKNKRY | 74 |
| R3P69 | HSDAVFTDNYTRLRKQMAAKKYLQSIKNKRY | 75 |
| R3P70 | HSDAVFTDNYTRLRKQVAAKKYLNTNKNKRY | 76 |
| R3P71 | HSDAVFTDQYTRLRKQMAAKKYLNSIKNKRY | 77 |
| R3P72 | HSDAVFTDNYTRLRKQLAAKKYLNTIKNKRY | 78 |
| R3P73 | HSDAVFTDNYTRLRKQMAAHKYLNSIKNKRY | 79 |
| R3P74 | HSDAVFTDNYTRLRKQMAAKHYLNSIKNKRY | 80 |
| R3P75 | HSDAVFTDQYTRLRKQLAAHKYLNTIKNKRY | 81 |
| R3P76 | HSDAVFTDQYTRLRKQLAAKHYLNTIKNKRY | 82 |
| R3P77 | HSDAVFTDNYTRLRKQVAAKKYLQSIKKKR | 83 |
| R3P78 | HSDAVFTDNYTRLRKQVAAKKYLNSIKKKR | 84 |
| R3P79 | HSDAVFTDNYTRLRKQVAAKKYLNSIKNKRY | 85 |
| R3P80 | HSDAVFTDNYTRLRKQVAVKKYLSIKKKR | 86 |

TABLE 1-continued

| Peptide No. | Sequence | SEQ ID NO: |
|---|---|---|
| R3P81 | HSDAVFTDNYTRLRKQVAVKKYLQSIKKK | 87 |
| R3P82 | HSDAVFTDNYTRLRKQVAVKKYLQSIKNKRY | 88 |
| R3P83 | HSDAVFTDNDYTRLRKQVAAKKYLQSILKKRY | 89 |
| R3P84 | HSDAVFTDNYTRLRKQVAAKKYLQSILKKR | 90 |
| R3P85 | HSDAVFTDNYTRLRKQVAAKKYLQSILKK | 91 |
| R3P86 | HSDAVFTDNYTRLRKQVAAKKYLQSIKNK | 92 |
| R3P87 | HSDAVFTDNYTRLRKQVAVKKYLQSILKKRY | 93 |
| R3P88 | HSDAVFTDNYTRLRKQVAVKKYLQSILKKR | 94 |
| R3P89 | HSDAVFTDNYTRLRKQVAVKKYLQSILKK | 95 |
| R3P92 | HSDAVFTDNYTRLRKQVAAKKYLQSILNKRY | 97 |
| R3P93 | HSDAVFTDNYTRLRKQVAAKKYLQSILNKR | 98 |
| R3P94 | HSDAVFTDNYTRLRKQVAAKKYLQSILNK | 99 |
| rR3P97 | HSDAVFTDNYTRLRKQMACKKYLNSIKNKR | 100 |
| rR3P98 | HSDAVFTDNYTRLRKQMADKKYLNSIKNKR | 101 |
| rR3P99 | HSDAVFTDNYTRLRKQMAEKKYLNSIKNKR | 102 |
| rR3P100 | HSDAVFTDNYTRLRKQMAFKKYLNSIKNKR | 103 |
| rR3P101 | HSDAVFTDNYTRLRKQMAGKKYLNSIKNKR | 104 |
| rR3P102 | HSDAVFTDNYTRLRKQMAHKKYLNSIKNKR | 105 |
| rR3P103 | HSDAVFTDNYTRLRKQMAIKKYLNSIKNKR | 106 |
| rR3P104 | HSDAVFTDNYTRLRKQMAKKKYLNSIKNKR | 107 |
| rR3P105 | HSDAVFTDNYTRLRKQMMALKKYLNSIKNKR | 108 |
| rR3P106 | HSDAVFTDNYTRLRKQMAMKKYLNSIKNKR | 109 |
| rR3P107 | HSDAVFTDNYTRLRKQMANKKYLNSIKNKR | 110 |
| rR3P108 | HSDAVFTDNYTRLRKQMAPKKYLNSIKNKR | 111 |
| rR3P109 | HSDAVFTDNYTRLRKQMAQKKYLNSIKNKR | 112 |
| rR3P110 | HSDAVFTDNYTRLRKQMARKKYLNSIKNKR | 113 |
| rR3P111 | HSDAVFTDNYTRLRKQMMASKKYLNSIKNKR | 114 |
| rR3P112 | HSDAVFTDNYTRLRKQMATKKYLNSIKNKR | 115 |
| rR3P113 | HSDAVFTDNYTRLRKQMAVKKYLNSIKNKR | 116 |
| rR3P114 | HSDAVFTDNYTRLRKQMAWKKYLNSIKNKR | 117 |
| rR3P115 | HSDAVFTDNYTRLRKQMAYKKYLNSIKNKR | 118 |
| rR3P116 | HSDAVFTDNYTRLRKQMAAKKYLNSIANKR | 119 |
| rR3P117 | HSDAVFTDNYTRLRKQMAAKKYLNSICNKR | 120 |
| rR3P118 | HSDAVFTDNYTRLRKQMAAKKYLNSIDNKR | 121 |
| rR3P119 | HSDAVFTDNYTRLRKQMAAKKYLNSIENKR | 122 |
| rR3P120 | HSDAVFTDNYTRLRKQMAAKKYLNSIFNKR | 123 |
| rR3P121 | HSDAVFTDNYTRLRKQMAAKKYLNSIGNKR | 124 |
| rR3P122 | HSDAVFTDNYTRLRKQMAAKKYLNSIHNKR | 125 |
| rR3P123 | HSDAVFTDNYTRLRKQMAAKKYLNSIINKR | 126 |
| rR3P124 | HSDAVFTDNYTRLRKQMAAKKYLNSIMNKR | 127 |
| rR3P125 | HSDAVFTDNYTRLRKQMAAKKYLNSINNKR | 128 |
| rR3P126 | HSDAVFTDNYTRLRKQMAAKKYLNSIPNKR | 129 |
| rR3P127 | HSDAVFTDNYTRLRKQMAAKKYLNSIQNKR | 130 |
| rR3P128 | HSDAVFTDNYTRLRKQMAAKKYLNSIRNKR | 131 |
| rR3P129 | HSDAVFTDNYTRLRKQMAAKKYLNSISNKR | 132 |
| rR3P130 | HSDAVFTDNYTRLRKQMAAKKYLNSITNKR | 133 |
| rR3P131 | HSDAVFTDNYTRLRKQMAAKKYLNSIVNKR | 134 |
| rR3P132 | HSDAVFTDNYTRLRKQMAAKKYLNSIWNKR | 135 |
| rR3P133 | HSDAVFTDNYTRLRKQMAAKKYLNSIYNKR | 136 |
| rR3P134 | HSDAVFTDNYTRLRKQMAAKKYLNSIKNAR | 137 |
| rR3P135 | HSDAVFTDNYTRLRKQMAAKKYLNSIKNCR | 138 |
| rR3P136 | HSDAVFTDNYTRLRKQMAAKKYLNSIKNDR | 139 |
| rR3P137 | HSDAVFTDNYTRLRKQMAAKKYLNSIKNER | 140 |
| rR3P138 | HSDAVFTDNYTRLRKQMAAKKYLNSIKNFR | 141 |
| rR3P139 | HSDAVFTDNYTRLRKQMAAKKYLNSIKNGR | 142 |
| rR3P140 | HSDAVFTDNYTRLRKQMAAKKYLNSIKNHR | 143 |
| rR3P141 | HSDAVFTDNYTRLRKQMAAKKYLNSIKNIR | 144 |
| rR3P142 | HSDAVFTDNYTRLRKQMAAKKYLNSIKNLR | 145 |
| rR3P143 | HSDAVFTDNYTRLRKQMAAKKYLNSIKNMR | 146 |
| rR3P144 | HSDAVFTDNYTRLRKQMAAKKYLNSIKNNR | 147 |
| rR3P145 | HSDAVFTDNYTRLRKQMAAKKYLNSIKNPR | 148 |
| rR3P146 | HSDAVFTDNYTRLRKQMAAKKYLNSIKNQR | 149 |
| rR3P147 | HSDAVFTDNYTRLRKQMAAKKYLNSIKNRR | 150 |
| rR3P148 | HSDAVFTDNYTRLRKQMAAKKYLNSIKNSR | 151 |
| rR3P149 | HSDAVFTDNYTRLRKQMAAKKYLNSIKNTR | 152 |
| rR3P150 | HSDAVFTDNYTRLRKQMAAKKYLNSIKNVR | 153 |
| rR3P151 | HSDAVFTDNYTRLRKQMAAKKYLNSIKNWR | 154 |
| rR3P152 | HSDAVFTDNYTRLRKQMAAKKYLNSIKNYR | 155 |
| rR3P153 | HSDAVFTDNYTRLRKQMAAKKYLNSIKNKA | 156 |
| rR3P155 | HSDAVFTDNYTRLRKQMAAKKYLNSIKNKD | 157 |
| rR3P156 | HSDAVFTDNYTRLRKQMAAKKYLNSIKNKE | 158 |
| rR3P157 | HSDAVFTDNYTRLRKQMAAKKYLNSIKNKF | 159 |
| rR3P158 | HSDAVFTDNYTRLRKQMAAKKYLNSIKNKG | 160 |
| rR3P159 | HSDAVFTDNYTRLRKQMAAKKYLNSIKNKH | 161 |
| rR3P160 | HSDAVFTDNYTRLRKQMAAKKYLNSIKNKI | 162 |
| rR3P161 | HSDAVFTDNYTRLRKQMAAKKYLNSIKNKK | 163 |

TABLE 1-continued

| Peptide No. | Sequence | SEQ ID NO: |
|---|---|---|
| rR3P162 | HSDAVFTDNYTRLRKQMAAKKYLNSIKNKL | 164 |
| rR3P163 | HSDAVFTDNYTRLRKQMAAKKYLNSIKNKM | 165 |
| rR3P164 | HSDAVFTDNYTRLRKQMAAKKYLNSIKNKN | 166 |
| rR3P165 | HSDAVFTDNYTRLRKQMAAKKYLNSIKNKP | 167 |
| rR3P166 | HSDAVFTDNYTRLRKQMAAKKYLNSIKNKQ | 168 |
| rR3P167 | HSDAVFTDNYTRLRKQMAAKKYLNSIKNKS | 169 |
| rR3P168 | HSDAVFTDNYTRLRKQMAAKKYLNSIKNKT | 170 |
| rR3P169 | HSDAVFTDNYTRLRKQMAAKKYLNSIKNKV | 171 |
| rR3P170 | HSDAVFTDNYTRLRKQMAAKKYLNSIKNKW | 172 |
| rR3P171 | HSDAVFTDNYTRLRKQMAAKKYLNSIKNKY | 173 |
| rR3P172 | HSDAVFTDNYTRLRKQMAAKKYLQSIKNKRYSWCEPGWCR | 174 |
| rR3P173 | HSDAVFTDDYTRLRKEVAAKKYLESIKDKRY | 175 |
| PAC1 | ESDGIFTDSYSRYRKQMAVKKYLAAVL-NH$_2$ | 176 |
| PAC2 | HKDGIFTDSYSRYRKQMAVKKYLAAVL-NH$_2$ | 177 |
| PAC3 | HSKGIFTDSYSRYRKQMAVKKYLAAVL-NH$_2$ | 178 |
| PAC4 | HSDKIFTDSYSRYRKQMAVKKYLAAVL-NH$_2$ | 179 |
| PAC5 | HSDKFTDSYSRYRKQMAVKKYLAAVL-NH$_2$ | 180 |
| PAC6 | HSDGIKTDSYSRYRKQMAVKKYLAAVL-NH$_2$ | 181 |
| PAC7 | HSDGIFKDSYSRYRKQMAVKKYLAAVL-NH$_2$ | 182 |
| PAC8 | HSDGIFTKSYSRYRKQMAVKKYLAAVL-NH$_2$ | 183 |
| PAC9 | HSDGIFTDKYSRYRKQMAVKKYLAAVL-NH$_2$ | 184 |
| PAC10 | HSDGIFTDSKSRYRKQMAVKKYLAAVL-NH$_2$ | 185 |
| PAC11 | HSDGIFTDSYKRYRKQMAVKKYLAAVL-NH$_2$ | 186 |
| PAC12 | HSDGIFTDSYSEYRKQMAVKKYLAAVL-NH$_2$ | 187 |
| PAC13 | HSDGIFTDSYSRKRKQMAVKKYLAAVL-NH$_2$ | 188 |
| PAC14 | HSDGIFTDSYSRYEKQMAVKKYLAAVL-NH$_2$ | 189 |
| PAC15 | HSDGIFTDSYSRYREQMAVKKYLAAVL-NH$_2$ | 190 |
| PAC16 | HSDGIFTDSYSRYRKKMAVKKYLAAVL-NH$_2$ | 191 |
| PAC17 | HSDGIFTDSYSRYRKQKAVKKYLAAVL-NH$_2$ | 192 |
| PAC18 | HSDGIFTDSYSRYRKQMAVKKYLAAVL-NH$_2$ | 193 |
| PAC19 | HSDGIFTDSYSRYRKQMAKKKYLAAVL-NH$_2$ | 194 |
| PAC20 | HSDGIFTDSYSRYRKQMAVEKYLAAVL-NH$_2$ | 195 |
| PAC21 | HSDGIFTDSYSRYRKQMAVKEYLAAVL-NH$_2$ | 196 |
| PAC22 | HSDGIFTDSYSRYRKQMAVKKKLAAVL-NH$_2$ | 197 |
| PAC23 | HSDGIFTDSYSRYRKQMAVKKYKAAVL-NH$_2$ | 198 |
| PAC24 | HSDGIFTDSYSRYRKQMAVKKYLKAVL-NH$_2$ | 199 |
| PAC25 | HSDGIFTDSYSRYRKQMAVKKYLAKVL-NH$_2$ | 200 |
| PAC26 | HSDGIFTDSYSRYRKQMAVKKYLAAKL-NH$_2$ | 201 |
| PAC27 | HSDGIFTDSYSRYRKQMAVKKYLAAVK-NH$_2$ | 202 |
| rR3P174 | HSDAVFTDNYTRLRKQMAAKKYLNSIKNRI | 322 |
| rR3P175 | HSDAVFTDNYTRLRKQMAGKKYLNSIKNRI | 323 |
| rR3P176 | HSDAVFTDNYTRLRKQMAKKKYLNSIKNRI | 324 |
| rR3P177 | HSDAVFTDNYTRLRKQMARKKYLNSIKNRI | 325 |
| rR3P178 | HSDAVFTDNYTRLRKQMASKKYLNSIKNRI | 326 |
| rR3P179 | HSDAVFTDNYTRLRKQMAAKKYLNSIPNRI | 327 |
| rR3P180 | HSDAVFTDNYTRLRKQMAGKKYLNSIPNRI | 328 |
| rR3P181 | HSDAVFTDNYTRLRKQMAKKKYLNSIPNRI | 329 |
| rR3P182 | HSDAVFTDNYTRLRKQMARKKYLNSIPNRI | 330 |
| rR3P183 | HSDAVFTDNYTRLRKQMASKKYLNSIPNRI | 331 |
| rR3P184 | HSDAVFTDNYTRLRKQMAAKKYLNSIQNRI | 332 |
| rR3P185 | HSDAVFTDNYTRLRKQMAGKKYLNSIQNRI | 333 |
| rR3P186 | HSDAVFTDNYTRLRKQMAKKKYLNSIQNRI | 334 |
| rR3P187 | HSDAVFTDNYTRLRKQMARKKYLNSIQNRI | 335 |
| rR3P188 | HSDAVFTDNYTRLRKQMASKKYLNSIQNRI | 336 |
| rR3P189 | HSDAVFTDNYTRLRKQMAAKKYLNSIRNRI | 337 |
| rR3P190 | HSDAVFTDNYTRLRKQMAGKKYLNSIRNRI | 338 |
| rR3P191 | HSDAVFTDNYTRLRKQMAKKKYLNSIRNRI | 339 |
| rR3P192 | HSDAVFTDNYTRLRKQMARKKYLNSIRNRI | 340 |
| rR3P193 | HSDAVFTDNYTRLRKQMASKKYLNSIRNRI | 341 |

EXAMPLE 8

Insulin Secretion by Rat Islets

Peptide R3P3 (0.1–100 nM) stimulates insulin secretion from isolated rat islets in a glucose-dependent fashion. These studies compare the effects on islet cells of R3P3 peptide and GLP-1.

Figure 4A:
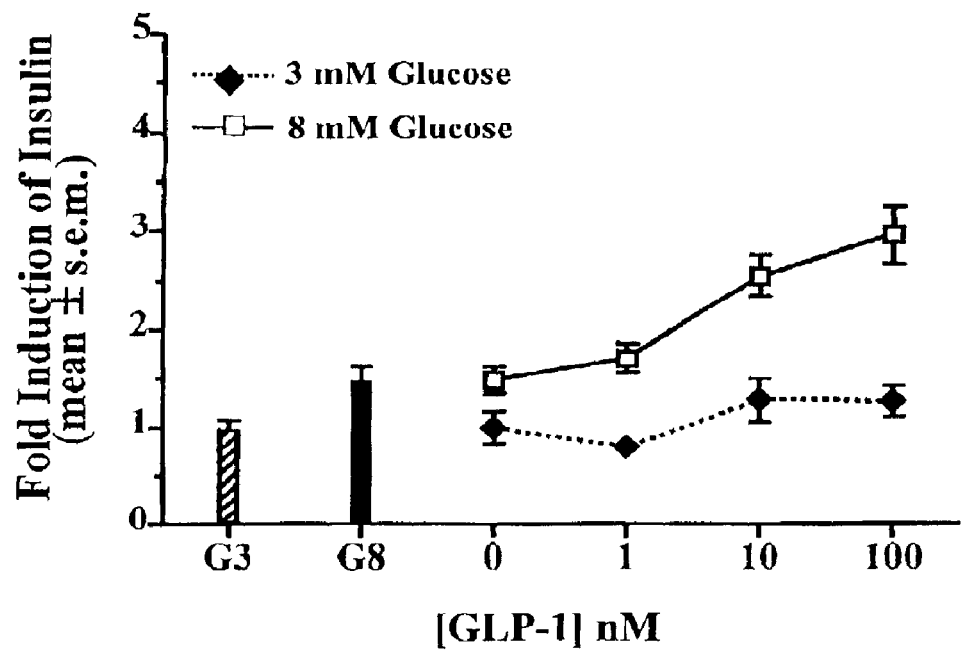
FIGS. 4A–4B are graphs showing the effects of GLP-1 or R3P3 on insulin release from rat islets in vitro.
Figure 4B:
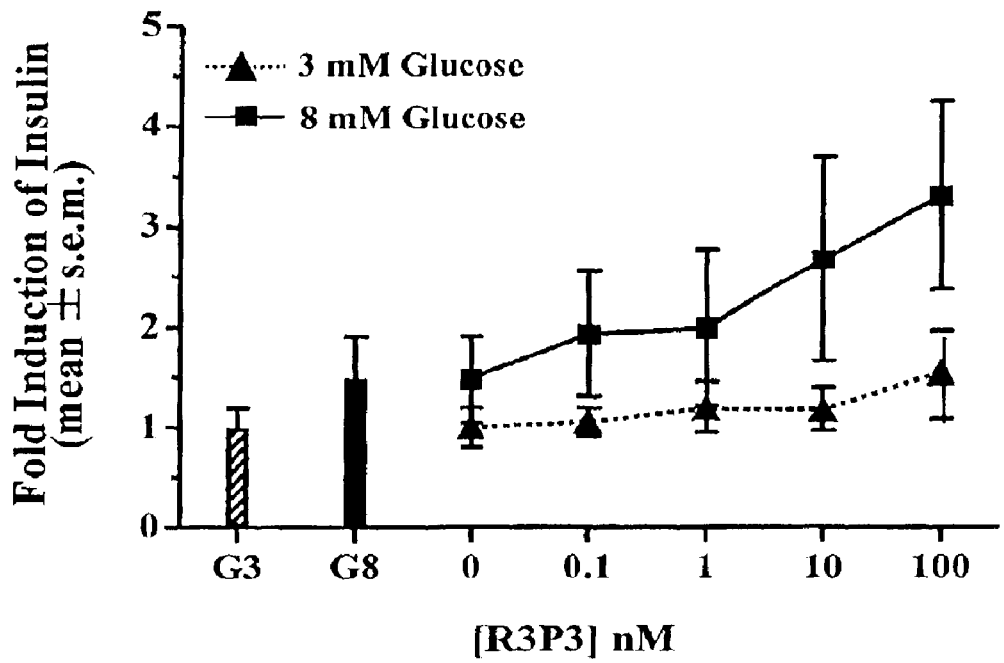

Rat islets were isolated and treated with GLP-1 or R3P3 at either 3 or 8 mM glucose in the medium in accordance with the rat islet protocol described above in example 1. As shown by FIGS. 4A–4B, peptide R3P3 significantly enhances the release of insulin from islets in a concentration-dependent fashion and this effect is similar to that of GLP-1, a known insulin secretagogue.

EXAMPLE 9

In vivo Insulin and Glucose Response

As shown in Tables 2 and 3 below, polypeptides that activate the R3 receptor also potentiate glucose-induced increase in plasma insulin levels when compared to glucose alone. This increase in insulin causes concomitant decrease in plasma glucose.

Figure 5:
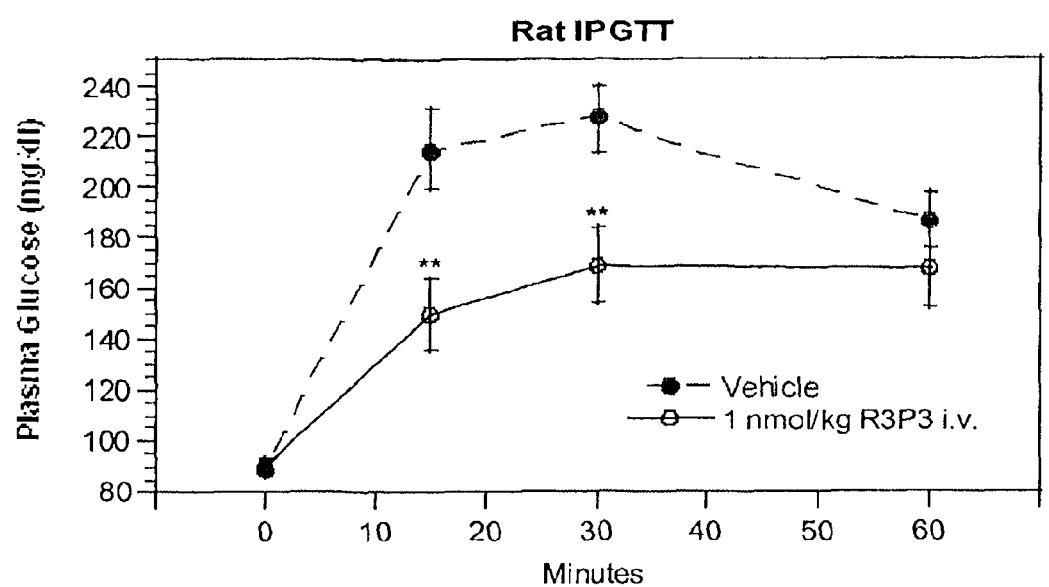
FIG. 5 is a graph showing the R3P3 peptide effect on glucose disposal.

In accordance with the protocol of example 2 above, overnight fasted Wistar rats were anesthetized with pentobarital; i.v. injected with glucose±peptide and eye bled after 1 minute. N=12 rats/group. The graph in FIG. 5 shows that the polypeptide R3P3 causes an increase in glucose disposal that accompanies the increase in insulin secretion. The peptide or vehicle was given i.v. followed by a glucose load given i.p. in accordance with example 3. The plasma glucose was followed over the time period indicated. As shown in the graph, R3P3 markedly accelerated the disposal of blood glucose.

EXAMPLE 10

Diarrhea Side Effects

Figure 6:
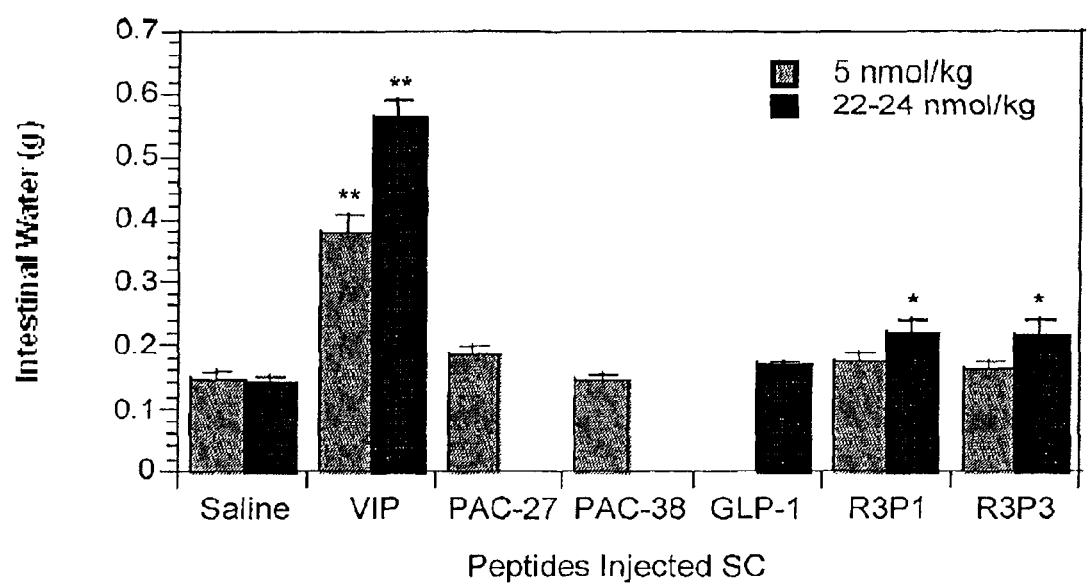
FIG. 6 is a bar chart showing the effect of PACAP and related polypeptides on intestinal water content of Balb/C mice.

As described in the protocol of example 4 above, fasted rats were injected s.c. with the indicated peptide (5 nmol/kg or 22–24 nmol/kg). Five minutes after the injection, 0.3 ml of water was given p.o. Five min after the water dose, the animals were euthanized and the water content in the small intestine determined. As shown in FIG. 6, VIP injections at the two doses caused a marked increase in the water content of the small intestine lumen over the vehicle (saline) control. At the highest dose, the R3 peptides caused only a very small increase (i.e., roughly 10%) in comparison to VIP. At the 5 nmol/kg dose, the peptides did not produce any change in water content in the small gut. The degree of water retention was used as an index of R2 activation in vivo.

EXAMPLE 11

Effect of Peptides on Intraperitoneal Glucose Tolerance in Rats

Wistar rats were fasted overnight and then anesthetized with Pentobarbital. The rats were eye-bled (zero time) and the peptide (in 1% human albumin) was injected subcutaneously. Five minutes later, 1 g/kg of glucose (in saline) was injected intraperitoneally, and the rats were eye-bled after 30 minutes. Plasma glucose levels were determined using the Axon autoanalyzer, and are shown in FIG. 7.

Figure 7:
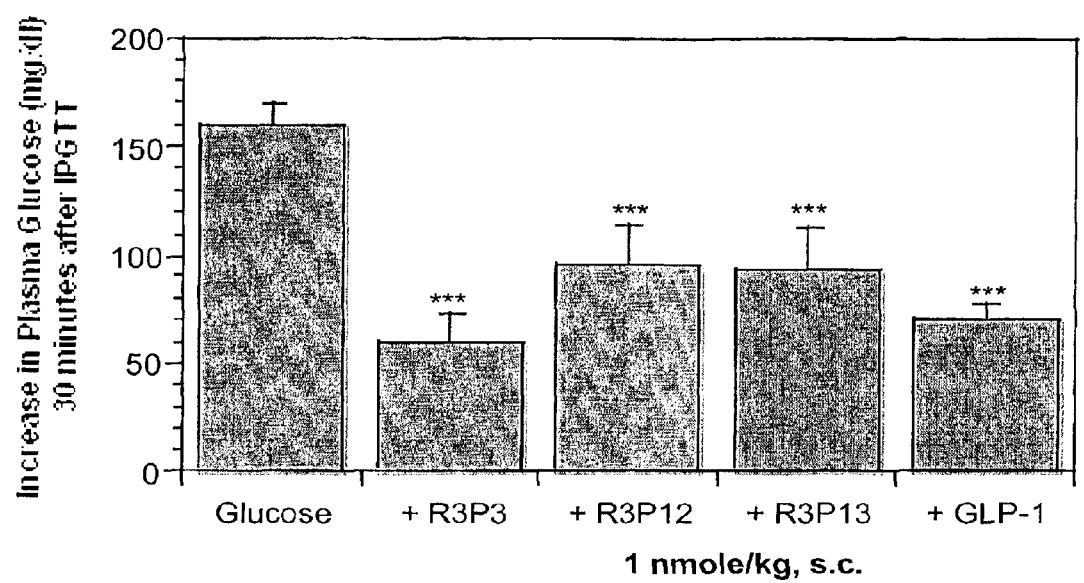
FIG. 7 is a bar chart showing that 1 nmole/kg dose of R3P3, R3P12, R3P13, or GLP-1 enhance glucose disposal in the rat by subcutaneous route of administration.

FIG. 7 shows that plasma glucose elevated to 160 mg/dl above basal (100 mg/dl) in rats treated with vehicle 30 minutes after IPGTT (IP Glucose Tolerance Test). In rats injected with peptides R3P3, R3P12 and R3P13, this elevation of plasma glucose was significantly reduced, verifying the insulin-producing effect. At 1 nmole/kg s.c., the glucose-lowering effect of each peptide was similar to that observed with an equivalent dose of GLP-1.

EXAMPLE 12

Glucose-dependent Insulin Secreting Polypeptides

Table 2 contains a list of the peptides that stimulated release of insulin in vivo in the IPGTT assay, or in vitro through the rat islet assay. As shown by the data, the peptides enhance glucose-mediated insulin release in vivo and in vitro.

Plasma insulin: Data are expressed as % of plasma insulin one minute after IVGTT (0.4 g/kg glucose) with either saline, 0.1 nmol/kg P51, P55, P60, P66 or 1 nmole/kg of the other peptides in Wistar rats. Blood was drawn from the eye and insulin was measured with the rat insulin RIA kit (Linco Research, Inc., St. Charles, Mo.).

Plasma glucose: Data are expressed as % of vehicle of plasma glucose area under the curve after IPGTT (1 g/kg glucose) after treatment with 1 nmol/kg dose of the peptide. PACAP27 has been reported to induce insulin secretion but does not affect plasma glucose levels (Filipsson, K. et al., *J. Clin. Endocrin & Metabolism* 82: 3093–3098 (1997)). The present inventors have shown for the first time that this is because the effects of R2 and R3 on glucose tend to cancel each other out. The R2-selective agonist [K15, R16, L27] VIP(1–7)/GRF(8-27) (Gourlet, P. et al., *Peptides* 18:1539–45 (1997)), defined as R2P1, increases plasma glucose level by 14% while R3-selective agonists lower plasma glucose level by ~20%. Therefore, R3-selectivity appears to be a desirable attribute for medicaments which are to be employed in achieving blood glucose reduction, for treatment of type 2 diabetes.

Islet insulin release: Rat islets were isolated from Sprague-Dawley rats as described in example 1 and treated with either vehicle or specified peptide (10 nM) for 2 hrs. Insulin concentration in the medium was measured with the Linco rat insulin RIA kit. Glucose concentration in the medium was 8 mM. The data are expressed as % of [insulin] in 8 mM glucose alone. No polypeptide-induced increases in insulin concentration were observed at 3 mM glucose; thus, the insulin releasing activity of these polypeptides are glucose-dependent.

TABLE 2

| Peptide | Plasma Insulin (% of Basal) | Plasma Glucose (% of Basal) i.v. | Plasma Glucose (% of Basal) s.c. | Islet Insulin Release (% of Basal) |
|---|---|---|---|---|
| PACAP 27 | 320 | | | 186 |
| R2P1 | 216 | 114 | | |
| P3P0 | | 77 | | 264 |
| P3P1 | 480 | 73 | | 250 |
| P3P3 | 361 | 77 | 72 | 275 |
| P3P9 | | | | 221 |
| P3P10 | | | | 174 |
| P3P12 | 302 | | 76 | 324 |
| P3P13 | 465 | | 77 | 170 |
| R3P19 | 285 | | | |
| R3P36 | 255 | 73 | 78 | |
| P51 | 259 | | | |
| P55 | 208 | | | |
| P60 | 283 | | | |
| R3P66 | 388 | | 82 | 184 |
| R3P77 | 388 | | | |
| R3P80 | 360 | | | |
| R3P81 | 302 | | | |

EXAMPLE 13

Pharmaceutical Composition—IV Formulation

A sterile injectable formulation is made from 4 mg of a polypeptide of SEQ ID NO: 72 and 1 liter of sterile saline, using a manufacturing process well known in the art.

EXAMPLE 14

Pharmaceutical Composition—IV Formulation

A sterile injectable formulation is made from 400 mg of a polypeptide of SEQ ID NO 174 and 1 liter of sterile saline, using a manufacturing process well known in the art.

EXAMPLE 15

Effect of PACAP27, VIP and PACAP Receptor-selective Peptide Agonists on Heart Rate in Conscious Dogs Protocol:

Beagle dogs were put into a sling where they have been trained to stand for up to 3 hours. The cuff of the heart rate monitor was placed around the tail of the dog.

Saline was injected into the cephalic vein and heart rate monitored every 2 minutes to establish a baseline. After 10 minutes, peptide was injected and heart rate monitored every 2 minutes for the next 20 minutes. If heart rate was normal at that time, a higher dose was given and heart rate monitored for 20 minutes. The area under the curve (AUC) for the first 10 minutes of heart rate change induced by the polypeptide was plotted as % over vehicle AUC against polypeptide concentration. PACAP27 and the R1-selective agonist maxadilan (Moro, O., J. Biol. Chem. 272:966–970 (1997)) possess similar potency in heart rate increase. VIP which activates both R2 and R3 but not R1, R2-selective agonist R2P1, and R3 selective agonists R3PO, R3P3, R3P19, R3P36, R3P51, and R3P53 are at least 10-fold less potent than PACAP27 or max Thus, the cardiovascular effect of PACAP27 can be mostly attributed to PACAP-R1 activation. All peptides are full agonists at their respective receptors with comparable affinities. R3P0 is the Roche analog RO 25–1553 that has been shown to display selectivity for PACAP-R3 of at least 100-fold over R1 and R2 (Gourlet et al, Peptides 18:4030408 (1997)).

EXAMPLE 16

Cyclic AMP SPA

CHO cells expressing the PACAP R3 were plated in 96-well plates (Costar) at $8 \times 10^4$ cell/well and grown at 37 C. for 24 hours in α MEM+nucleosides+glutamine (Giobco BRL), 10% FBS, 100 µg/ml Pen/Strep, 0.3 mg/ml glutamine, 1 mM HEPES, 0.5 mg/ml Geneticin (Gibco BRL). The media was removed and the plates were washed with PBS. The cells were incubated with a peptide, in Hepes-PBS-BSA with 0.4 mg/mlSoybean Trypsin Inhibitor, 0.5 mg/ml Bacitracin, 100 uM IBMX, for 15 min at 37 C. Cyclic AMP in the cell extracts was quantitated using the cAMP SPA direct screening assay system (Amersham Pharmacia Biotech Inc, Piscataway, N.J.,). The peptides shown in Table 3 were assayed for cAMP activity.

Table 3 reports in vitro cAMP SPA results on CHO cells transfected with PACAP-R2 or PACAP-R3. EC50 is defined as the concentration of the polypeptide at which 50% of maximum PACAP27 activity is achieved. "NA" denotes no detectable activities. "R3 Selectivity" is derived from the ratio of EC50 at R2 versus EC50 at R3. Most of the following polypeptides are designed based on VIP, which has been shown to lack activity at R1 (Vaudry D. et al., 2000, Pharmacological Reviews, 52: 269–324). Therefore, it is believed that these polypeptides do not possess appreciable activity at R1. Peptides designed based on VIP include SEQ ID NO: 6–53, 62–65, and 70–175.

TABLE 3

| Peptide | Seq ID NO | R2 EC50, nM | R3 EC50, nM | R3 Selectivity |
|---|---|---|---|---|
| VIP | 1 | 0.1 | 0.08 | 1.3 |
| R3P0 | 5 | >100 | 0.4 | >250 |
| R3P1 | 6 | >100 | 2 | >50 |
| R3P2 | 7 | >1000 | 3 | >300 |
| R3P3 | 8 | 100 | 0.75 | 130 |
| R3P5 | 10 | 200 | 7 | 30 |
| R3P8 | 11 | 2 | 1.4 | 1.5 |
| R3P9 | 12 | 40 | 2 | 20 |
| R3P10 | 13 | 3 | 11 | 0.3 |
| R3P11 | 14 | 10 | 3 | 3 |
| R3P12 | 15 | >100 | 0.5 | >200 |
| R3P13 | 16 | 163 | 5 | 33 |
| R3P14 | 17 | 50 | 17 | 3 |
| R3P19 | 18 | 42 | 1.4 | 30 |
| R3P20 | 19 | 330 | 1.4 | 230 |
| R3P21 | 20 | 17 | 0.3 | 60 |
| R3P22 | 21 | 38 | 1.6 | 24 |
| R3P24 | 22 | 45 | 1.3 | 34 |
| R3P25 | 23 | 15 | 0.7 | 20 |
| R3P26 | 24 | >100 | 0.55 | >180 |
| R3P29 | 25 | >100 | 0.5 | >200 |
| R3P30 | 26 | 20 | 0.4 | 50 |
| R3P31 | 27 | >100 | 0.3 | >300 |
| R3P32 | 28 | 84 | 0.4 | 200 |
| R3P33 | 29 | >100 | 0.5 | >200 |
| R3P34 | 30 | >100 | 1.4 | >70 |
| R3P35 | 31 | >100 | 2.6 | >40 |
| R3P36 | 32 | >90 | 0.4 | >200 |
| R3P41 | 33 | 8 | 0.08 | 100 |
| R3P42 | 34 | 0.3 | 0.03 | 10 |
| R3P43 | 35 | 0.8 | 0.08 | 10 |
| R3P44 | 36 | 8 | 1.3 | 6 |
| R3P45 | 37 | NA | NA | |
| R3P46 | 38 | 0.4 | 0.06 | 7 |
| R3P47 | 39 | 0.7 | 0.12 | 6 |
| R3P48 | 40 | 1 | 0.13 | 8 |
| R3P49 | 41 | 8 | 0.27 | 30 |
| R3P50 | 42 | 0.7 | 0.13 | 6 |
| R3P51 | 43 | 23 | 0.26 | 90 |
| R3P52 | 44 | >100 | 0.4 | >250 |
| R3P53 | 45 | 500 | 0.2 | 2500 |
| R3P54 | 46 | >100 | 0.5 | >200 |
| R3P55 | 47 | 50 | 0.17 | 280 |
| R3P56 | 48 | 40 | 0.4 | 100 |
| R3P57 | 49 | 42 | 0.23 | 190 |
| R3P58 | 50 | 55 | 0.32 | 170 |
| R3P59 | 51 | 10 | 0.15 | 70 |
| R3P60 | 52 | 120 | 1 | 120 |
| R3P61 | 53 | 110 | 0.8 | 140 |
| R3P6 | 57 | 220 | 80 | 3 |
| R3P7 | 58 | 2 | 4 | 0.5 |
| R3P15 | 59 | 12 | 5 | 2 |
| R3P16 | 60 | 14 | 10 | 1.4 |
| R3P17 | 61 | 9 | 4 | 2 |
| R3P18 | 62 | NA | NA | |
| R3P23 | 63 | 10 | 0.43 | 23 |
| R3P27 | 64 | 6.4 | 0.8 | 8 |
| R3P28 | 65 | 8 | 7 | 1 |
| R3P37 | 66 | 71 | 4 | 18 |
| R3P38 | 67 | 17 | 2.3 | 7 |
| R3P39 | 68 | 1 | 0.5 | 2 |
| R3P40 | 69 | 1.4 | 0.7 | 2 |
| R3P62 | 70 | 180 | 1.8 | 100 |
| R3P65 | 71 | 80 | 0.6 | 130 |
| R3P66 | 72 | 100 | 0.4 | 250 |
| R3P67 | 73 | 100 | 0.3 | 330 |
| R3P68 | 74 | 130 | 0.5 | 260 |
| R3P69 | 75 | 90 | 0.5 | 190 |
| R3P70 | 76 | >100 | 0.4 | >250 |
| R3P71 | 77 | 56 | 0.09 | 660 |
| R3P72 | 78 | >100 | 0.16 | >600 |
| R3P73 | 79 | 50 | 0.3 | 170 |
| R3P74 | 80 | 90 | 0.6 | 150 |
| R3P75 | 81 | >150 | 0.3 | >500 |
| R3P76 | 82 | >150 | 0.1 | >1500 |
| R3P77 | 83 | 200 | 0.4 | 500 |
| R3P78 | 84 | 250 | 1.1 | 230 |
| R3P79 | 85 | 100 | 0.5 | 200 |
| R3P80 | 86 | 88 | 0.44 | 200 |
| R3P81 | 87 | 50 | 0.5 | 100 |
| R3P82 | 88 | 10 | 0.4 | 23 |
| R3P83 | 89 | 5 | 0.08 | 60 |
| R3P84 | 90 | 2.5 | 0.06 | 40 |
| R3P85 | 91 | 5 | 0.18 | 30 |
| R3P86 | 92 | 90 | 0.8 | 110 |
| R3P87 | 93 | 0.6 | 0.2 | 3 |
| R3P88 | 94 | 0.89 | 0.08 | 12 |
| R3P89 | 95 | 0.9 | 0.06 | 15 |

TABLE 3-continued

| Peptide | Seq ID NO | R2 EC50, nM | R3 EC50, nM | R3 Selectivity |
|---|---|---|---|---|
| R3P92 | 98 | 2 | 0.02 | 100 |
| R3P93 | 98 | 6 | 0.14 | 40 |
| R3P94 | 99 | 9 | 0.09 | 100 |
| R3P98 | 101 | NA | NA | |
| R3P99 | 102 | 40 | 1.0 | 40 |
| R3P100 | 103 | 10 | 0.3 | 30 |
| R3P101 | 104 | 400 | 1.0 | 400 |
| R3P102 | 105 | 300 | 60.0 | 5 |
| R3P103 | 106 | 0.4 | 0.05 | 8 |
| R3P104 | 107 | 100 | 0.2 | 500 |
| R3P105 | 108 | 1 | 0.3 | 3 |
| R3P106 | 109 | 2 | 0.1 | 20 |
| R3P107 | 110 | 1000 | 200.0 | 5 |
| R3P108 | 111 | 1000 | 300.0 | 3 |
| R3P109 | 112 | 1000 | 10.0 | 100 |
| R3P110 | 113 | 100 | 0.5 | 200 |
| R3P111 | 114 | 1000 | 3.0 | 300 |
| R3P112 | 115 | 4 | 0.1 | 40 |
| R3P113 | 116 | 3 | 0.3 | 10 |
| R3P114 | 117 | 20 | 2.0 | 10 |
| R3P115 | 118 | 300 | 6.0 | 50 |
| R3P116 | 119 | 20 | 1.0 | 20 |
| R3P118 | 121 | 15 | 0.5 | 30 |
| R3P119 | 122 | 15 | 0.5 | 30 |
| R3P120 | 123 | 10 | 0.2 | 50 |
| R3P121 | 124 | 50 | 1.0 | 50 |
| R3P122 | 125 | 10 | 0.2 | 50 |
| R3P123 | 126 | 5 | 0.1 | 50 |
| R3P124 | 127 | 3 | 0.2 | 15 |
| R3P125 | 128 | 60 | 2.0 | 30 |
| R3P126 | 129 | 200 | 1.0 | 200 |
| R3P127 | 130 | 300 | 0.5 | 600 |
| R3P128 | 131 | 60 | 0.3 | 200 |
| R3P129 | 132 | 50 | 1.0 | 50 |
| R3P130 | 133 | 40 | 1.0 | 40 |
| R3P131 | 134 | 20 | 0.3 | 70 |
| R3P132 | 135 | 10 | 0.2 | 50 |
| R3P133 | 136 | 8 | 0.1 | 80 |
| R3P134 | 137 | 40 | 0.4 | 100 |
| R3P136 | 139 | 20 | 0.3 | 70 |
| R3P137 | 140 | 30 | 0.3 | 100 |
| R3P139 | 142 | 20 | 0.4 | 50 |
| R3P140 | 143 | 15 | 0.3 | 50 |
| R3P141 | 144 | 20 | 0.2 | 100 |
| R3P142 | 145 | 6 | 0.2 | 30 |
| R3P143 | 146 | 6 | 0.2 | 30 |
| R3P144 | 147 | 300 | 3.0 | 100 |
| R3P145 | 148 | 50 | 0.5 | 100 |
| R3P146 | 149 | 30 | 0.3 | 100 |
| R3P147 | 150 | 100 | 0.2 | 500 |
| R3P148 | 151 | 30 | 0.3 | 100 |
| R3P149 | 152 | 40 | 0.5 | 80 |
| R3P150 | 153 | 40 | 0.8 | 50 |
| R3P153 | 156 | 40 | 0.2 | 200 |
| R3P155 | 157 | 40 | 0.4 | 100 |
| R3P156 | 158 | 100 | 1.0 | 100 |
| R3P157 | 159 | 50 | 0.3 | 170 |
| R3P158 | 160 | 6 | 0.07 | 90 |
| R3P159 | 161 | 200 | 0.5 | 400 |
| R3P160 | 162 | 100 | 0.2 | 500 |
| R3P161 | 163 | 60 | 0.2 | 300 |
| R3P162 | 164 | 20 | 0.1 | 200 |
| R3P163 | 165 | 40 | 0.2 | 200 |
| R3P164 | 166 | 100 | 0.3 | 300 |
| R3P165 | 167 | 150 | 0.5 | 300 |
| R3P166 | 168 | 50 | 0.1 | 500 |
| R3P167 | 169 | 300 | 1.0 | 300 |
| R3P168 | 170 | 60 | 0.2 | 300 |
| R3P169 | 171 | 60 | 0.2 | 300 |
| R3P170 | 172 | 20 | 0.1 | 200 |
| R3P171 | 173 | 80 | 0.4 | 200 |
| R3P172 | 174 | 77 | 2.6 | 29 |
| R3P173 | 175 | NA | 200 | |
| PAC1 | 176 | 970 | 10 | 97 |
| PAC2 | 177 | NA | 34 | |
| PAC3 | 178 | NA | NA | |
| PAC4 | 179 | 45 | 7 | 6 |
| PAC5 | 180 | 1.8 | 0.7 | 2 |
| PAC6 | 181 | NA | NA | |
| PAC7 | 182 | NA | NA | |
| PAC8 | 183 | 43 | 47 | 1 |
| PAC9 | 184 | 0.9 | 0.7 | 1 |
| PAC10 | 185 | 110 | 27 | 4 |
| PAC11 | 186 | 10 | 140 | 0.1 |
| PAC12 | 187 | 150 | 3 | 50 |
| PAC13 | 188 | 3 | 0.5 | 6 |
| PAC14 | 189 | 110 | 1.6 | 70 |
| PAC15 | 190 | 2.4 | 0.2 | 12 |
| PAC16 | 191 | 0.2 | 0.2 | 1 |
| PAC17 | 192 | 0.25 | 0.15 | 1.6 |
| PAC18 | 193 | 0.7 | 1.1 | 0.7 |
| PAC19 | 194 | 8 | 0.4 | 20 |
| PAC20 | 195 | 20 | 0.7 | 30 |
| PAC21 | 196 | 2.5 | 0.24 | 10 |
| PAC22 | 197 | 2 | 15 | 0.1 |
| PAC23 | 198 | 170 | 13 | 13 |
| PAC24 | 199 | 0.3 | 0.2 | 1.5 |
| PAC25 | 200 | 0.13 | 0.04 | 3 |
| PAC26 | 201 | 0.25 | 0.3 | 1 |
| PAC27 | 202 | 1.5 | 1.1 | 1.4 |
| rR3P174 | 322 | 18 | 0.20 | 90 |
| rR3P175 | 323 | 400 | 2.2 | 180 |
| rR3P176 | 324 | 300 | 2.0 | 150 |
| rR3P177 | 325 | 110 | 1.6 | 70 |
| rR3P178 | 326 | 80 | 0.75 | 110 |
| rR3P179 | 327 | 230 | 1.5 | 150 |
| rR3P180 | 328 | >100 | 6.7 | >20 |
| rR3P181 | 329 | 280 | 5.1 | 50 |
| rR3P182 | 330 | 280 | 3.2 | 90 |
| rR3P183 | 331 | >150 | 5.4 | >30 |
| rR3P184 | 332 | 10 | 0.37 | 30 |
| rR3P185 | 333 | 180 | 4.5 | 40 |
| rR3P186 | 334 | 70 | 1.6 | 44 |
| rR3P187 | 335 | >130 | 1.6 | >80 |
| rR3P188 | 336 | 150 | 2.2 | 70 |
| rR3P189 | 337 | 1.3 | 0.04 | 30 |
| rR3P190 | 338 | 220 | 2.2 | 100 |
| rR3P191 | 339 | >200 | 2.7 | >80 |
| rR3P192 | 340 | 40 | 0.60 | 60 |
| rR3P193 | 341 | 200 | 1.9 | 110 |

EXAMPLE 17

Polyclonal Antibody Production

Synthesis of the peptide AC-CRKQVAAKKYLQSIKNKRY-COOH (SEQ ID NO: 342) was performed on an Applied Biosystems 430A peptide synthesizer using fmoc chemistry with HBTU activation of amino acids. The peptide was cleaved using a 84.6% TFA, 4.4% phenol, 4.4% water, 4.4% thioanusol, and 2.2% ethandithiol cocktail. The crude peptide was purified using a C18 reverse phase column with a 0.1% TFA/CH3CN gradient. Evaluation of purity was performed on a PerSeptive V Biosystems Voyager DE Pro MALDI mass spectrometer. The cysteine residue was coupled to KLII using the Pierce Inject Maleimide Activated mcKLII kit and protocol (Pierce, Rockford, Ill.). Rabbits were immunized using the following polyclonal antiserum immunization schedule:

Rabbits were immunized using the following polyclonal antiserum immunization schedule:

Day 0—10 ml prebleed for baseline serum 250 ug each peptide in 1 ml emulsion of Complete Freunds Adjuvant, 0.1 ml/site×10 sites subcutaneously Day 14—Boost 250 μg each peptide in 1 ml emulsion of Incomplete Freunds Adjuvant
0.1 ml/site×10 sites subcutaneously
Day 21—35 ml bleed
Day 35—Boost 250 μg each peptide in 1 ml emulsion of Incomplete Freunds Adjuvant
0.1 ml/site×10 sites subcutaneously
Day 42—35 ml bleed
Day 56—Boost 250 μg each peptide in 1 ml emulsion of Incomplete Freunds Adjuvant
0.1 ml/site×10 sites subcutaneously
Day 63—35 ml bleed
Day 77—Boost 250 μg each peptide in 1 ml emulsion of Incomplete Freunds Adjuvant
0.1 ml/site×10 sites subcutaneously
Day 84—Terminal bleed
Antibodies were Characterized Using the Following Protocol:

Immulon III plate (DYNATECH LABORATORIES, INC, Chantilly, Va.) was coated with P66 peptide (0.3–100 ng range) in 100 ul of EIA coating buffer 1.6 L of 0.1M NaHCO3+0.4 L of 0.1M Na2CO3 pH9.5) for 3 hours at room temperature (RT). The plate was blotted with 100 ul of 5% milk TBS Tween 20 (10 mM tris pH8.0, 150 mM NaCl, 0.05% Tween-20 (SIGMA P-1379)) for 1 hour at RT and washed 3 times with TBS Tween. R3P66 antibody was added to the well in 100 ul of 5% bloto (TBS-Tween 20+5% milk ) for 2 hours RT followed by a wash with TBS Tween (repeat wash 5 times). Secondary antibody (BioRad goat anti rabbit Alkaline Phosphatase conjugate) was added to the well at 1:1000 dilution in 100 ul of 5% bloto for 1 hour. The plate was washed 5 times with TBS Tween. p-Nitrophenyl Phosphate (SIGMA 104–105) 0.5 mg/ml of substrate buffer (1M Diethanolamine, 0.5 uM MgCl2.6H2O, pH 9.8 w/HCl ) in 100 ul and incubated at RT for 1 hour to O/N. The plate was read at OD 405 in SPECTRAmax 250 (Molecular Devices Corporation, Sunnyvale, Calif.).

To determine if the antibodies produced in rabbits to the peptide Ac-CRKQVAAKKYLQSIKNKRY-COOH (SEQ ID NO: 342) in accordance with example 17 recognize the peptide R3P66 (SEQ ID NO 72), the enzyme-linked immunoadsorbent assay (ELISA) was performed. When antibodies recognize a peptide, a signal at OD405 is detected. FIG. 10 shows that these antibodies recognize R3P66 but do not interact with homologous peptides PACAP-27 or VIP up to 30 ug of peptide concentration.

EXAMPLE 18

Airway Hyperresponsiveness in the Primate Acute Asthma Model

Male cynomolgus monkeys (*Macaca fascicularls*) used in this study were maintained at constant temperature and humidity with a twelve hour light cycle. They were fed twice daily, except on an experimental day when food was withheld the night before the procedure. Water was available ad lib at all times.

Airway hyperresponsiveness (AHR)(baseline) was measured 1 week before the control (no treatment) antigen challenge, and again 24 hrs after antigen challenge. Antigen-induced airway hyperresponsiveness was measured by a fall in the $PC_{100}$ (the concentration of methacholine required to cause a 100% increase in lung resistance) at 24 hr compared to baseline. After 2 weeks rest, another baseline measurement of AHR was performed. One week later, peptides of this invention were administered as an aerosol, 10 minutes before antigen challenge. After 24 hrs, AHR was again measured, and the fall in $PC_{100}$ with treatment was compared to that without treatment.

Experimental Procedure. On each experimental day animals were anaesthetized with a ketamine/xylazine mixture (70:12 mg kg$^{-1}$ @ 0.1 ml kg$^{-1}$) while still in their cage. When unconscious they were brought into the primate laboratory where they were placed in a supine position on a heated water blanket on a trolley. Ophthalmic ointment was wiped onto each eye, and 0.2 ml lidocaine (2%,) sprayed onto the larynx and over the back of the throat. The Jaws were held apart by a jaw spreader and a cuffed 5.0 gauge endotracheal tube (with the end liberally smeared with xylocaine gel, 2%) was inserted with the aid of laryngoscope. The animal was then placed into a specially designed restraint chair such that the animal was in a slightly reclined but upright sitting position, secured only by a collar at the neck. A water-heated blanket surrounded the animal.

The endotracheal tube was connected to a Harvard Ventilator adjusted to deliver 30–35 breaths per minute. Airflow was measured by a Fleisch pneumotachograph and thoracic pressure was measured by a validyne pressure transducer (as the difference between the pressure at the distal end of the et tube and room pressure).

The pneumotachograph and validyne were connected to a pre-amplifier and then into an MI$^2$ respiratory analyser. Using the primary signals of flow and pressure the analyser computed airway resistance and compliance (as well as a number of other respiratory parameters). An initial measurement of 5–6 minutes was carried out to ensure the signals were steady and that the values for resistance and compliance were within recognized limits.

Antigen challenge: This was an inhalation challenge with *Ascaris suum*. The supplied *Ascaris suum* extract was diluted tenfold with PBS to give a 1000 ug/ml solution. The aerosol was delivered with a pressure driven Rainbow drop nebuliser (Puritan-Bennett) connected to a Bird mark 7A respirator, set to deliver 15 breaths per minute. 30 breaths of antigen were administered after which the acute bronchoconstriction was monitored for 15 min.

After the challenge had been finished the animal was weaned off the ventilator, and when he could breath for himself was released from the restraint chair and laid supine on the trolley. When the normal reflexes (eye blink, swallow) had returned, along with muscle tone in the limbs the animal was returned to its cage.

Peptide Administration: Peptides under evaluation were delivered by inhalation as above. Stock solutions of the peptides were diluted with sterile water to achieve a concentration of 0.5 ug/4 ul. From previous measurements the nebuliser had been demonstrated to deliver 4 ul/breath, and the number of breaths administered to each animal was adjusted to deliver the correct final concentration from the nebuliser. For each peptide the final concentrations delivered were as follows:

R3P0 (SEQ ID NO:5)—0.6 ug/kg
R3P76 (SEQ ID NO:82)—3 ug/kg
R3P82 (SEQ ID NO:88)—1.8 ug/kg

Methacholine challenge: Methacholine dose response curves were carried out to assess the airway hyperresponsiveness. In the acute model, this was measured at +24 hour and compared to the responsiveness 7 days before treatment. An aerosol of phosphate buffered saline (PBS) was delivered using a nebuliser as above. The aerosol was administered for 15 breaths and then lung resistance was monitored for ten minutes. Methacholine (Sigma) was made up at a concentration of 100 mg/ml in PBS and this stock solution was diluted with PBS to a final range of concentrations from 0.1 mg/ml through to 100 mg/ml. Methacholine (0.1 mg/ml, 15 breaths) was administered followed by another ten minutes monitoring. Successive doses of methacholine were administered with the dose increasing by a half-log at each step until either the lung resistance had doubled or the maximum dose of methacholine (100 mg/ml)had been administered. The baseline (zero %) resistance was taken as the resistance achieved following the PBS administration. The increase in lung resistance (%) and the methacholine doses were entered into a spreadsheet and the $PC_{100}$ (the dose of methacholine to cause a 100% increase in resistance) was calculated from a graph of dose against resistance. These values were converted to $log_{10}$ values. The delta $PC_{100}$ (+24 hr value—baseline value) for the treated study was compared to that for the control study.

Table 4 shows the $PC_{100}$ data for the three peptides. As shown by the data, the peptides are effective against antigen-induced airway hyperresponsiveness, and are thus likely to be a potential asthma therapy.

TABLE 4

$PC_{100}$ data for all three peptide studies.

| | Peptide (dose) | | | | | |
|---|---|---|---|---|---|---|
| | R3P0 (0.6 ug/mg) | | R3P76 (3.0 ug/kg) | | R3P82 (1.8 ug/kg) | |
| | Control | Treated | Control | Treated | Control | Treated |
| Delta $log_{10}$ $PC_{100}$ | | | | | | |
| N | 4 | 4 | 5 | 5 | 4 | 4 |
| Mean* | −0.325 | −0.150 | −0.468 | +0.047 | −0.567 | −0.067 |
| SD | 0.177 | 0.152 | 0.128 | 0.253 | 0.361 | 0.329 |

TABLE 4-continued $PC_{100}$ data for all three peptide studies.

| | Peptide (dose) | | |
|---|---|---|---|
| | R3P0 (0.6 ug/mg) Control Treated | R3P76 (3.0 ug/kg) Control Treated | R3P82 (1.8 ug/kg) Control Treated |
| P(Treated vs Control) | 0.240 | 0.031 | 0.087 |
| % Inhibition of induced AHR | 54 | 100 | 88 |

*The larger the negative value, the more hyperresponsive the animal becomes.

All publications and patents mentioned in the above specification are incorporated herein by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims. Those skilled in the art will recognize, or be able to ascertain using no more than routine experimentation, many equivalents to the specific embodiments of the invention described herein. Such equivalents are intended to be encompassed by the following claims.

We claim:

1. A polypeptide consisting of the amino acid sequence of SEQ ID NO: 72.

2. A pharmaceutical composition comprising a polypeptide of claim 1 in combination with a pharmaceutically acceptable carrier.

3. A method of treating diabetes or impaired glucose tolerance in a mammal comprising administering to the mammal a therapeutically effective amount of the polypeptide of claim 1 or the pharmaceutical composition of claim 2.

4. The method of claim 3, wherein said diabetes is type 2 diabetes.

5. A method of stimulating insulin release in a glucose-dependent manner in a mammal comprising administering to the mammal a therapeutically effective amount of the polypeptide of claim 1 or the pharmaceutical composition of claim 2.

* * * * *